(12) United States Patent
Blahnik et al.

(10) Patent No.: US 11,738,168 B2
(45) Date of Patent: Aug. 29, 2023

(54) BREATHING SEQUENCE USER INTERFACE

(71) Applicant: Apple Inc., Cupertino, CA (US)

(72) Inventors: Jay Blahnik, San Francisco, CA (US); Julie A. Arney, Los Gatos, CA (US); Samuel H. Bebbington, San Francisco, CA (US); Gary Ian Butcher, Los Gatos, CA (US); Jules K. Fennis, Auburn, WA (US); Monica Jenkins, Marina Del Rey, CA (US)

(73) Assignee: Apple Inc., Cupertino, CA (US)

( * ) Notice: Subject to any disclaimer, the term of this patent is extended or adjusted under 35 U.S.C. 154(b) by 125 days.

(21) Appl. No.: 17/345,092

(22) Filed: Jun. 11, 2021

(65) Prior Publication Data

US 2021/0338971 A1 Nov. 4, 2021

Related U.S. Application Data

(63) Continuation of application No. 15/372,133, filed on Dec. 7, 2016, now Pat. No. 11,033,708.

(Continued)

(51) Int. Cl.
*A61M 21/02* (2006.01)
*G06F 3/01* (2006.01)
(Continued)

(52) U.S. Cl.
CPC .............. *A61M 21/02* (2013.01); *G06F 3/00* (2013.01); *G06F 3/01* (2013.01); *G06F 3/011* (2013.01);
(Continued)

(58) Field of Classification Search
CPC .......... A61B 5/0816; A61M 21/00–02; A61M 2021/0005–0088; A61M 2205/505;
(Continued)

(56) References Cited

U.S. PATENT DOCUMENTS 6,662,023 B1  12/2003 Helle
7,199,700 B1   4/2007 McPherson et al.
(Continued)

FOREIGN PATENT DOCUMENTS

CN   101822894 A   9/2010
CN   102488501 A   6/2012
(Continued)

OTHER PUBLICATIONS iPhoneTricks.org "Apple Watch Activity App Setup & Usage Tips". May 4, 2015. Accessed Jan. 20, 2023 from https://www.iphonetricks.org/apple-watch-activity-app-setup-usage-tips/ (Year: 2015).*

(Continued)

*Primary Examiner* — Kaylee R Wilson
(74) *Attorney, Agent, or Firm* — DLA Piper LLP (US)

(57) ABSTRACT

The present disclosure generally relates to user interfaces for breathing sequences. In some examples, a device displays a configuration user interface that comprises a prompt to select a number of cycles of a breathing sequence, adjusts the number of cycles of the breathing sequence to the selected number of cycles in response to selection, and initiates a breathing phase of the breathing sequence. In some examples, the device displays and fluctuates a progress indicator in accordance with the selected number of cycles. In some examples, a device detects a time associated with a first breathing sequence, generates a prompting criteria based on a predetermined prompting frequency and the detected time, determines if the prompting criteria has been met, displays a prompt to initiate a second breathing sequence, wherein the prompt comprises a first affordance, and displays a second breathing sequence user interface in response to selection of the first affordance.

48 Claims, 42 Drawing Sheets

Related U.S. Application Data

(60) Provisional application No. 62/348,844, filed on Jun. 10, 2016.

(51) Int. Cl.
  *G06F 3/048* (2013.01)
  *G06F 3/00* (2006.01)
  *A61M 21/00* (2006.01)

(52) U.S. Cl.
  CPC ....... *G06F 3/048* (2013.01); *A61M 2021/005* (2013.01); *A61M 2021/0022* (2013.01); *A61M 2021/0088* (2013.01); *A61M 2205/332* (2013.01); *A61M 2205/3553* (2013.01); *A61M 2205/3592* (2013.01); *A61M 2205/505* (2013.01); *A61M 2205/581* (2013.01); *A61M 2205/582* (2013.01); *A61M 2205/583* (2013.01); *A61M 2230/10* (2013.01); *A61M 2230/40* (2013.01); *G06F 2203/04808* (2013.01)

(58) Field of Classification Search
  CPC ...... A61M 2021/005; A61M 16/00–22; A61M 2016/0015–1035; G06F 3/017; G06F 3/048; A63B 23/185
  See application file for complete search history.

(56) References Cited

U.S. PATENT DOCUMENTS

| | | | |
|---|---|---|---|
| 8,543,081 B2 | 9/2013 | Scott et al. | |
| 8,562,489 B2 | 10/2013 | Burton et al. | |
| 8,666,361 B2 | 3/2014 | Chu et al. | |
| 2003/0171643 A1* | 9/2003 | Noguchi | A61M 21/00 600/26 |
| 2004/0254501 A1* | 12/2004 | Mault | A61B 5/486 600/587 |
| 2005/0165609 A1* | 7/2005 | Zuberec | G10L 15/22 704/E15.04 |
| 2006/0155578 A1 | 7/2006 | Eisenberger et al. | |
| 2007/0129883 A1* | 6/2007 | Kuo | G01C 21/3652 701/533 |
| 2007/0135043 A1 | 6/2007 | Hayes et al. | |
| 2008/0072902 A1 | 3/2008 | Setzer et al. | |
| 2008/0319279 A1 | 12/2008 | Ramsay et al. | |
| 2009/0205041 A1 | 8/2009 | Michalske | |
| 2009/0263773 A1* | 10/2009 | Kotlyar | G09B 19/003 715/764 |
| 2009/0322686 A1* | 12/2009 | Jayasinghe | G06F 3/04886 345/173 |
| 2010/0035669 A1* | 2/2010 | Jang | H04M 1/0237 455/575.4 |
| 2010/0069774 A1* | 3/2010 | Bingham | A61B 5/486 600/538 |
| 2010/0095961 A1 | 4/2010 | Tornesel et al. | |
| 2010/0273610 A1 | 10/2010 | Johnson | |
| 2011/0088086 A1 | 4/2011 | Swink et al. | |
| 2011/0137678 A1 | 6/2011 | Williams | |
| 2012/0258684 A1 | 10/2012 | Franz et al. | |
| 2013/0143512 A1 | 6/2013 | Hernandez et al. | |
| 2013/0225118 A1 | 8/2013 | Jang et al. | |
| 2013/0262155 A1 | 10/2013 | Hinkamp | |
| 2013/0290013 A1 | 10/2013 | Forrester et al. | |
| 2013/0295872 A1 | 11/2013 | Guday et al. | |
| 2013/0333703 A1 | 12/2013 | Wallace et al. | |
| 2014/0018049 A1* | 1/2014 | Cannon | H04W 4/16 455/414.1 |
| 2014/0344375 A1 | 11/2014 | Hauser et al. | |
| 2015/0096564 A1 | 4/2015 | Cosnek | |
| 2015/0283337 A1 | 10/2015 | Adams et al. | |
| 2015/0347711 A1 | 12/2015 | Soli et al. | |
| 2015/0350861 A1 | 12/2015 | Soli et al. | |
| 2016/0007911 A1 | 1/2016 | Wu et al. | |
| 2016/0019360 A1 | 1/2016 | Pahwa et al. | |
| 2016/0058337 A1 | 3/2016 | Blahnik et al. | |
| 2016/0114213 A1 | 4/2016 | Lee | |
| 2017/0243508 A1 | 8/2017 | Cheng et al. | |
| 2017/0332972 A1 | 11/2017 | Nagasaki et al. | |
| 2017/0354795 A1 | 12/2017 | Blahnik et al. | |
| 2018/0329584 A1 | 11/2018 | Williams et al. | |
| 2021/0113116 A1 | 4/2021 | Chen et al. | |
| 2022/0080261 A1 | 3/2022 | Li | |
| 2022/0374106 A1 | 11/2022 | Arney et al. | |

FOREIGN PATENT DOCUMENTS

| | | |
|---|---|---|
| JP | 6-187118 A | 7/1994 |
| JP | 2001-76078 A | 3/2001 |
| JP | 2003-305094 A | 10/2003 |
| JP | 2003-337863 A | 11/2003 |
| JP | 2004-102609 A | 4/2004 |
| JP | 2006-230679 A | 9/2006 |
| JP | 2007-190275 A | 8/2007 |
| JP | 2007-190276 A | 8/2007 |
| JP | 2008-183339 A | 8/2008 |
| JP | 2009-119068 A | 6/2009 |
| JP | 2010-104456 A | 5/2010 |
| JP | 2010-533541 A | 10/2010 |
| JP | 2011-125633 A | 6/2011 |
| JP | 2011-192126 A | 9/2011 |
| JP | 2012-19852 A | 2/2012 |
| JP | 2012-35055 A | 2/2012 |
| JP | 2012-524639 A | 10/2012 |
| JP | 2013-131215 A | 7/2013 |
| JP | 2018-504159 A | 2/2018 |
| KR | 10-2010-0024503 A | 3/2010 |
| KR | 10-2013-0142412 A | 12/2013 |
| KR | 10-2014-0138361 A | 12/2014 |
| TW | 201210368 A | 3/2012 |
| TW | 201240499 A | 10/2012 |
| WO | 1999/41682 A2 | 8/1999 |
| WO | 2005/018737 A1 | 3/2005 |
| WO | 2008/110956 A1 | 9/2008 |
| WO | 2009/002577 A1 | 12/2008 |
| WO | 2012/078079 A2 | 6/2012 |
| WO | 2012/117376 A1 | 9/2012 |
| WO | 2015/039979 A1 | 3/2015 |
| WO | 2018/209152 A1 | 11/2018 |

OTHER PUBLICATIONS macrumors.com "How to Use the Activity and Workout Apps on Apple Watch". May 4, 2015. Accessed Jan. 20, 2023 from https://www.macrumors.com/how-to/apple-watch-activity-workout-apps/ (Year: 2015).*

WindowsUnited "Breathe deeply now! Please take a deep breath and relax". Machine English translation and original German document. Published online Oct. 4, 2014, accessed Jul. 17, 2018. https://windowsunited.de/breathe-deeply-now-die-app-gegen-angszustaende (Year: 2014).*

Appx4fun. Breathe Deeply Now! 2.5.0.0XAP for Windows Phone. Released Feb. 15, 2015. Accessed Jul. 19, 2018. https://www.appx4fun.com/apps/5402/ (Year: 2015).*

Tiles and Toasts. "Toast Notification and Action Center Overview for Windows 10". Published online Jul. 8, 2015. Accessed Jul. 17, 2018. https://blogs.msdn.microsoft.com/tiles_and_toasts/2015/07/08/toast-notification-and-action-center-overview-for-windows-10/ (Year: 2015).*

Stachowiak, Sandy. "Relax, breathe deep and regain focus with Hear and Now" Jan. 6, 2016 retrieved from https://appadvice.com/appnn/2016/01/relax-breathe-deep-and-regain-focus-with-hear-and-nowon Mar. 31, 2020 (Year: 2016) (Year: 2016).*

Office Action received for Korean Patent Application No. 10-2022-7010343, dated May 19, 2022, 12 pages (6 pages of English Translation and 6 pages of Official Copy).

Office Action received for Australian Patent Application No. 2021203301, dated Jan. 18, 2022, 3 pages.

Notice of Allowance received for Korean Patent Application No. 10-2021-7015702, dated Dec. 27, 2021, 3 pages (Official Copy Only) {See communication under Rule 37 CFR § 1.98(a) (3)}.

(56) References Cited

OTHER PUBLICATIONS

Notice of Allowance received for Korean Patent Application No. 10-2020-7016741, dated Feb. 24, 2021, 5 pages (2 pages of English Translation and 3 pages of Official Copy).
Office Action received for Korean Patent Application No. 10-2020-7016741, dated Jul. 22, 2020, 10 pages (4 pages of English Translation and 6 pages of Official Copy).
Wesley, "Apple Watch Series 1", Online available at: http://toolbox.info/blog/archives/1737-unknown.html, May 28, 2015, 5 pages (Official Copy Only).
International Search Report and Written Opinion received for PCT Patent Application No. PCT/US2022/030309, dated Sep. 15, 2022, 14 pages.
Non-Final Office Action received for U.S. Appl. No. 17/550,806, dated Nov. 28, 2022, 21 pages.
Office Action received for Korean Patent Application No. 10-2022-7010343, dated Nov. 17, 2022, 6 pages (3 pages of English Translation and 3 pages of Official Copy).
Allthingsgizmo, "How to Multitask on the AppleWatch", Available Online at https://www.youtube.com/watch?v=Mxt2tfABwLg, Jul. 12, 2015, 2 pages.
Daniel About Tech, "Workout App Full Review! (Apple Watch)", Available Online at https://www.youtube.com/watch?v=aHXCNfSccoY, Feb. 19, 2019, 2 pages.
Notice of Allowance received for Japanese Patent Application No. 2019-222213, dated Aug. 30, 2021, 4 pages (1 page of English Translation and 3 pages of Official Copy).
Office Action received for Australian Patent Application No. 2021203301, dated Nov. 3, 2021, 3 pages.
Office Action received for Korean Patent Application No. 10-2021-7015702, dated Jun. 19, 2021, 12 pages (6 pages of English Translation and 6 pages of Official Copy).
Notice of Acceptance received for Australian Patent Application No. 2021203301, dated Feb. 23, 2022, 3 pages.
Advisory Action received for U.S. Appl. No. 15/372,133, dated Aug. 28, 2019, 7 pages.
Advisory Action received for U.S. Appl. No. 15/372,133, dated Jun. 2, 2020, 5 pages.
Apple Inc., "iPhone User Guide For iOS 7.1 Software", available online at <https://manuals.info.apple.com/MANUALS/1000/MA1681/en US/iphone_ios7_user_guide.pdf>, Mar. 10, 2014, pp. 1-162.
Applicant-Initiated Interview Summary received for U.S. Appl. No. 15/372,133, dated Dec. 23, 2019, 6 pages.
Applicant-Initiated Interview Summary received for U.S. Appl. No. 15/372,133, dated May 4, 2020, 5 pages.
Applicant-Initiated Interview Summary received for U.S. Appl. No. 15/372,133, dated Nov. 12, 2020, 5 pages.
Benson, Amanda, "Health App of the Month: Move, The Daily Activity Reminder", ThinkHealth, Retrieved from the internet: https://thinkhealth.priorityhealth.com/health-app-of-the-month-move-the-daily-activity-reminder/, Mar. 12, 2015, pp. 1-4.
Breathe Deeply Now! for Windows Phone Version, Online Available at https://www.appx4fun.com/apps/5402/, Feb. 15, 2015, 11 pages.
Decision to Grant received for Danish Patent Application No. PA201770384, dated Jun. 28, 2019, 2 pages.
Extended European Search Report received for European Patent Application No. 17810736.3, dated Nov. 7, 2019, 10 pages.
Final Office Action received for U.S. Appl. No. 14/599,425, dated May 19, 2017, 24 pages.
Final Office Action received for U.S. Appl. No. 14/599,425, dated Oct. 8, 2015, 20 pages.
Final Office Action received for U.S. Appl. No. 15/372,133, dated Apr. 6, 2020, 16 pages.
Final Office Action received for U.S. Appl. No. 15/372,133, dated Apr. 18, 2019, 14 pages.
Intention to Grant received for Danish Patent Application No. PA201770384, dated Mar. 13, 2019, 2 pages.
Intention to Grant received for Danish Patent Application No. PA201770384, dated Nov. 14, 2018, 2 pages.
International Preliminary Report on Patentability received for PCT Patent Application No. PCT/US2013/073195, dated Jun. 16, 2016, 10 pages.
International Preliminary Report on Patentability received for PCT Patent Application No. PCT/US2015/032474, dated Dec. 15, 2016, 7 pages.
International Preliminary Report on Patentability received for PCT Patent Application No. PCT/US2017/035309, dated Dec. 20, 2018, 28 pages.
International Search Report and Written Opinion received for PCT Patent Application No. PCT/US2015/032474, dated Aug. 19, 2015, 8 pages.
International Search Report and Written Opinion received for PCT Patent Application No. PCT/US2017/035309, dated Sep. 27, 2017, 31 pages.
International Search Report received for PCT Patent Application No. PCT/US2013/073195, dated Jun. 23, 2014, 3 pages.
International Written Opinion received for PCT Patent Application No. PCT/US2013/073195, dated Jun. 23, 2014, 8 pages.
Invitation to Pay Additional Fee received for PCT Patent Application No. PCT/US2017/035309, dated Jul. 14, 2017, 2 pages.
Non-Final Office Action received for U.S. Appl. No. 14/503,372, dated Dec. 5, 2014, 11 pages.
Non-Final Office Action received for U.S. Appl. No. 14/599,425, dated Mar. 17, 2015, 16 pages.
Non-Final Office Action received for U.S. Appl. No. 14/599,425, dated Oct. 26, 2016, 22 pages.
Non-Final Office Action received for U.S. Appl. No. 15/372,133, dated Jul. 24, 2018, 13 pages.
Non-Final Office Action received for U.S. Appl. No. 15/372,133, dated Oct. 3, 2019, 14 pages.
Non-Final Office Action received for U.S. Appl. No. 15/372,133, dated Sep. 14, 2020, 17 pages.
Notice of Acceptance received for Australian Patent Application No. 2017277848, dated Apr. 20, 2020, 3 pages.
Notice of Acceptance received for Australian Patent Application No. 2020203453, dated Feb. 10, 2021, 3 pages.
Notice of Allowance received for Chinese Patent Application No. 201520358505.5, dated Jan. 13, 2016, 3 pages.
Notice of Allowance received for Chinese Patent Application No. 201710400594.9, dated Jul. 30, 2020, 2 pages.
Notice of Allowance received for Japanese Patent Application No. 2018-563158, dated Nov. 8, 2019, 4 pages.
Notice of Allowance received for Korean Patent Application No. 10-2018-7034689, dated Mar. 27, 2020, 6 pages.
Notice of Allowance received for Taiwanese Patent Application No. 104117509, dated Mar. 31, 2017, 3 pages.
Notice of Allowance received for U.S. Appl. No. 15/372,133, dated Feb. 11, 2021, 8 pages.
Notice of Allowance received for U.S. Appl. No. 15/372,133, dated Feb. 26, 2021, 3 pages.
Office Action received for Australian Patent Application No. 2015100734, dated Jul. 29, 2015, 5 pages.
Office Action received for Australian Patent Application No. 2015267240, dated Apr. 10, 2017, 5 pages.
Office Action received for Australian Patent Application No. 2017277848, dated Aug. 28, 2019, 4 pages.
Office Action received for Australian Patent Application No. 2017277848, dated Jan. 16, 2020, 4 pages.
Office Action received for Australian Patent Application No. 2017277848, dated Jun. 13, 2019, 4 pages.
Office Action received for Australian Patent Application No. 2017277848, dated Mar. 4, 2020, 3 pages.
Office Action received for Australian Patent Application No. 2017277848, dated Nov. 1, 2019, 4 pages.
Office Action received for Australian Patent Application No. 2020203453, dated Aug. 12, 2020, 4 pages.
Office Action received for Australian Patent Application No. 2020203453, dated Dec. 18, 2020, 4 pages.
Office Action received for Australian Patent Application No. 2020203453, dated Oct. 29, 2020, 4 pages.
Office Action received for Chinese Patent Application No. 201710400594.9, dated Apr. 23, 2018, 3 pages.

(56) References Cited

OTHER PUBLICATIONS

Office Action received for Chinese Patent Application No. 201710400594.9, dated Jul. 17, 2017, 2 pages.
Office Action received for Chinese Patent Application No. 201710400594.9, dated Mar. 20, 2020, 6 pages.
Office Action received for Chinese Patent Application No. 201710400594.9, dated May 14, 2019, 14 pages.
Office Action received for Chinese Patent Application No. 201710400594.9, dated Nov. 15, 2019, 12 pages.
Office Action received for Danish Patent Application No. PA201770384, dated Oct. 27, 2017, 7 pages.
Office Action received for European Patent Application No. 15730890.9, dated Aug. 3, 2017, 4 pages.
Office Action received for European Patent Application No. 17810736.3, dated Nov. 11, 2020, 6 pages.
Office Action received for Japanese Patent Application No. 2016-535045, dated May 12, 2017, 10 pages.
Office Action received for Japanese Patent Application No. 2019-222213, dated Jan. 4, 2021, 9 pages.
Office Action received for Korean Patent Application No. 10-2018-7034689, dated Nov. 28, 2019, 11 pages.
Office Action received for Taiwanese Patent Application No. 104117509, dated Aug. 22, 2016, 6 pages.
Paced Breathing, "How to use Paced Breathing", Retrieved from https://pacedbreathing.blogspot.com/2014/03/how-to-use-paced-breathing.html on Sep. 9, 2020, Apr. 3, 2015, 7 pages.
Stachowiak, Sandy, "Relax, breathe deep and regain focus with Hear and Now", Available online at: https://appadvice.com/appnn/2016/01/relax-breathe-deep-and-regain-focus-with-hear-and-now, Jan. 6, 2016, 3 pages.
Supplemental Notice of Allowance received for U.S. Appl. No. 15/372,133, dated Mar. 26, 2021, 3 pages.
Tiles and Toasts, "Toast Notification and Action Center Overview for Windows 10", Online Available at: https://blogs.msdn.microsoft.com/tiles_and_toasts/2015/07/08/toast-notification-and-action-center-overview-for-windows-10/. Published on Jul. 8, 2015, 9 pages.
Time Out app, "Release Notes". Online Available at: www.dejal.com/timeout/release, 2016, 8 pages.
Time Out app, Screens shots and user guide. Online Available at https://web.archive.org/web/20160314023701/http://www.dejal.com/timeout/images/, Mar. 14, 2016, 10 pages.
Windowsunited, "Breathe Deeply Now! Please Take a Deep Breath and Relax", Online Available at: https://windowsunited.de/breathe-deeply-now-die-app-gegen-angszustaende/, Published on Oct. 4, 2014, 8 pages.
Office Action received for Japanese Patent Application No. 2021-159616, dated Dec. 5, 2022, 11 pages (6 pages of English Translation and 5 pages of Official Copy).
Notice of Allowance received for Korean Patent Application No. 10-2022-7010343, dated Feb. 27, 2023, 6 pages (2 pages of English Translation and 4 pages of Official Copy).

* cited by examiner

792
(E)
↓

7100
In response to detecting completion of the portion of the selected number of cycles, change the second variable visual characteristic of the progress indicator.

7102
Wherein the first version of the progress indicator comprises a plurality of graphical elements, and wherein changing the second variable visual characteristic of the progress indicator comprises changing a number of the displayed graphical elements of the plurality of graphical elements.

7104
Wherein the device includes a haptic output device, and during the breathing phase of the breathing sequence, output one or more haptic breathing cues according to a haptic profile.

7106
Wherein outputting the one or more haptic breathing cues according to the haptic profile comprises:

7108
Output, at the start of the first period of time, a first number of haptic breathing cues.

↓

7110
Output, at the start of the second period of time, a second number of haptic breathing cues, wherein the first number and the second number are different.

7148
Determine an aggregate amount of time representing a completed number of cycles of the breathing sequence over a goal period.

7150
Wherein the first version of the progress indicator fluctuates at a first cyclic rate, and wherein the aggregate amount of time is determined based at least in part on the first cyclic rate.

7152
Wherein the goal period is the current day.

7154
In response to detecting completion of the breathing phase of the breathing sequence, display, on the display, a completion interface comprising: an indication of the aggregate amount of time, and a third affordance.

7156
Wherein detecting completion of the breathing phase comprises detecting that a predetermined amount of time has elapsed.

7158
Wherein the completion interface further comprises an indication of an estimated heart rate.

7160
Receive user input selection of the third affordance.

7162
In response to receiving the user input selection of the third affordance, progress to the breathing phase of the breathing sequence.

*FIG. 7J*

7164
Determine an aggregate amount of time representing a completed number of cycles of the breathing sequence over a goal period for each of a plurality of goal periods.

7166
Wherein the goal period is a day and the plurality of goal periods is seven days.

7168
Display, on the display, a summary interface comprising an indicator for each of the plurality of goal periods, wherein the indicator for each of the plurality of goal periods represents the determined aggregate amount of time for its respective goal period of the plurality of goal periods.

7170
Receive a second signal during the breathing sequence.

7172
Wherein the device includes a sensor, and wherein receiving the second signal comprises receiving the second signal from the sensor during the breathing sequence.

7174
Determine an estimated breathing pattern based at least in part on the received second signal.

7176
Synchronize the initiation of the breathing phase of the breathing sequence and the display of the progress indicator during the breathing phase of the breathing sequence with the estimated breathing pattern.

7178
Wherein synchronizing the initiation of the breathing phase of the breathing sequence and the display of the progress indicator during the breathing phase of the breathing sequence with the estimated breathing pattern comprises:

7180
Determine a synchronization event that is a transition between an inhale period and an exhale period of the estimated breathing pattern.

| FIRST BREATHING SEQUENCE INITIATION TIME | FIRST BREATHING SEQUENCE COMPLETION TIME | PROMPTING FREQUENCY | PROMPT DISPLAY TIME |
|---|---|---|---|
| 7:57 AM | 8:00 AM | 2 | 9:57 AM - 10:00 AM |
| 7:57 AM | 8:00 AM | 4 | 11:57 AM - 12:00 PM |
| 7:57 AM | 8:00 AM | 6 | 1:57 PM - 2:00 PM |
| 7:57 AM | 8:00 AM | 8 | 3:57 PM - 4:00 PM |
| 7:57 AM | 8:00 AM | 10 | 5:57 PM - 6:00 PM |
| 7:57 AM | 8:00 AM | 12 | 7:57 PM - 8:00 PM |

*FIG. 9B*

BREATHING SEQUENCE USER INTERFACE

CROSS-REFERENCE TO RELATED APPLICATIONS

This application is a continuation of U.S. patent application Ser. No. 15/372,133, entitled "BREATHING SEQUENCE USER INTERFACE", filed on Dec. 7, 2016, which claims priority to U.S. Provisional Application Ser. No. 62/348,844, entitled "BREATHING SEQUENCE USER INTERFACE", filed on Jun. 10, 2016, the content of which is hereby incorporated by reference in its entirety.

This application also relates to the following applications: U.S. Provisional Application Ser. No. 62/348,804, entitled "Breathing Synchronization and Monitoring", filed on Jun. 10, 2016; and U.S. Provisional Application Ser. No. 62/348,808, entitled "Fluctuating Progress Indicator", filed on Jun. 10, 2016.

FIELD

The present disclosure relates generally to computer user interfaces, and more specifically to user interfaces for conducting breathing sequences.

BACKGROUND

More people than ever are experiencing and reporting elevated levels of stress. Elevated levels of stress have been linked to an increase in risk factors for heart disease, heart attack, stroke, poor sleep, and unhealthy diet. It is estimated that over half of all health ailments derive from elevated levels of stress. Furthermore, studies have shown that individuals are working longer hours on average, compared to previous generations, and participate in lesser amounts of stress-reducing activities, such as physical exercise, leisure time, hobbies, and vacation. The entrenchment of poor habits and development of health ailments can serve to cause an individual to experience further stress and anxiety. Thus, the cycle of stress and its resulting effects can be difficult to manage well, though it is essential to do so. Recent studies have found that performing conscious breathing exercises can be effective against stress, and can lower blood pressure and heart rate, increase cardiovascular health, and make an individual feel more calm and relaxed. It is therefore desirable to facilitate the regular performance of breathing exercises and thereby reduce stress levels.

BRIEF SUMMARY

The present disclosure relates to systems and processes for conducting and generating notifications for breathing sequences on an electronic device, and for generating user interfaces for displaying the same. Some techniques for guiding a user breathing exercise are ineffective. For example, some existing techniques use a complex and time-consuming user interface, which may include multiple key presses or keystrokes. Existing techniques require more time than necessary, wasting user time and device energy. This latter consideration is particularly important in battery-operated devices. Furthermore, the use of complex and unintuitive user interfaces may frustrate the user, and thus create the undesirable effects of increasing a user's stress level or causing the user to forgo performing a breathing exercise due to time or frustration.

Accordingly, the present technique provides electronic devices with faster, more efficient methods and interfaces for conducting breathing sequences to guide and train a user's breathing while performing a breathing exercise. Such methods and interfaces optionally complement or replace other methods for conducting breathing sequences. Such methods and interfaces reduce the cognitive burden on a user and produce a more efficient human-machine interface. For battery-operated computing devices, such methods and interfaces conserve power and increase the time between battery charges. For example, intuitive interfaces for configuring and conducting breathing sequences reduces the number of unnecessary, extraneous, or repetitive inputs received by the device, resulting in reduced battery usage by the display and one or more processors.

In some embodiments, a computer-implemented method is performed, the method comprising: at a device with a display: displaying, on the display, a configuration user interface, wherein the configuration user interface comprises a prompt to select a number of cycles of a breathing sequence; receiving a first user input; in response to receiving the first user input, adjusting the number of cycles of the breathing sequence to the selected number of cycles; initiating a breathing phase of the breathing sequence; and during the breathing phase of the breathing sequence: displaying, on the display, a first version of a progress indicator; and fluctuating the first version of the progress indicator in accordance with the selected number of cycles.

In some embodiments, an electronic device comprises: a display; one or more processors; memory; and one or more programs, wherein the one or more programs are stored in the memory and configured to be executed by the one or more processors, the one or more programs including instructions for: displaying, on the display, a configuration user interface, wherein the configuration user interface comprises a prompt to select a number of cycles of a breathing sequence; receiving a first user input; in response to receiving the first user input, adjusting the number of cycles of the breathing sequence to the selected number of cycles; initiating a breathing phase of the breathing sequence; and during the breathing phase of the breathing sequence: displaying, on the display, a first version of a progress indicator; and fluctuating the first version of the progress indicator in accordance with the selected number of cycles.

In some embodiments, a non-transitory computer-readable storage medium stores one or more programs, the one or more programs comprising instructions, which, when executed by an electronic device with a display, cause the device to: display, on the display, a configuration user interface, wherein the configuration user interface comprises a prompt to select a number of cycles of a breathing sequence; receive a first user input; in response to receiving the first user input, adjust the number of cycles of the breathing sequence to the selected number of cycles; initiate a breathing phase of the breathing sequence; and during the breathing phase of the breathing sequence: display, on the display, a first version of a progress indicator; and fluctuate the first version of the progress indicator in accordance with the selected number of cycles.

In some embodiments, a transitory computer-readable storage medium stores one or more programs, the one or more programs comprising instructions, which, when executed by an electronic device with a display, cause the device to: display, on the display, a configuration user interface, wherein the configuration user interface comprises a prompt to select a number of cycles of a breathing sequence; receive a first user input; in response to receiving the first user input, adjust the number of cycles of the breathing sequence to the selected number of cycles; initiate a breathing phase of the breathing sequence; and during the breathing phase of the breathing sequence: display, on the display, a first version of a progress indicator; and fluctuate the first version of the progress indicator in accordance with the selected number of cycles.

In some embodiments, a system comprises: a display; means for displaying, on the display, a configuration user interface, wherein the configuration user interface comprises a prompt to select a number of cycles of a breathing sequence; means for receiving a first user input; means, responsive to receiving the first user input, for adjusting the number of cycles of the breathing sequence to the selected number of cycles; means for initiating a breathing phase of the breathing sequence; and means for, during the breathing phase of the breathing sequence: displaying, on the display, a first version of a progress indicator; and fluctuating the first version of the progress indicator in accordance with the selected number of cycles.

In some embodiments, a device comprises: a display unit; and a processing unit coupled to the display unit, the processing unit comprising: a display enabling unit configured to enable display of, on the display unit, a configuration user interface, wherein the configuration user interface comprises a prompt to select a number of cycles of a breathing sequence; a receiving unit configured to receive a first user input; an adjusting unit configured to, in response to receiving the first user input, adjust the number of cycles of the breathing sequence to the selected number of cycles; an initiating unit configured to initiate a breathing phase of the breathing sequence; and during the breathing phase of the breathing sequence: wherein the display enabling unit is further configured to enable display of, on the display unit, a first version of a progress indicator; and a fluctuating unit configured to fluctuate the first version of the progress indicator in accordance with the selected number of cycles.

In some embodiments, a computer-implemented method is performed, the method comprising: at an electronic device with a display: detecting a time associated with a first breathing sequence; generating a prompting criteria based on a predetermined prompting frequency and the detected time associated with the first breathing sequence; determining if the prompting criteria has been met; in accordance with a determination that the prompting criteria has been met, displaying, on the display, a prompt to initiate a second breathing sequence, wherein the prompt comprises a first affordance; receiving user input selection of the first affordance; and in response to receiving the user input selection of the first affordance, displaying, on the display, a second breathing sequence user interface.

In some embodiments, an electronic device comprises: a display; one or more processors; memory; and one or more programs, wherein the one or more programs are stored in the memory and configured to be executed by the one or more processors, the one or more programs including instructions for: detecting a time associated with a first breathing sequence; generating a prompting criteria based on a predetermined prompting frequency and the detected time associated with the first breathing sequence; determining if the prompting criteria has been met; in accordance with a determination that the prompting criteria has been met, displaying, on the display, a prompt to initiate a second breathing sequence, wherein the prompt comprises a first affordance; receiving user input selection of the first affordance; and in response to receiving the user input selection of the first affordance, displaying, on the display, a second breathing sequence user interface.

In some embodiments, a non-transitory computer-readable storage medium stores one or more programs, the one or more programs comprising instructions, which, when executed by an electronic device with a display, cause the device to: detect a time associated with a first breathing sequence; generate a prompting criteria based on a predetermined prompting frequency and the detected time associated with the first breathing sequence; determine if the prompting criteria has been met; in accordance with a determination that the prompting criteria has been met, display, on the display, a prompt to initiate a second breathing sequence, wherein the prompt comprises a first affordance; receive user input selection of the first affordance; and in response to receiving the user input selection of the first affordance, display, on the display, a second breathing sequence user interface.

In some embodiments, a transitory computer-readable storage medium stores one or more programs, the one or more programs comprising instructions, which, when executed by an electronic device with a display, cause the device to: detect a time associated with a first breathing sequence; generate a prompting criteria based on a predetermined prompting frequency and the detected time associated with the first breathing sequence; determine if the prompting criteria has been met; in accordance with a determination that the prompting criteria has been met, display, on the display, a prompt to initiate a second breathing sequence, wherein the prompt comprises a first affordance; receive user input selection of the first affordance; and in response to receiving the user input selection of the first affordance, display, on the display, a second breathing sequence user interface.

In some embodiments, a system comprises: a display; means for detecting a time associated with a first breathing sequence; means for generating a prompting criteria based on a predetermined prompting frequency and the detected time associated with the first breathing sequence; means for determining if the prompting criteria has been met; means for, in accordance with a determination that the prompting criteria has been met, displaying, on the display, a prompt to initiate a second breathing sequence, wherein the prompt comprises a first affordance; means for receiving user input selection of the first affordance; and means, responsive to receiving the user input selection of the first affordance, for displaying, on the display, a second breathing sequence user interface.

In some embodiments, a device comprises: a display unit; and a processing unit coupled to the display unit, the processing unit comprising: a detecting unit configured to detect a time associated with a first breathing sequence; a generating unit configured to generate a prompting criteria based on a predetermined prompting frequency and the detected time associated with the first breathing sequence; a determining unit configured to determine if the prompting criteria has been met; a display enabling unit configured to, in accordance with a determination that the prompting criteria has been met, enable display of, on the display unit, a prompt to initiate a second breathing sequence, wherein the prompt comprises a first affordance; and a receiving unit configured to receive user input selection of the first affordance; and wherein the display enabling unit is further configured to, in response to receiving the user input selection of the first affordance, enable display of, on the display unit, a second breathing sequence user interface.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for conducting breathing sequences, thereby increasing the effectiveness, efficiency, and user satisfaction with such devices. Such methods and interfaces may complement or replace other methods for conducting breathing sequences.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIGS. 7A-7L is a flow diagram illustrating an exemplary process for conducting breathing sequences.

FIGS. 9A-9B illustrate exemplary user interfaces for generating reminders to conduct a breathing sequence.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide intuitive and efficient methods and interfaces for conducting breathing sequences. Such techniques can reduce the cognitive burden on a user who conducts breathing sequences, thereby enhancing the effectiveness of guided breathing exercises. Further, such techniques can reduce processor and battery power otherwise wasted on redundant user inputs.

Figure 9A:
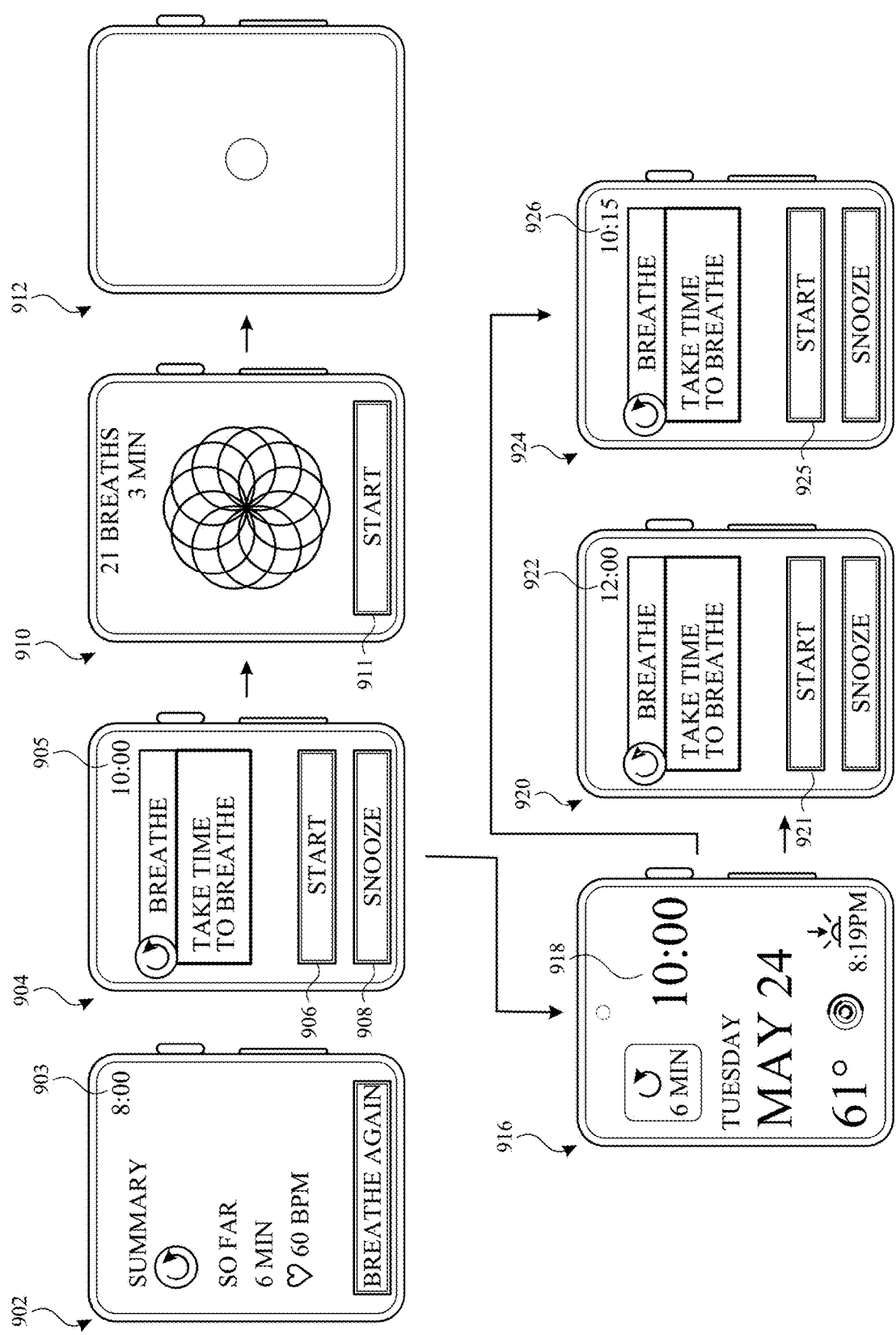
Figure 10A:
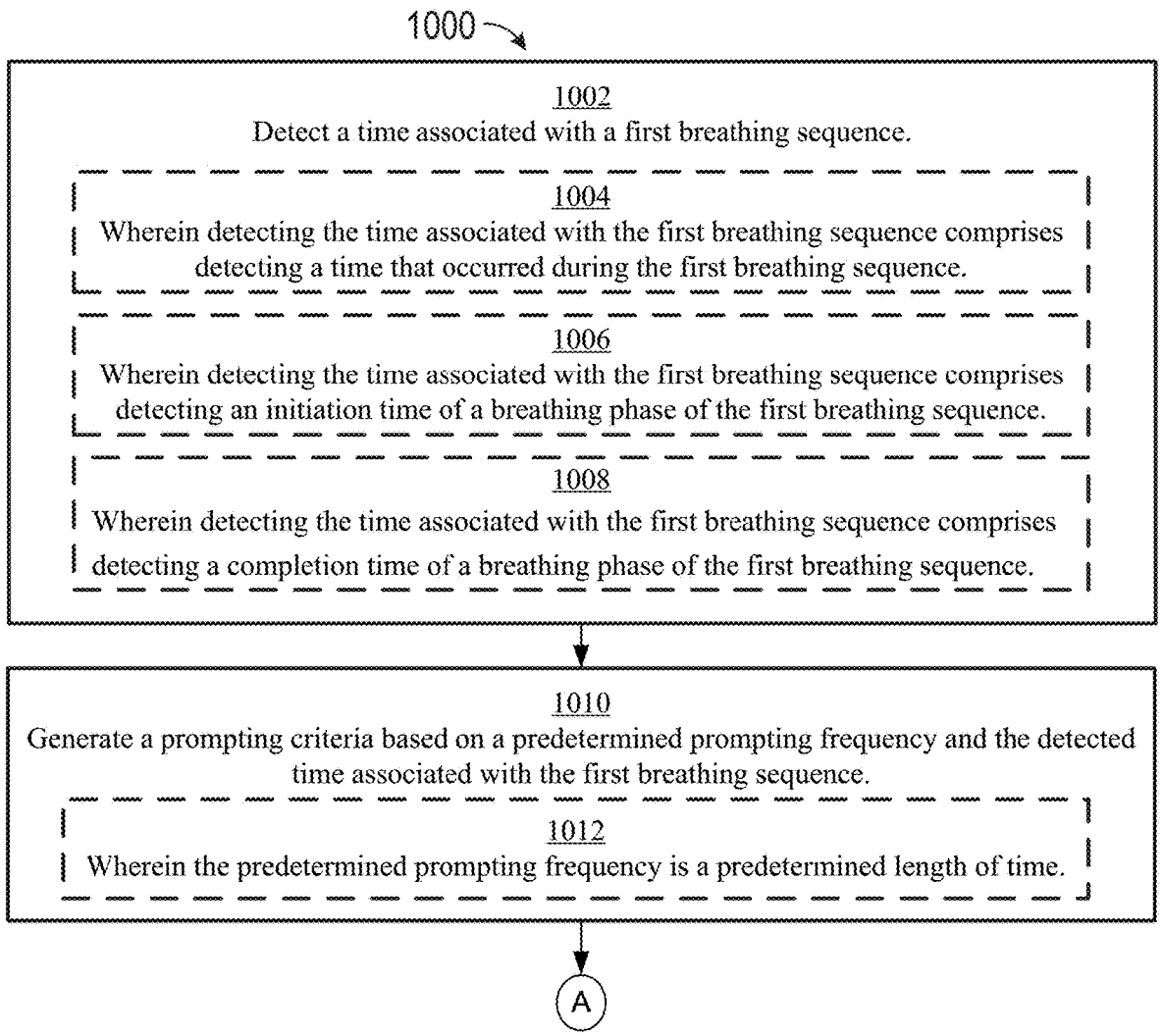
FIGS. 10A-10F is a flow diagram illustrating an exemplary process for generating reminders to conduct a breathing sequence.
Figure 10B:
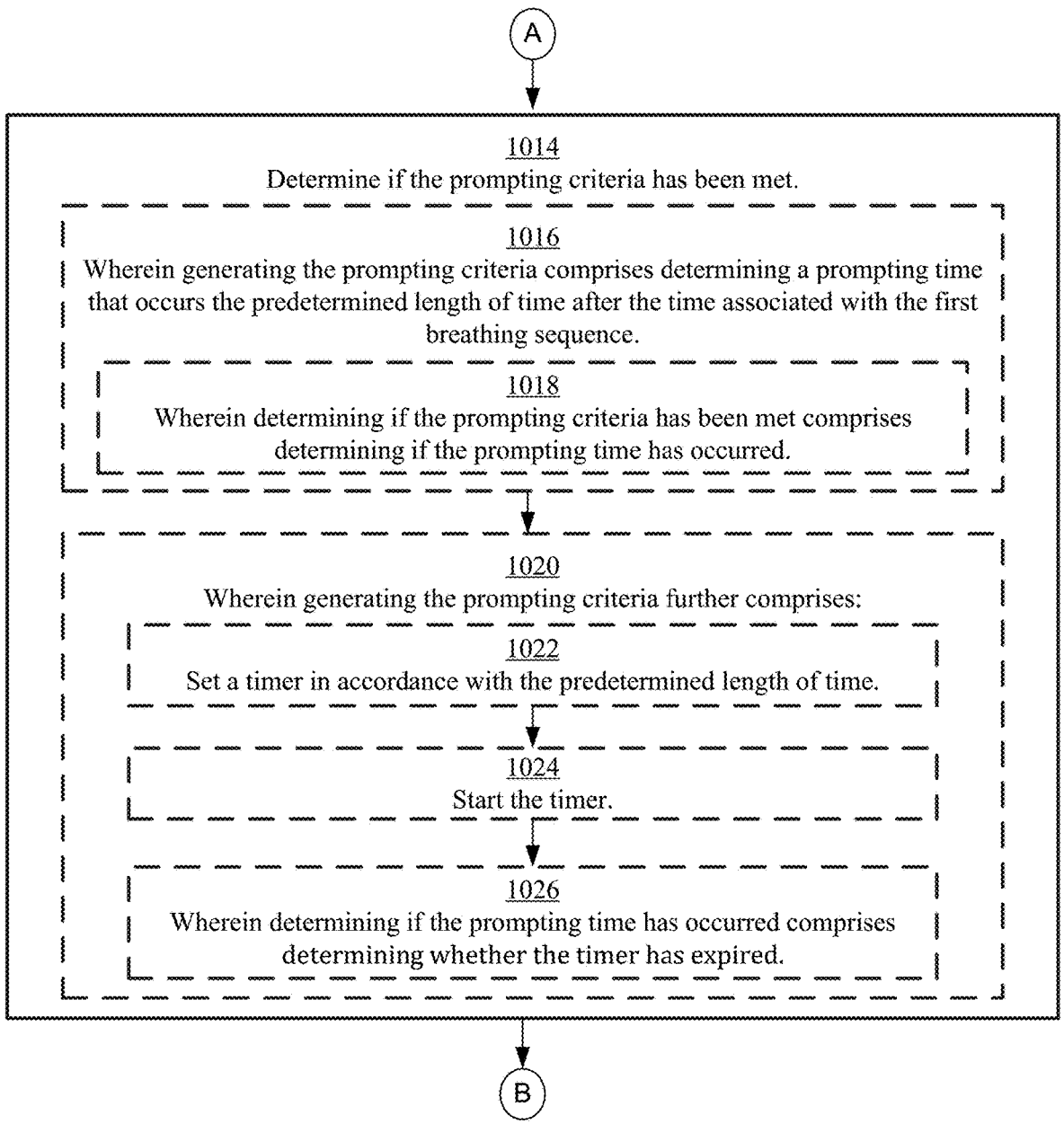
Figure 10C:
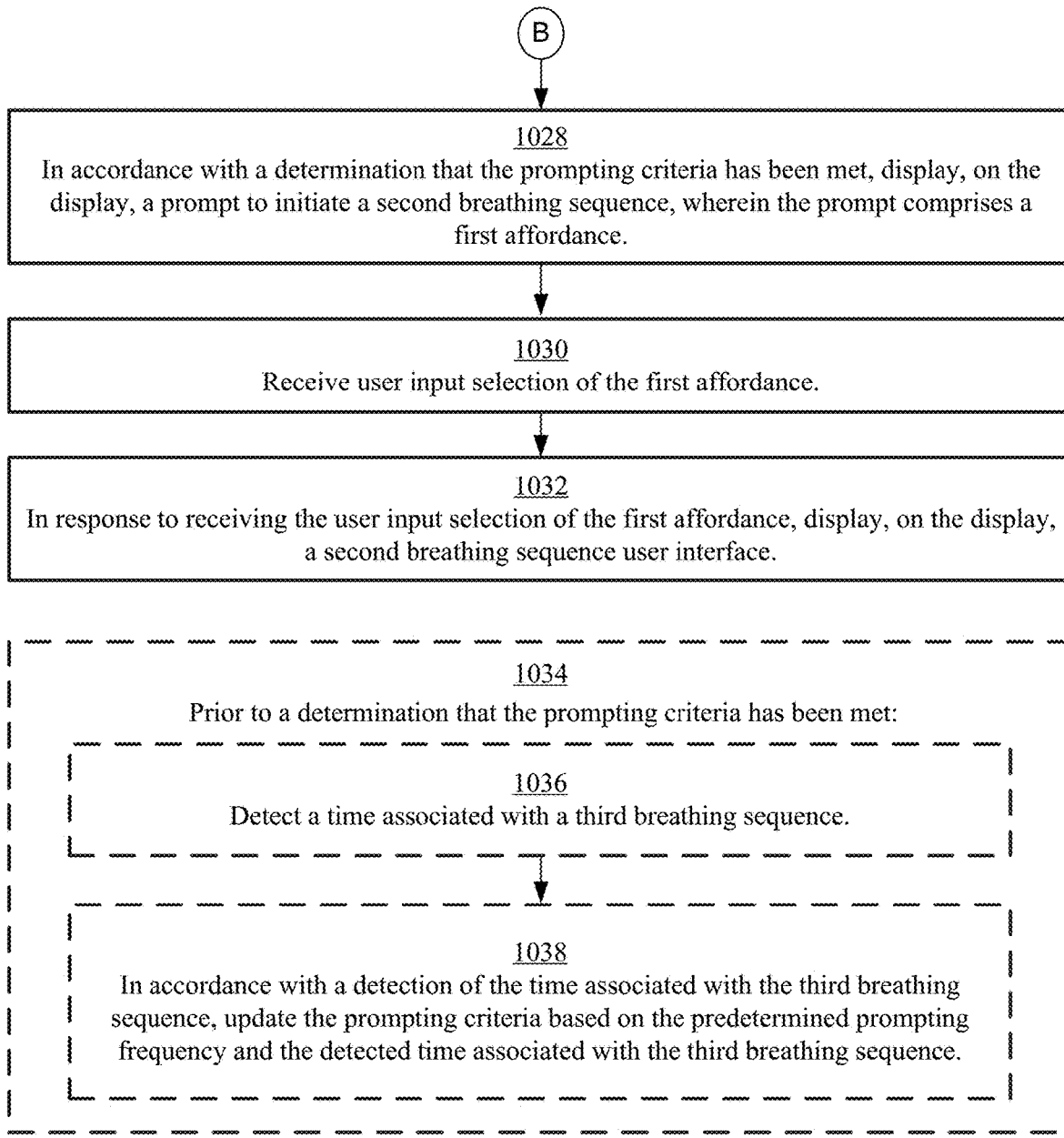
Figure 10D:
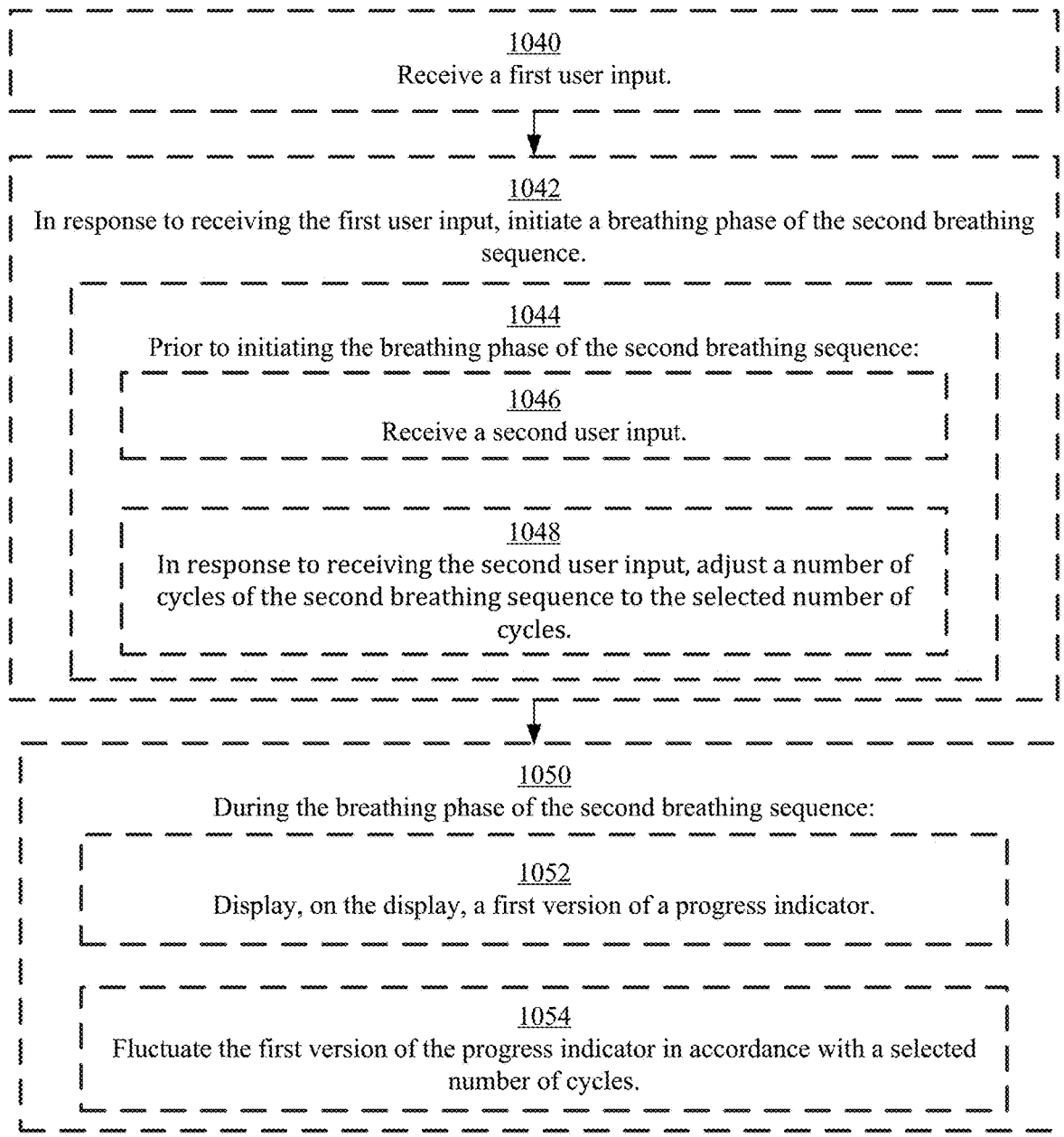
Figure 10E:
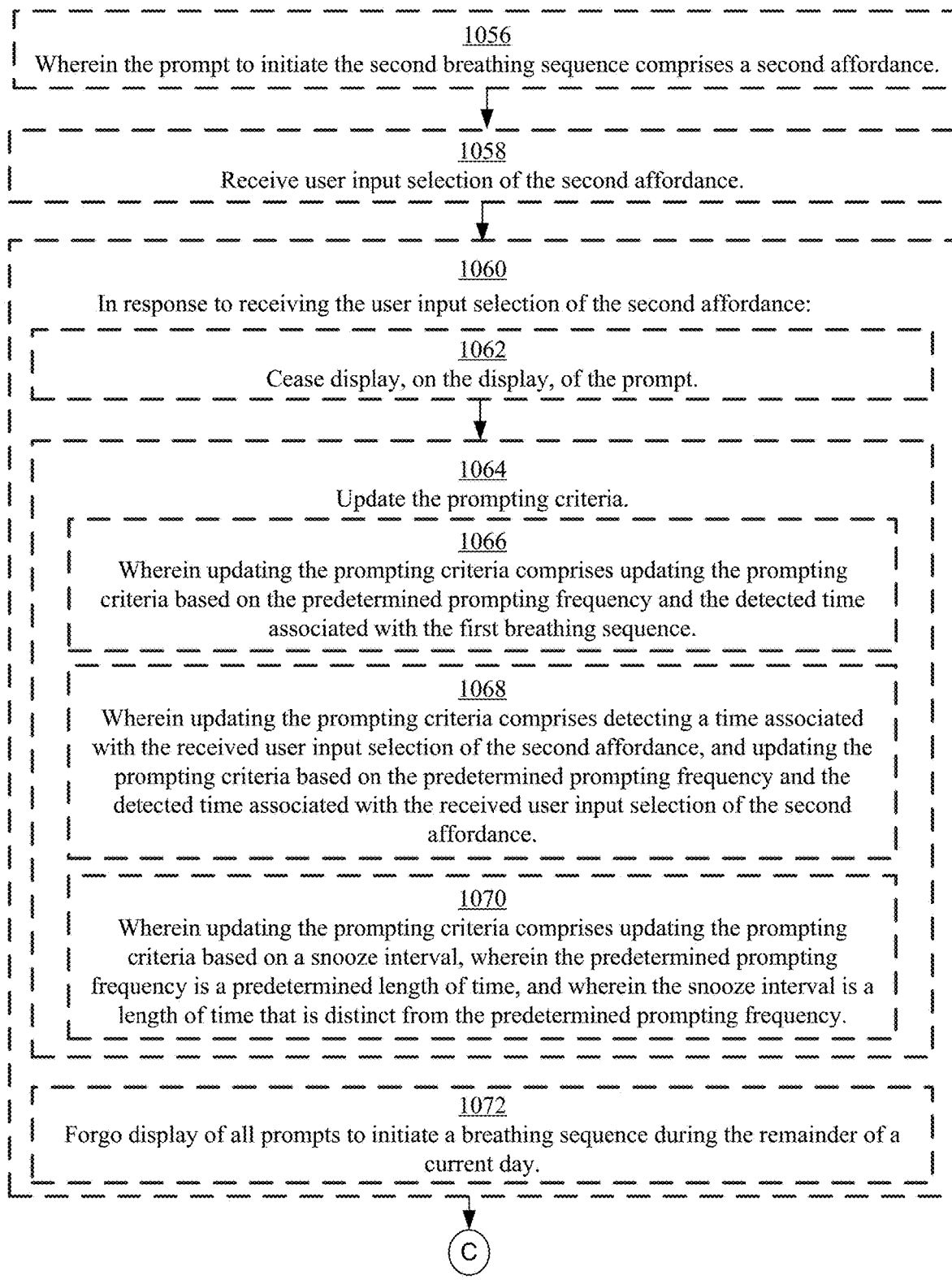
Figure 10F:
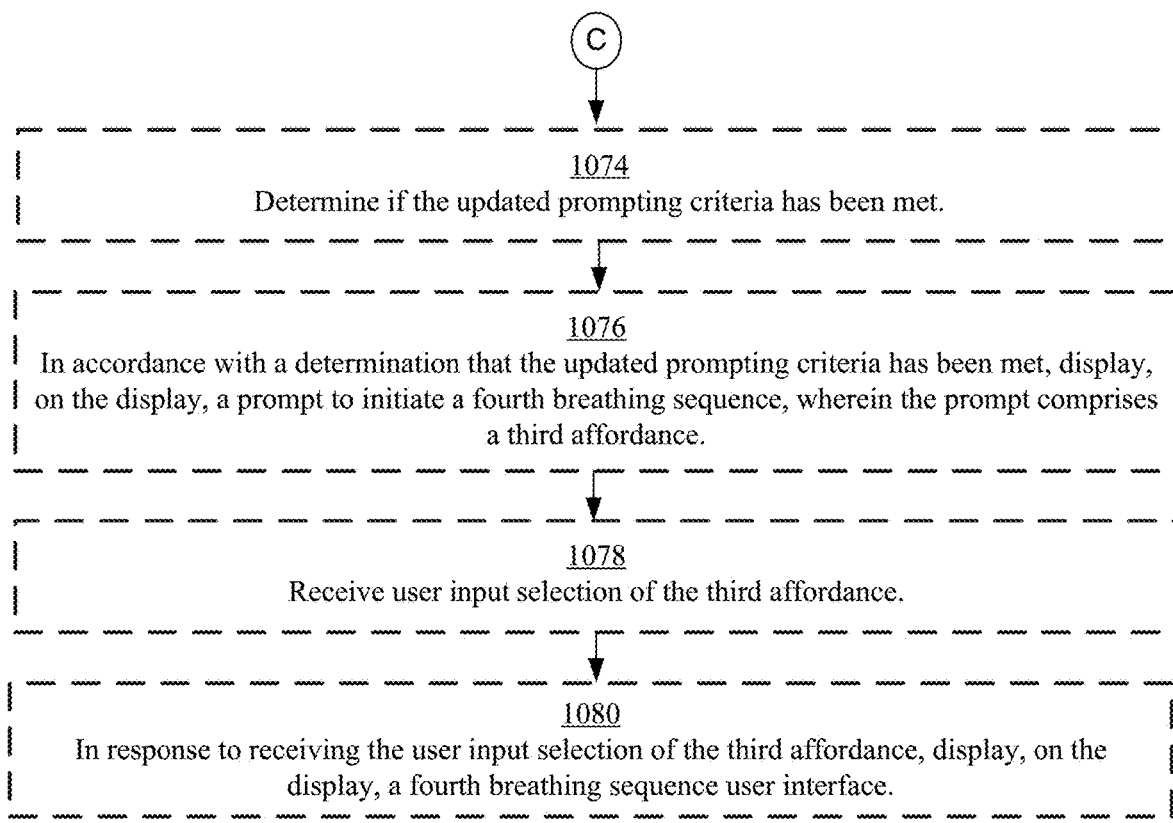

Below, FIGS. 1A-1B, 2, 3, 4A-4B, and 5A-5H provide a description of exemplary devices for performing the techniques for managing event notifications. FIGS. 6A-6F illustrate exemplary user interfaces for conducting breathing sequences. FIGS. 7A-7L is a flow diagram illustrating methods of conducting breathing sequences in accordance with some embodiments. The user interfaces in FIGS. 6A-6F are used to illustrate the processes described below, including the processes in FIGS. 7A-7L. FIGS. 9A-9B illustrate exemplary user interfaces for generating reminders to conduct a breathing sequence. FIGS. 10A-10F is a flow diagram illustrating methods of accessing event notifications in accordance with some embodiments. The user interfaces in FIGS. 9A-9B are used to illustrate the processes described below, including the processes in FIGS. 10A-10F.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, Calif. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad).

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
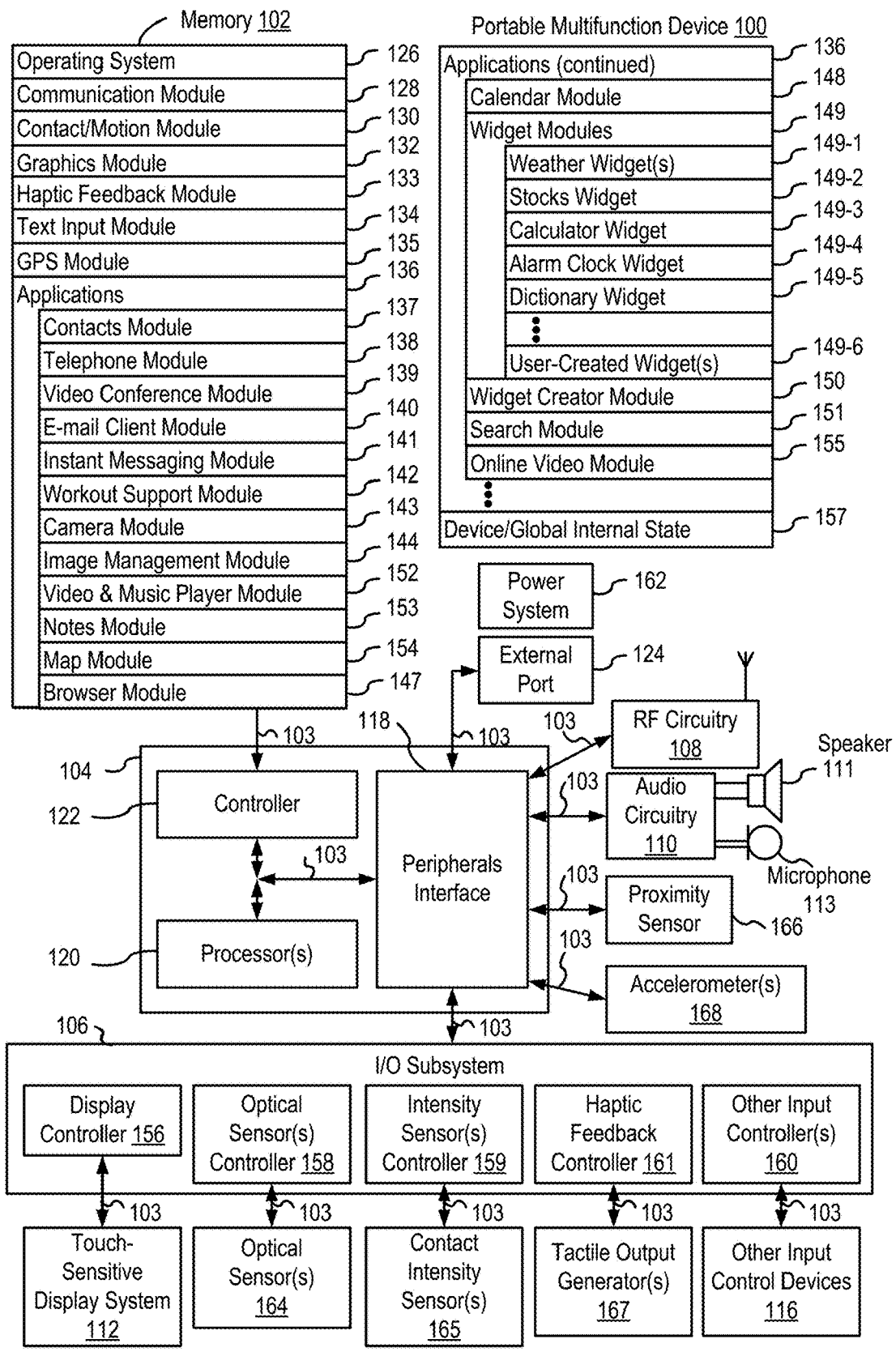
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click,"

"roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, Calif.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad (not shown) for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device";

Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer (not shown) and a GPS (or GLONASS or other global navigation system) receiver (not shown) for obtaining information concerning the location and orientation (e.g., portrait or landscape) of device 100.

Figure 3:
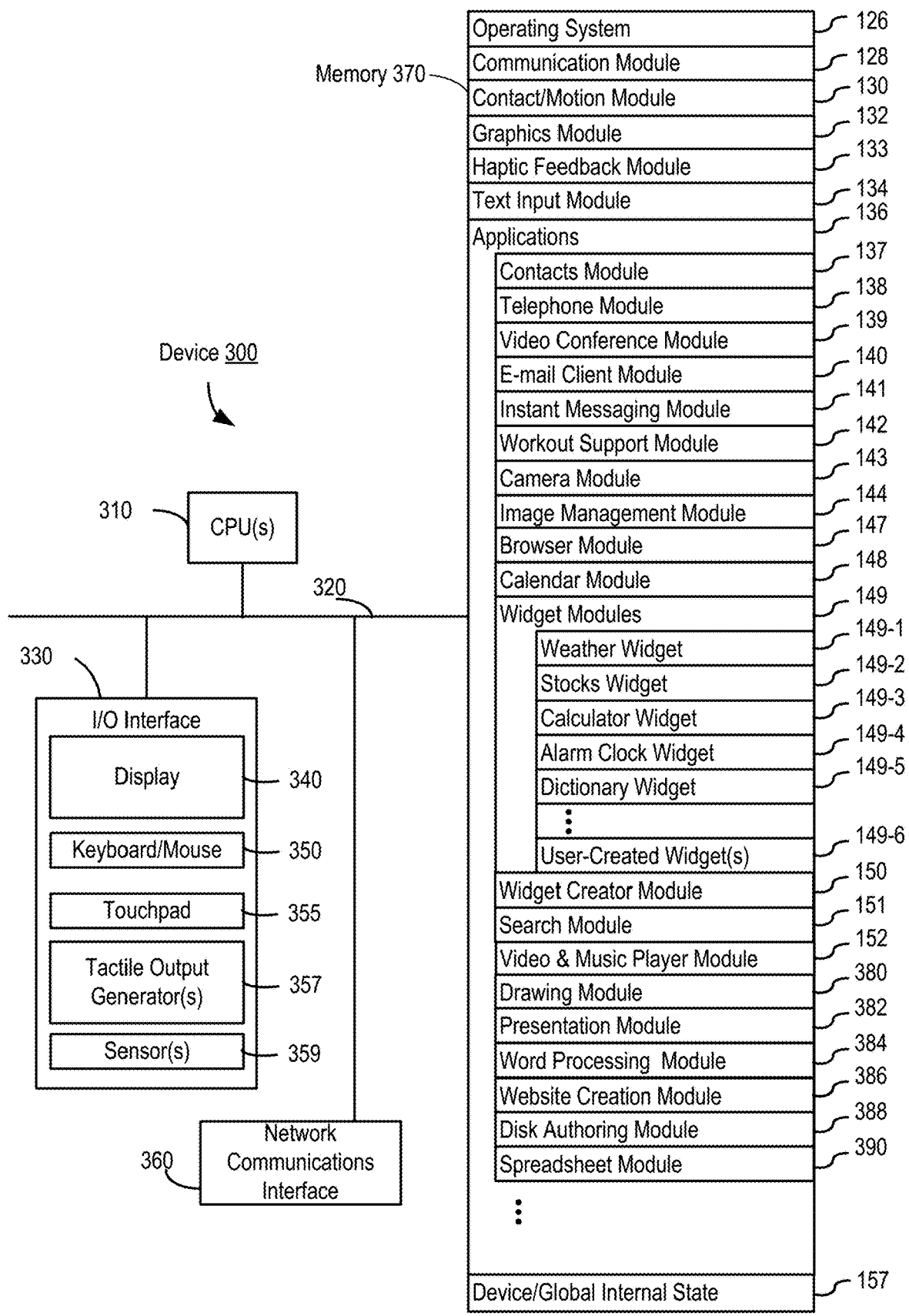
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:
Contacts module 137 (sometimes called an address book or contact list);
Telephone module 138;
Video conference module 139;
E-mail client module 140;
Instant messaging (IM) module 141;
Workout support module 142;
Camera module 143 for still and/or video images;
Image management module 144;
Video player module;
Music player module;
Browser module 147;
Calendar module 148;
Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
Widget creator module 150 for making user-created widgets 149-6;
Search module 151;
Video and music player module 152, which merges video player module and music player module;
Notes module 153;
Map module 154; and/or
Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
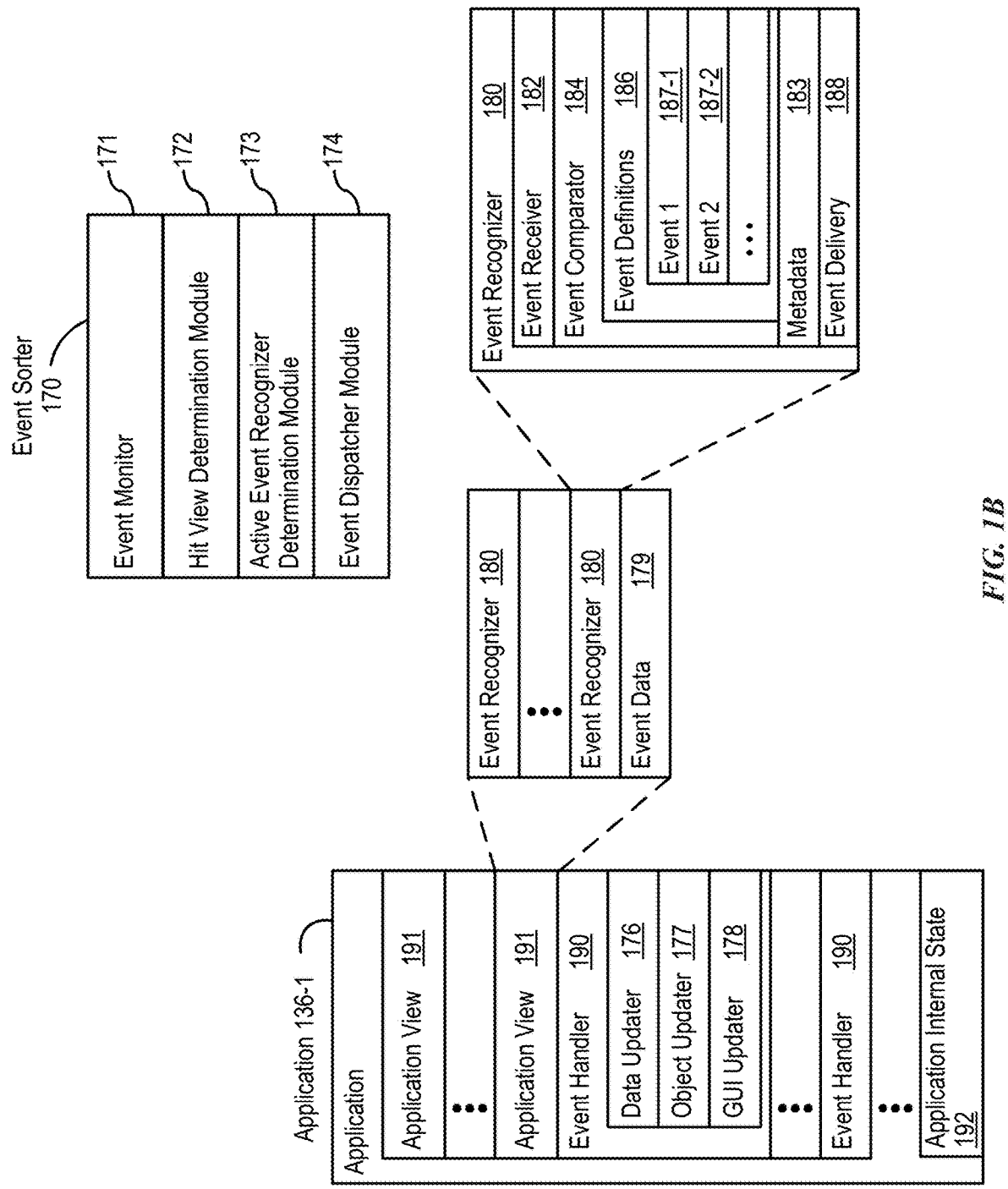
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit (not shown) or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object.

In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
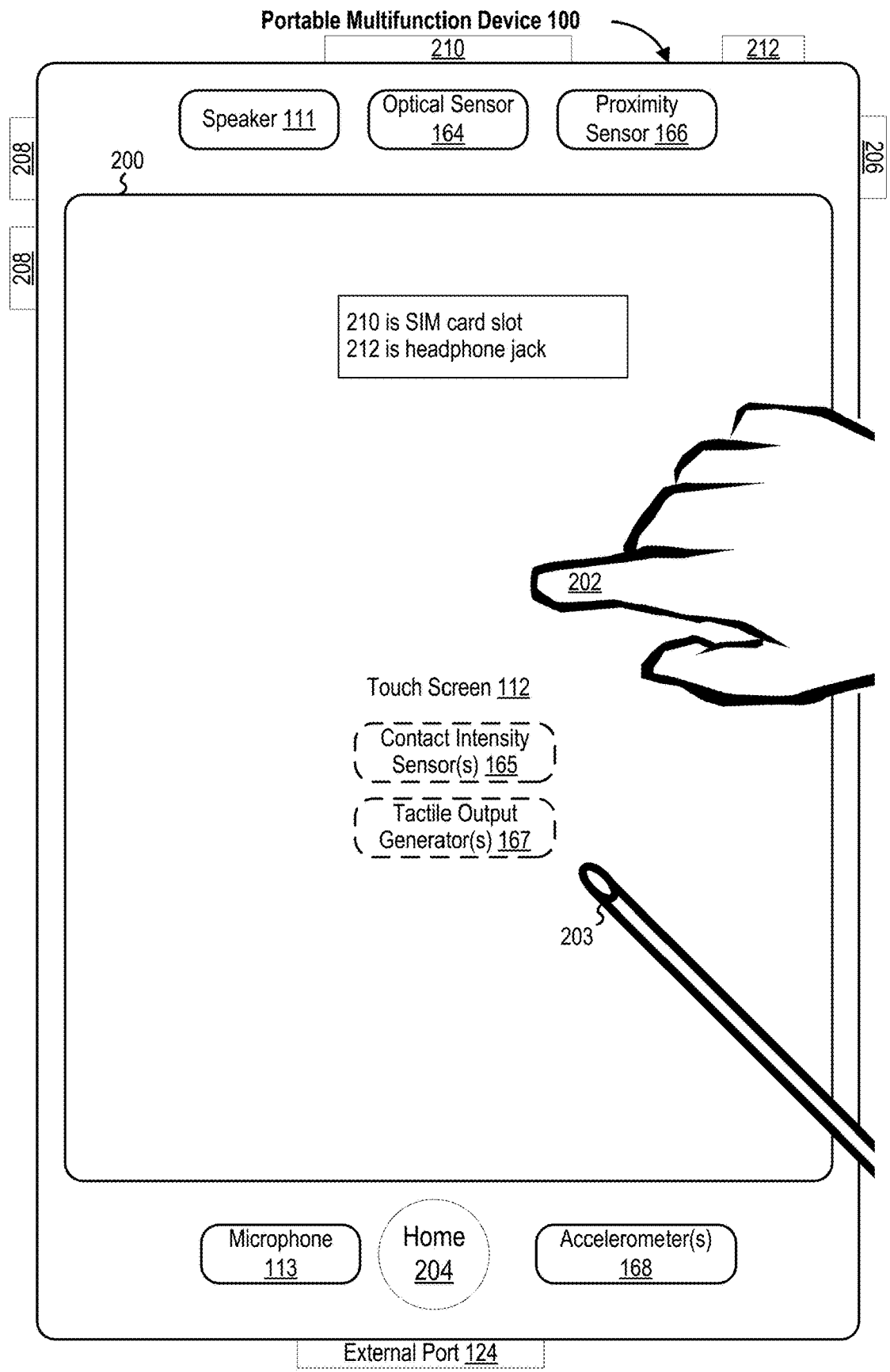
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
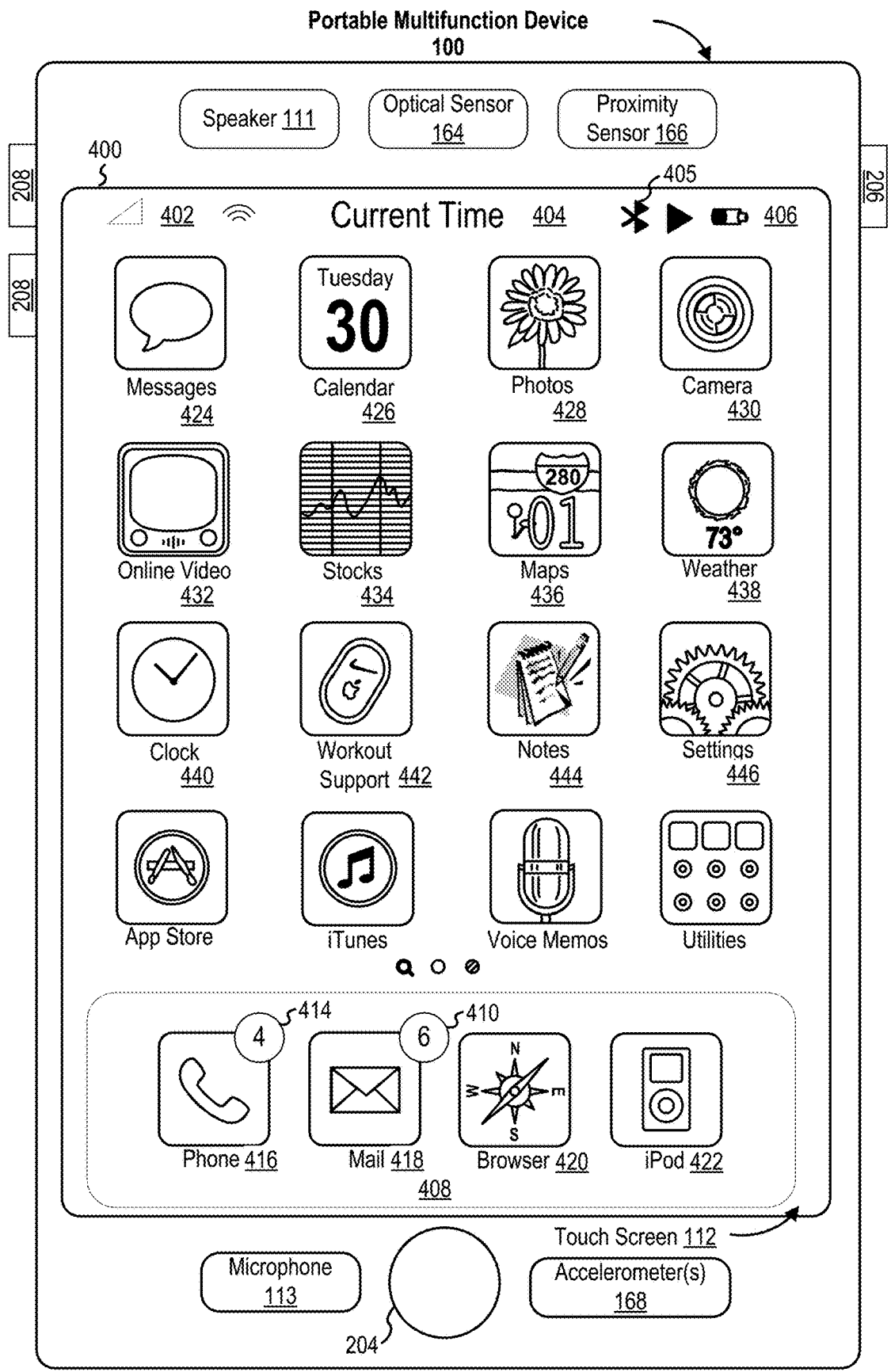
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;

Time 404;

Bluetooth indicator 405;

Battery status indicator 406;

Tray 408 with icons for frequently used applications, such as:

- Icon 416 for telephone module 138, labeled "Phone," which optionally includes an indicator 414 of the number of missed calls or voicemail messages;
- Icon 418 for e-mail client module 140, labeled "Mail," which optionally includes an indicator 410 of the number of unread e-mails;
- Icon 420 for browser module 147, labeled "Browser;" and
- Icon 422 for video and music player module 152, also referred to as iPod (trademark of Apple Inc.) module 152, labeled "iPod;" and Icons for other applications, such as:

- Icon 424 for IM module 141, labeled "Messages;"
- Icon 426 for calendar module 148, labeled "Calendar;"
- Icon 428 for image management module 144, labeled "Photos;"
- Icon 430 for camera module 143, labeled "Camera;"
- Icon 432 for online video module 155, labeled "Online Video;"
- Icon 434 for stocks widget 149-2, labeled "Stocks;"
- Icon 436 for map module 154, labeled "Maps;"
- Icon 438 for weather widget 149-1, labeled "Weather;"
- Icon 440 for alarm clock widget 149-4, labeled "Clock;"
- Icon 442 for workout support module 142, labeled "Workout Support;"
- Icon 444 for notes module 153, labeled "Notes;" and
- Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

Figure 4B:
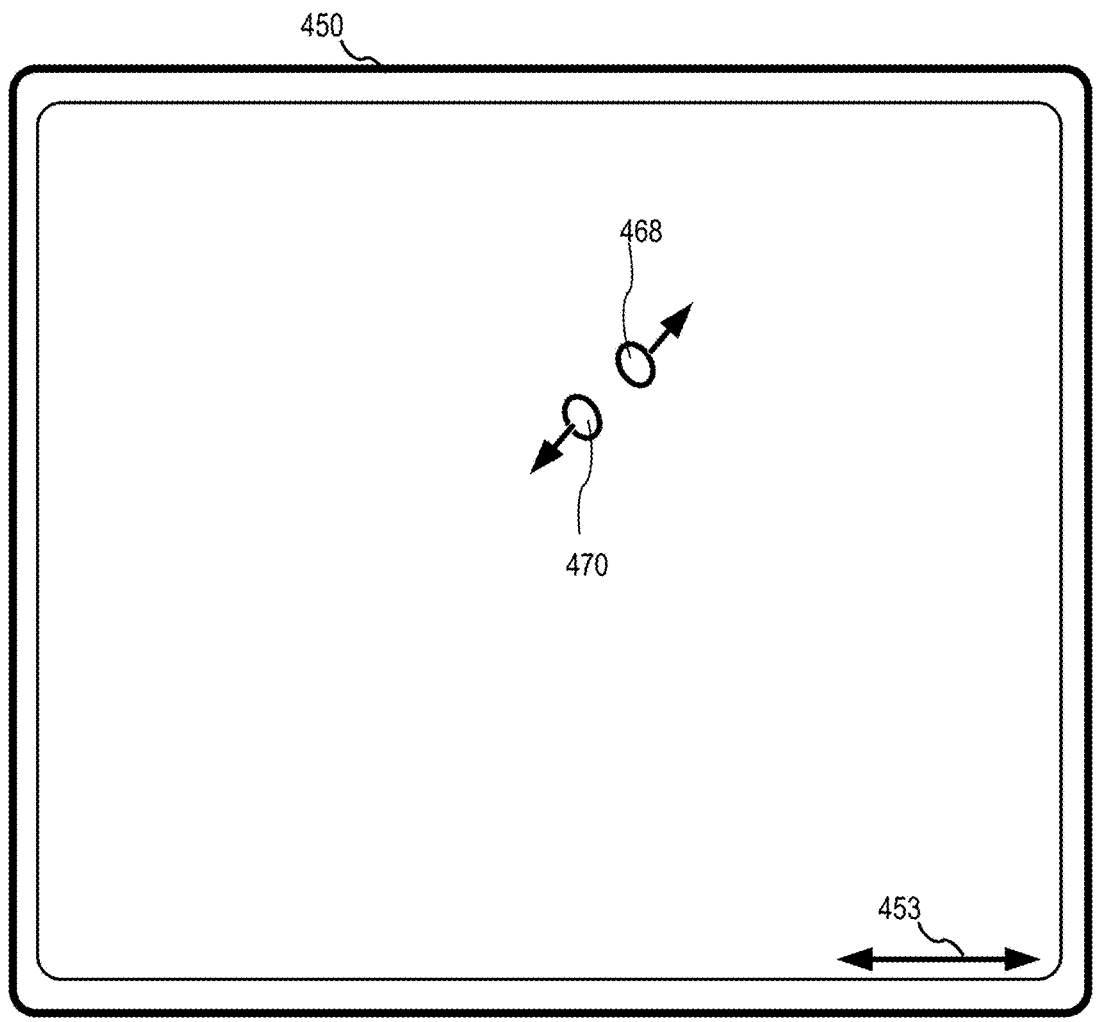
FIG. 4B illustrates an exemplary user interface for a multifunction device with a touch-sensitive surface that is separate from the display in accordance with some embodiments.
Figure 4B:
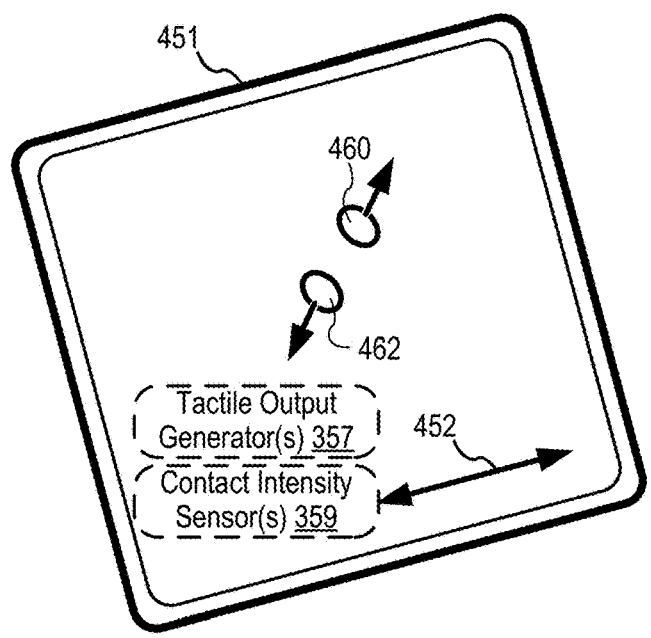

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
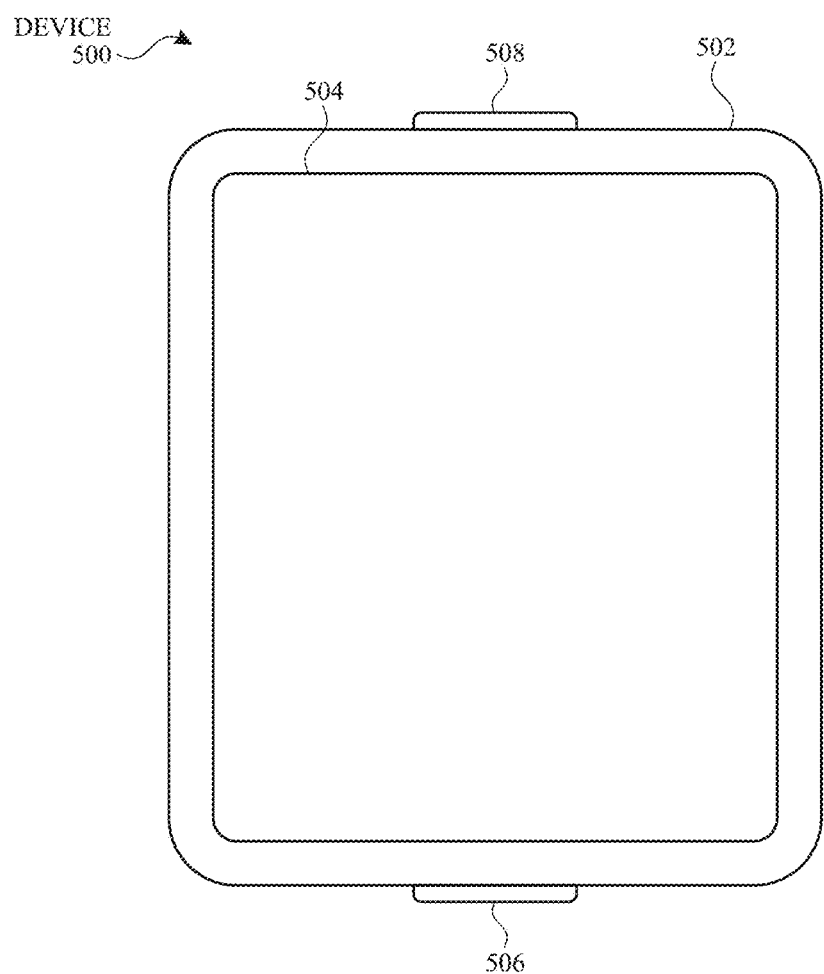
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
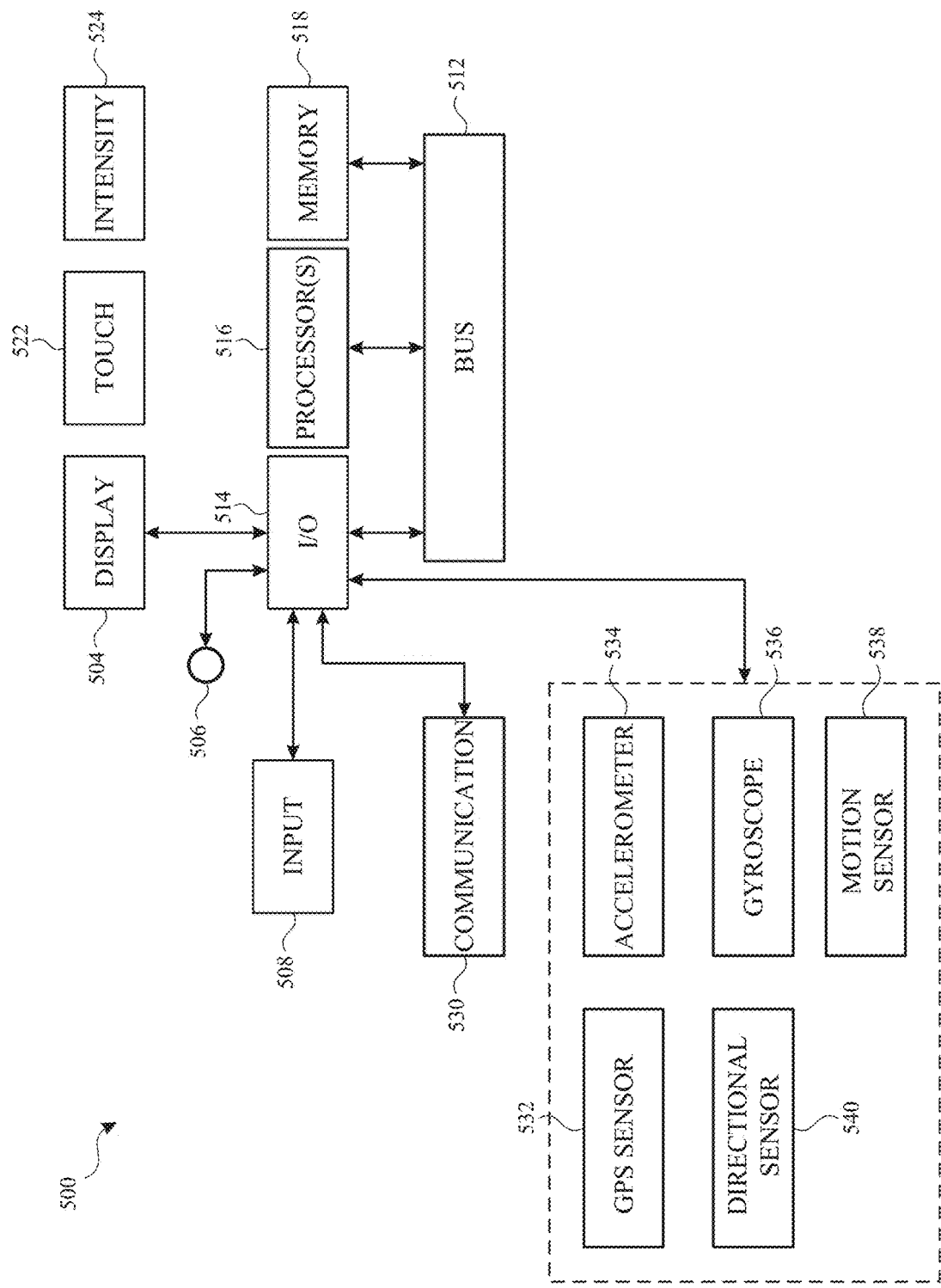
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700 and 1000 (FIGS. 7 and 10). Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1, 3, and 5). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

Figure 5C:
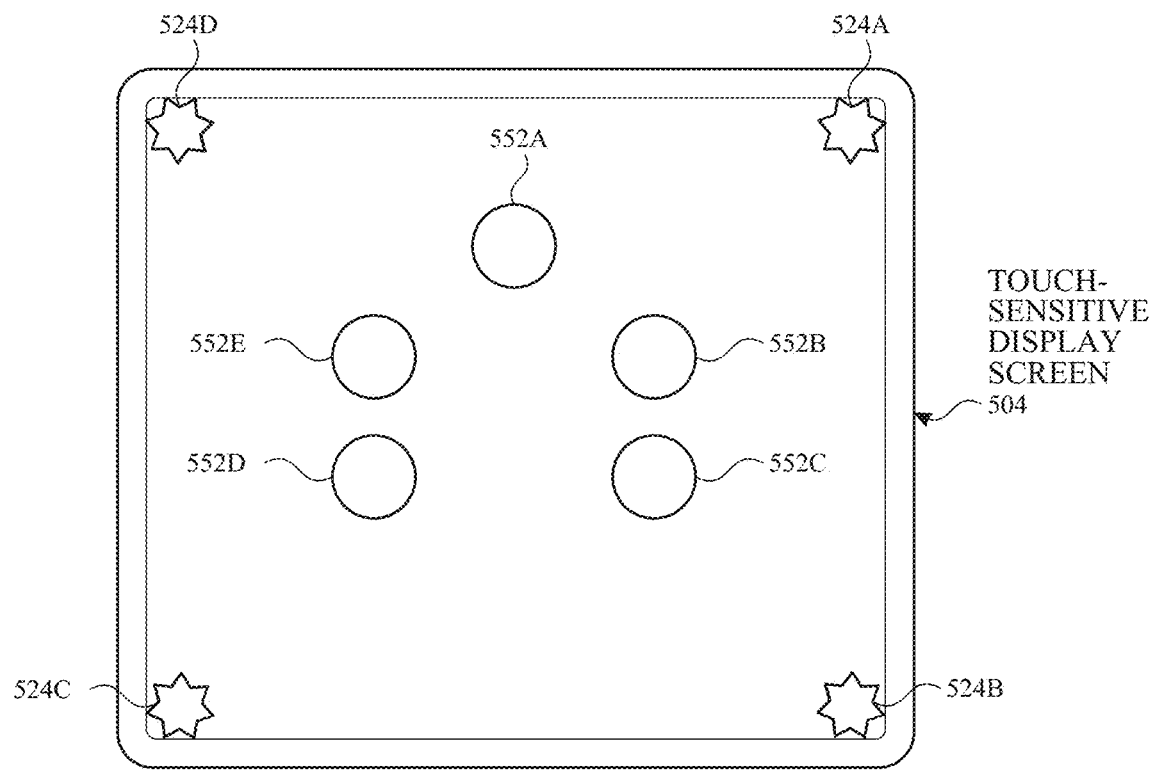
FIGS. 5C-5D illustrate exemplary components of a personal electronic device having a touch-sensitive display and intensity sensors in accordance with some embodiments.
Figure 5C:
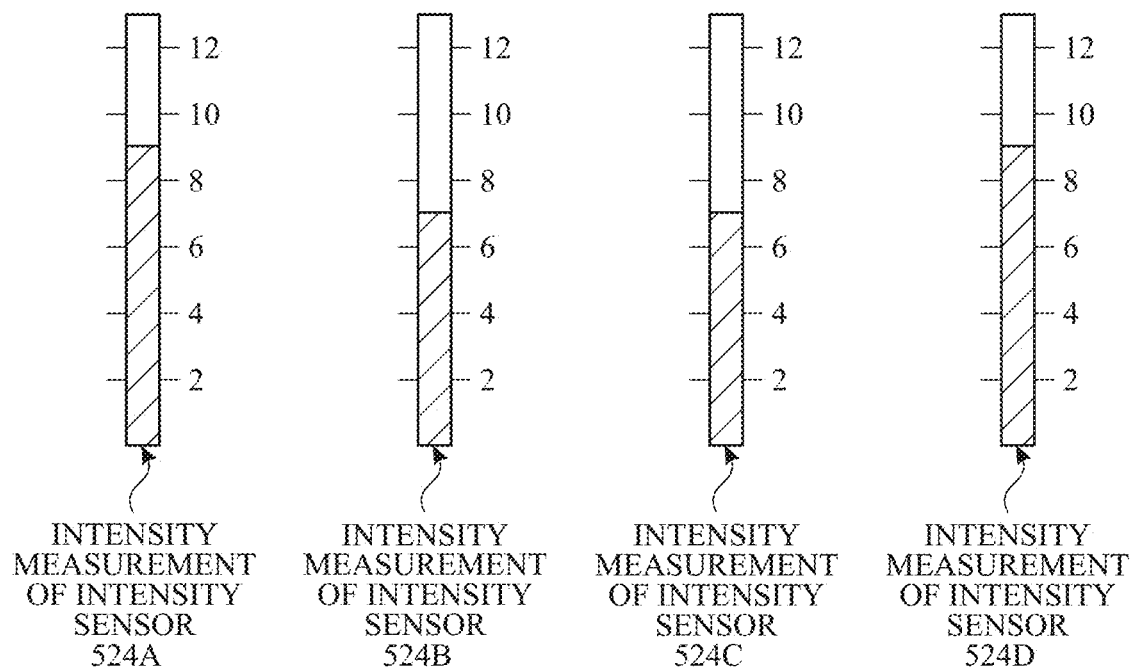
Figure 5D:
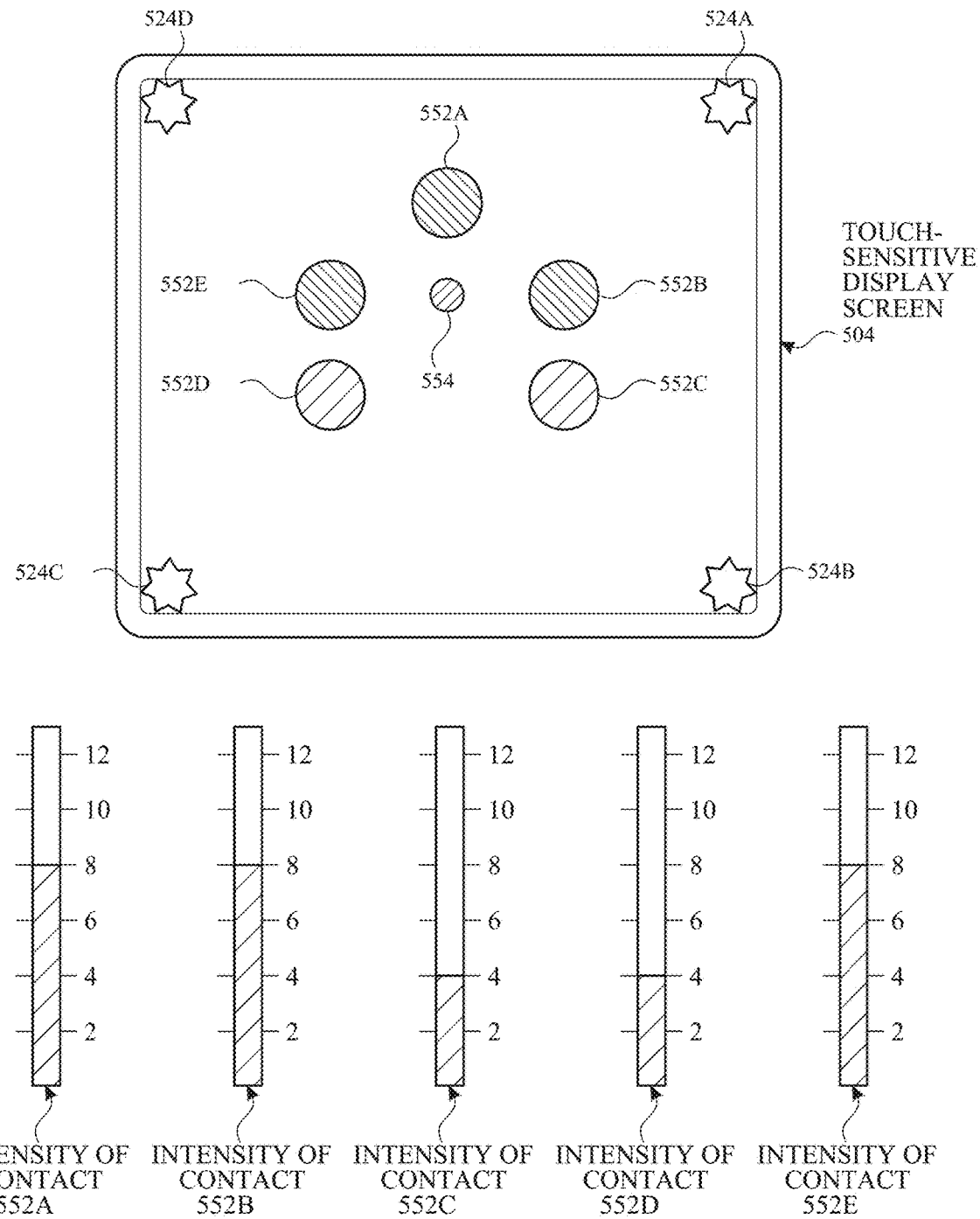

FIG. 5C illustrates detecting a plurality of contacts 552A-552E on touch-sensitive display screen 504 with a plurality of intensity sensors 524A-524D. FIG. 5C additionally includes intensity diagrams that show the current intensity measurements of the intensity sensors 524A-524D relative to units of intensity. In this example, the intensity measurements of intensity sensors 524A and 524D are each 9 units of intensity, and the intensity measurements of intensity sensors 524B and 524C are each 7 units of intensity. In some implementations, an aggregate intensity is the sum of the intensity measurements of the plurality of intensity sensors 524A-524D, which in this example is 32 intensity units. In some embodiments, each contact is assigned a respective intensity that is a portion of the aggregate intensity. FIG. 5D illustrates assigning the aggregate intensity to contacts 552A-552E based on their distance from the center of force 554. In this example, each of contacts 552A, 552B, and 552E are assigned an intensity of contact of 8 intensity units of the aggregate intensity, and each of contacts 552C and 552D are assigned an intensity of contact of 4 intensity units of the aggregate intensity. More generally, in some implementations, each contact j is assigned a respective intensity Ij that is a portion of the aggregate intensity, A, in accordance with a predefined mathematical function, Ij=A·(Dj/ΣDi), where Dj is the distance of the respective contact j to the center of force, and/Di is the sum of the distances of all the respective contacts (e.g., i=1 to last) to the center of force. The operations described with reference to FIGS. 5C-5D can be performed using an electronic device similar or identical to device 100, 300, or 500. In some embodiments, a characteristic intensity of a contact is based on one or more intensities of the contact. In some embodiments, the intensity sensors are used to determine a single characteristic intensity (e.g., a single characteristic intensity of a single contact). It should be noted that the intensity diagrams are not part of a displayed user interface, but are included in FIGS. 5C-5D to aid the reader.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

Figure 5E:
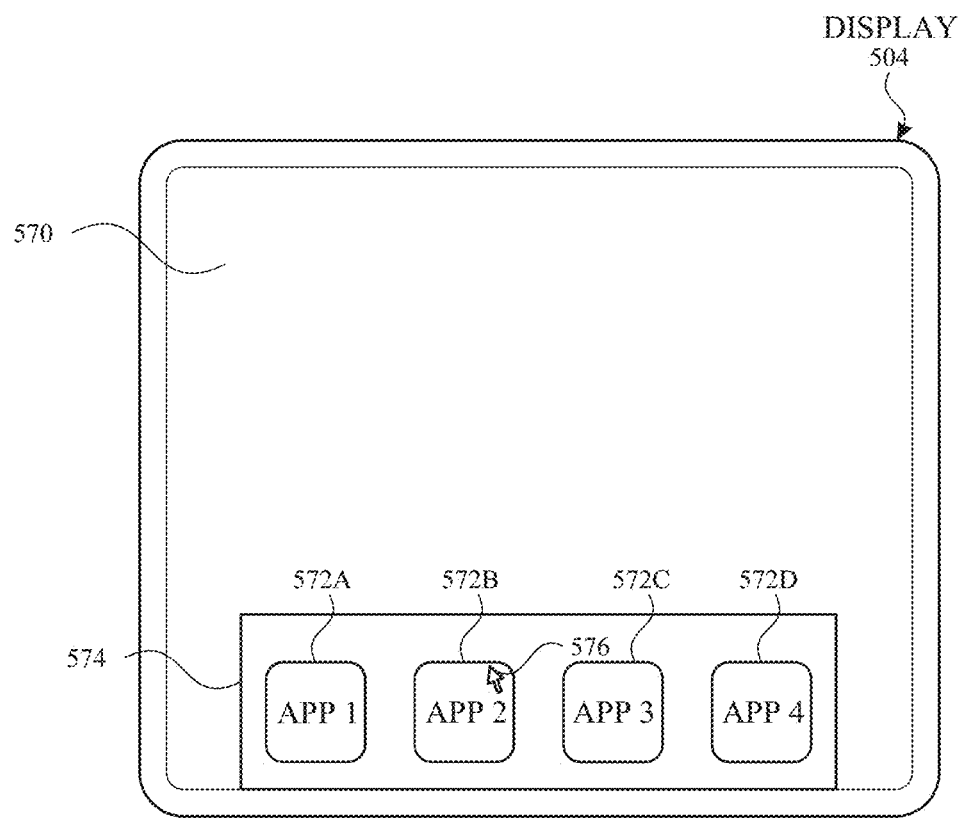
FIGS. 5E-5H illustrate exemplary components and user interfaces of a personal electronic device in accordance with some embodiments.
Figure 5E:
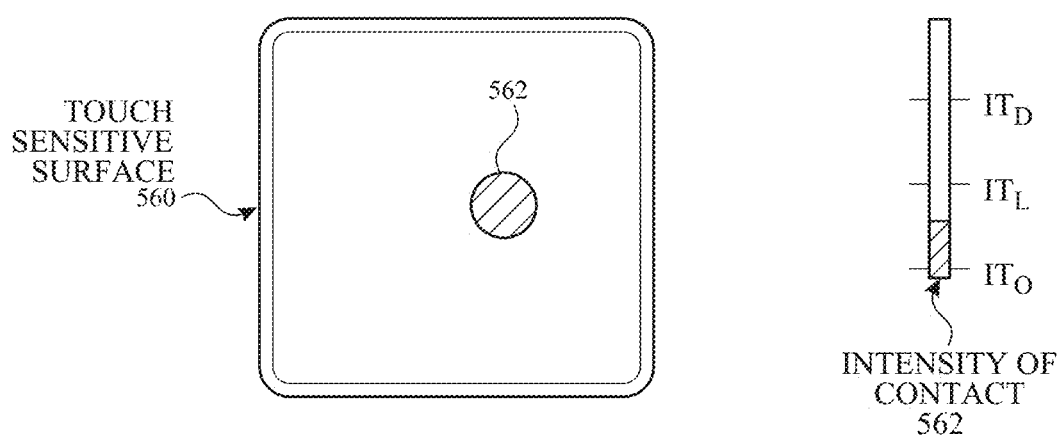
Figure 5F:
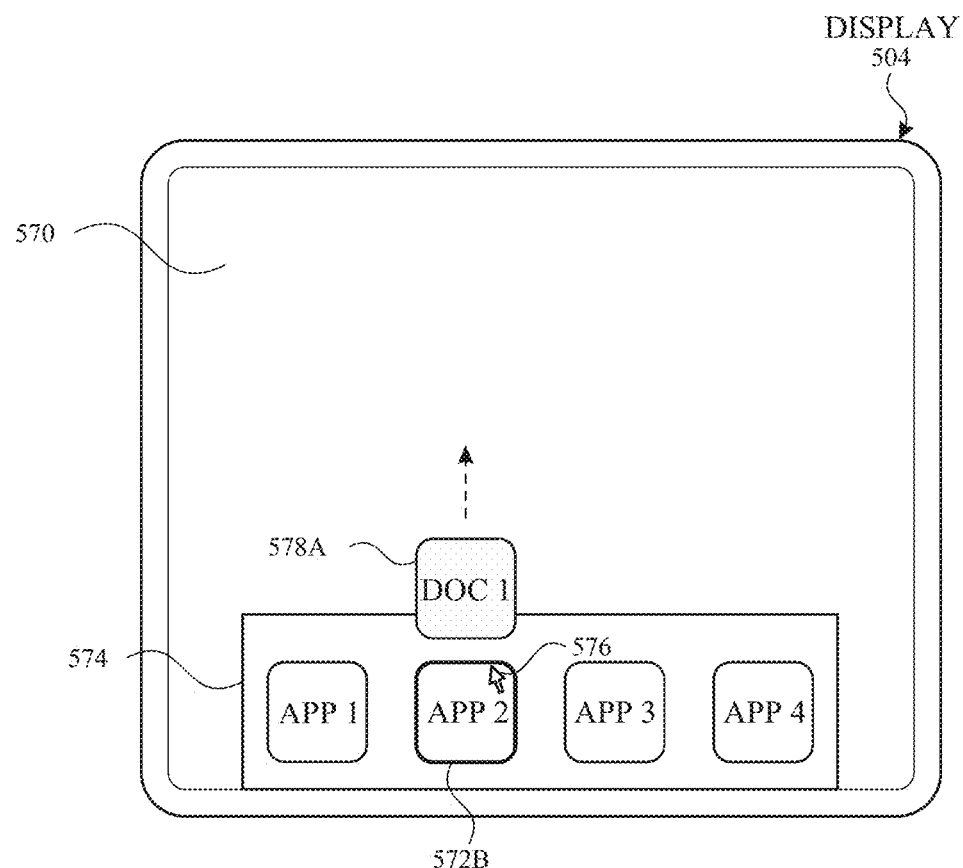
Figure 5F:
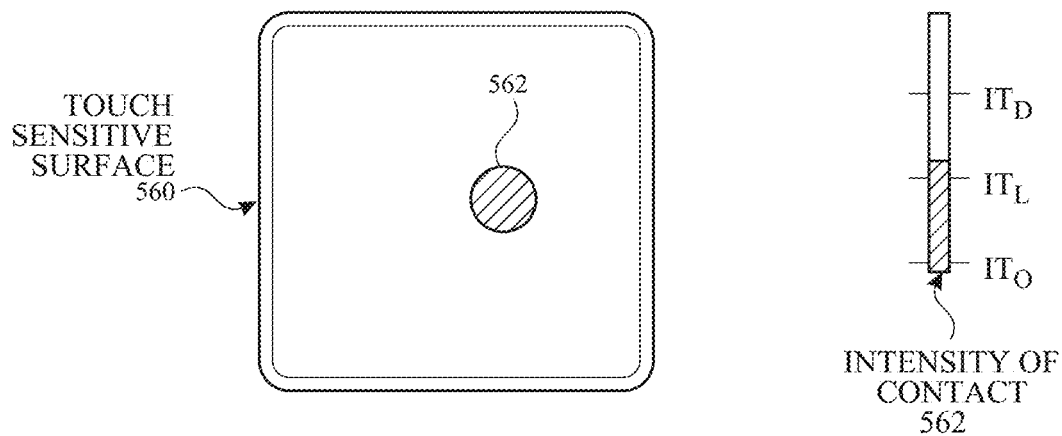
Figure 5G:
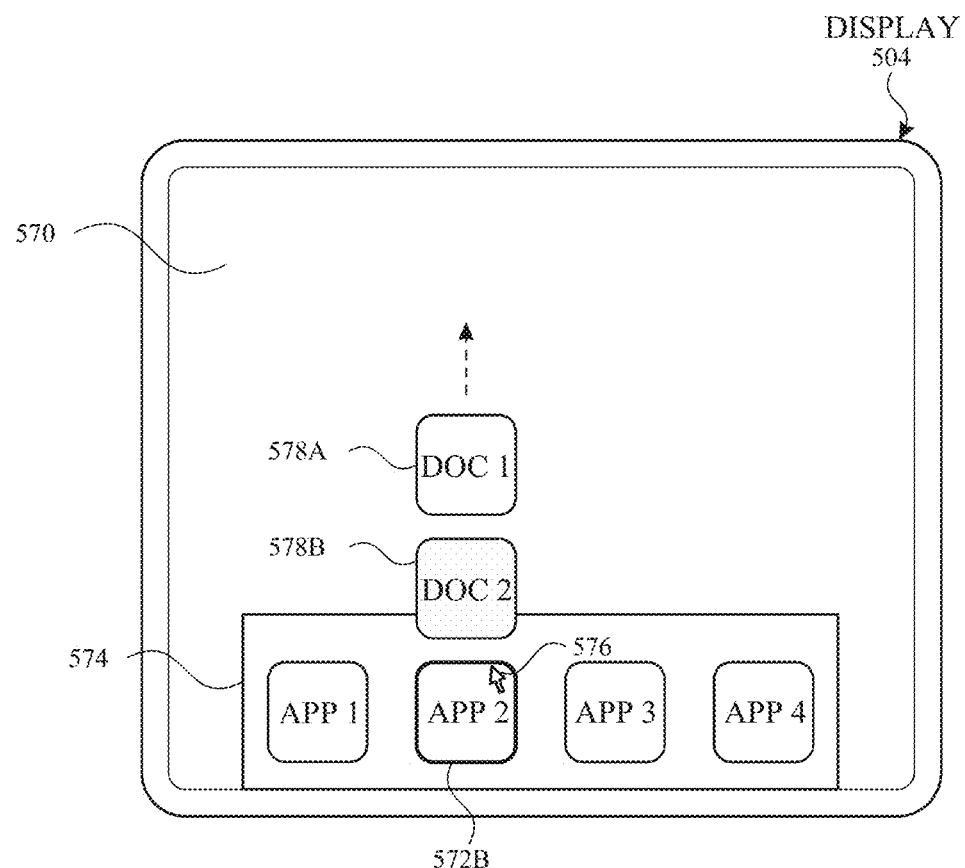
Figure 5G:
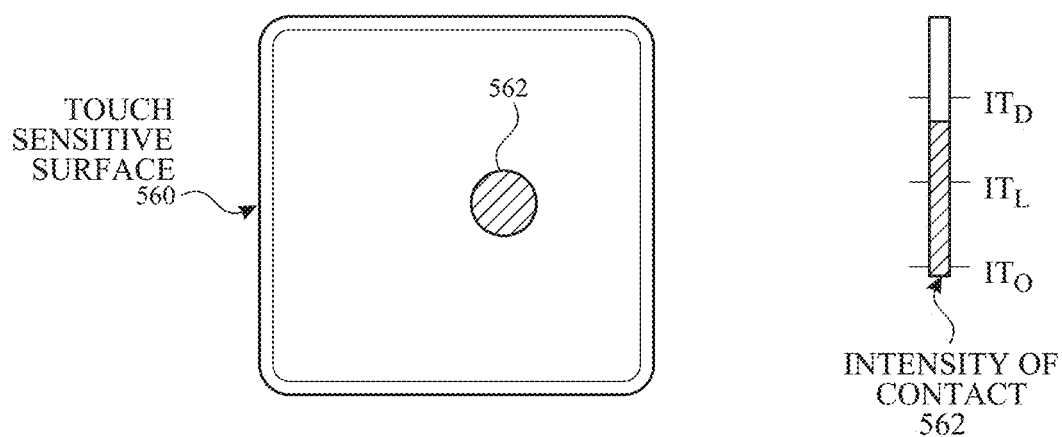
Figure 5H:
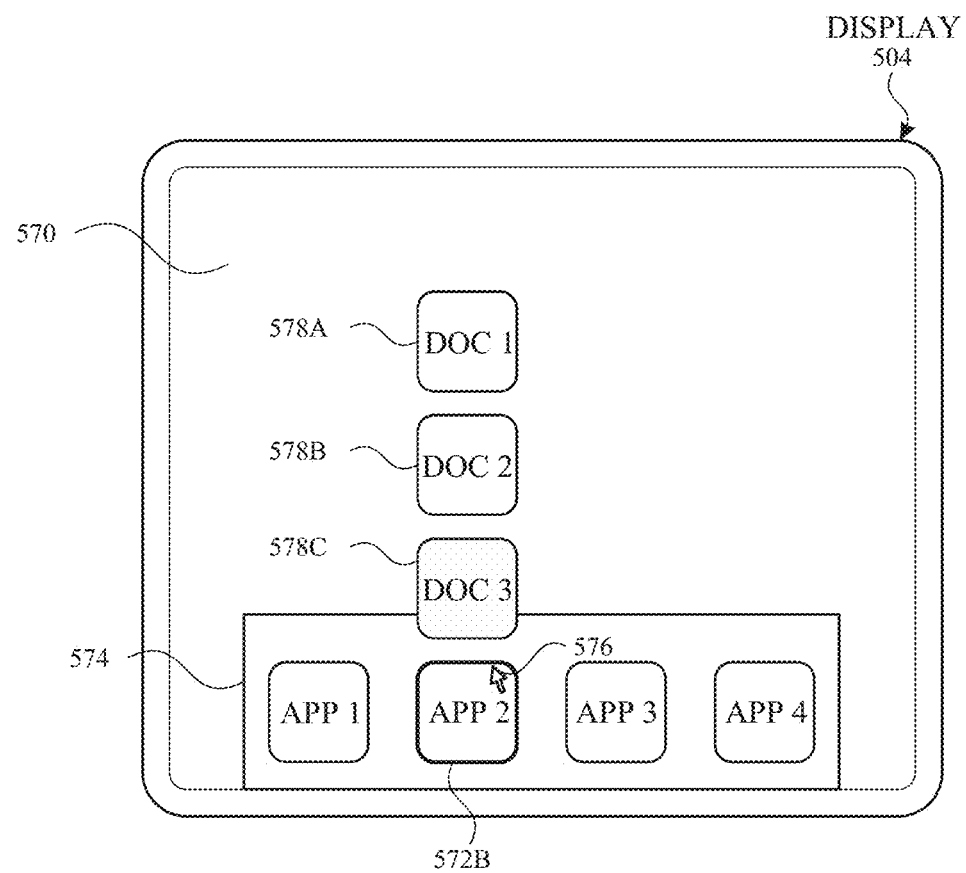
Figure 5H:
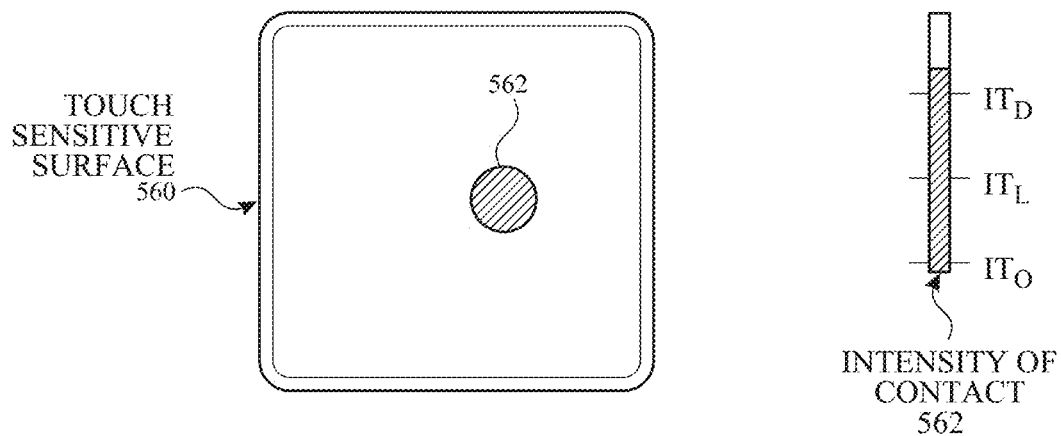

FIGS. 5E-5H illustrate detection of a gesture that includes a press input that corresponds to an increase in intensity of a contact 562 from an intensity below a light press intensity threshold (e.g., "$IT_L$") in FIG. 5E, to an intensity above a deep press intensity threshold (e.g., "$IT_D$") in FIG. 5H. The gesture performed with contact 562 is detected on touch-sensitive surface 560 while cursor 576 is displayed over application icon 572B corresponding to App 2, on a displayed user interface 570 that includes application icons 572A-572D displayed in predefined region 574. In some embodiments, the gesture is detected on touch-sensitive display 504. The intensity sensors detect the intensity of contacts on touch-sensitive surface 560. The device determines that the intensity of contact 562 peaked above the deep press intensity threshold (e.g., "$IT_D$"). Contact 562 is maintained on touch-sensitive surface 560. In response to the detection of the gesture, and in accordance with contact 562 having an intensity that goes above the deep press intensity threshold (e.g., "$IT_D$") during the gesture, reduced-scale representations 578A-578C (e.g., thumbnails) of recently opened documents for App 2 are displayed, as shown in FIGS. 5F-5H. In some embodiments, the intensity, which is compared to the one or more intensity thresholds, is the characteristic intensity of a contact. It should be noted that the intensity diagram for contact 562 is not part of a displayed user interface, but is included in FIGS. 5E-5H to aid the reader.

In some embodiments, the display of representations 578A-578C includes an animation. For example, representation 578A is initially displayed in proximity of application icon 572B, as shown in FIG. 5F. As the animation proceeds, representation 578A moves upward and representation 578B is displayed in proximity of application icon 572B, as shown in FIG. 5G. Then, representations 578A moves upward, 578B moves upward toward representation 578A, and representation 578C is displayed in proximity of application icon 572B, as shown in FIG. 5H. Representations 578A-578C form an array above icon 572B. In some embodiments, the animation progresses in accordance with an intensity of contact 562, as shown in FIGS. 5F-5G, where the representations 578A-578C appear and move upwards as the intensity of contact 562 increases toward the deep press intensity threshold (e.g., "$IT_D$"). In some embodiments, the intensity, on which the progress of the animation is based, is the characteristic intensity of the contact. The operations described with reference to FIGS. 5E-5H can be performed using an electronic device similar or identical to device 100, 300, or 500.

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

The device is optionally configured with one or more sensors for collecting health data of a user. The health data can include any suitable data relating to the health of the user. In some examples, the device may be configured to capture health data from the user. Such health data may indicate, for the user, a pulse rate, a heart rate, a heart rate variability measure, temperature data, a number of steps, an amount of time standing and sitting, a number of calories burned, a number of minutes exercised, and/or any other suitable data. The device may also be configured with one or more input devices by which the user can interact with the device. The device may also be configured with one or more output devices to output any suitable output information. For example, the device may be configured to output visual information, audio information, and/or haptic information. In some examples, the output information can be presented to the user in a manner that directs the user to perform one or more actions relating to breathing. For example, the output information can include a progress indicator that fluctuates (e.g., a type of the visual information). The progress indicator can be presented on a graphical user interface of the device and configured to lead the user through a series of breathing exercises included in a breathing sequence, as further described herein. The output information may be presented by an application running on the device.

The device may be associated with a second device (e.g., a paired or host device). In some examples, this may include the device being paired with the second device in any suitable manner. Pairing of the two devices optionally enables the second device to function as a proxy for the device. The device, the second device, or any suitable combination of the device and the second device may generate the output information based, at least in part, on the health data.

In accordance with some embodiments, the device used to perform the processes described herein (e.g., electronic device similar or identical to device 100, 300, or 500) includes multiple electrodes that are located on or near external surfaces of the device. In the present example, the device includes a first electrode and a second electrode that are located on or proximate to a rear-facing surface of the device body. In this example, the first electrode and the second electrode are configured to make electrical contact with the skin of the user wearing the device. In some cases, the first and second electrodes are used to take an electrical measurement or receive an electrical signal from the body of the user. The device optionally includes a third electrode and a fourth electrode that are located on or proximate to a perimeter of the device's body. In the present example, the third and fourth electrodes are configured to be contacted by one or more fingers of the user who is wearing or interacting with the device. In some cases, the third and fourth electrodes are also used to take an electrical measurement or receive an electrical signal from the body of the user. In some examples, the first, second, third, and fourth electrodes are all used to take a measurement or series of measurements that can be used to compute another health metric of the user's body. Health metrics that may be computed using the electrodes include, without limitation, heart functions (ECG, EKG), water content, body-fat ratios, galvanic skin resistance, and combinations thereof.

In some examples, the electronic device includes one or more apertures in the device's body. A light source may be disposed in each aperture. In one embodiment, each light source is implemented as a light-emitting diode (LED). In the present example, four apertures (e.g., the three light sources and a single detector) are used to form one or more sensors. Other embodiments can include any number of light sources. For example, two light sources can be used in some embodiments.

The light sources may operate at the same light wavelength range, or the light sources can operate at different light wavelength ranges. As one example, with two light sources one light source may transmit light in the visible wavelength range while the other light source can emit light in the infrared wavelength range. With four light sources, two light sources may transmit light in the visible wavelength range while the other two light sources can emit light in the infrared wavelength range. For example, in one embodiment, at least one light source can emit light in the wavelength range associated with the color green while another light source transmits light in the infrared wavelength range. When a physiological parameter of the user is to be determined, the light sources emit light toward the user's skin and the optical sensor senses an amount of reflected light. In some cases, a modulation pattern or sequence may be used to turn the light sources on and off and sample or sense the reflected light.

In some embodiments, the electrodes, light sources, and sensors discussed above are those shown in FIG. 14, and described in the accompanying text, of U.S. Provisional Application Ser. No. 62/348,804, entitled "Breathing Synchronization and Monitoring", filed on Jun. 10, 2016; and U.S. Provisional Application Ser. No. 62/348,808, entitled "Fluctuating Progress Indicator", filed on Jun. 10, 2016. The content of these applications is hereby incorporated by reference in their entirety for all purposes.

As used herein, an "installed application" refers to a software application that has been downloaded onto an electronic device (e.g., devices 100, 300, and/or 500) and is ready to be launched (e.g., become opened) on the device. In some embodiments, a downloaded application becomes an installed application by way of an installation program that extracts program portions from a downloaded package and integrates the extracted portions with the operating system of the computer system.

Examples of the present disclosure are directed to, among other things, methods, systems, and computer-readable media for conducting breathing sequences using one or more electronic devices. Initially, this optionally includes collecting user health data using one or more sensors of an electronic device, and analyzing the user health data to identify or estimate an estimated breathing pattern. The estimated breathing pattern is optionally synchronized with a breathing sequence. In some examples, the breathing sequence begins with an initial presentation of one or more breathing cues (e.g., a progress indicator). The breathing cues guide a user through the breathing sequence and can include visual cues, audible cues, and/or haptic cues. The synchronization of the estimated breathing pattern and the breathing sequence is optionally done in a way that helps the user smoothly transition her estimated breathing pattern into the breathing sequence. For example, the initial presentation of the breathing cue can be synchronized with a user breath event such as a user inhale cycle or a user exhale cycle.

In some examples, the breathing cue discussed above can be a visual breathing cue. Such visual breathing cues can be represented by a user interface element in the form of a progress indicator that is generated and presented to the user at the electronic device. The progress indicator can be defined as having one or more variable visual characteristics (e.g., complexity, alignment, visibility, etc.) that can optionally change over the course of the breathing sequence, or be selected based on configuration information. Changes in complexity of the fluctuating progress indicator can inform the user of their progress through the breathing sequence. For example, at the beginning of the breathing sequence, the progress indicator optionally includes a number of graphical elements (e.g., circular rings, ovular rings, squares, etc.) arranged in a pattern. As the user progresses through the breathing sequence, the number of user interface elements can be reduced. Thus, at completion of the breathing sequence, the progress indicator may have changed in complexity (e.g., fewer graphical elements and/or a less complex arrangement of the graphical elements). Changes in alignment and visibility of the progress indicator optionally also take place during the breathing sequence and can function as visual breathing cues for the user. For example, the progress indicator is optionally configured to fluctuate and rotate—grow while rotating clockwise to signal the user to inhale, to shrink while rotating counterclockwise to signal the user to exhale. At the conclusion of the breathing exercise, information (e.g., quantitative and/or qualitative) may be presented.

Attention is now directed towards embodiments of user interfaces ("UI") and associated processes that are implemented on an electronic device, such as portable multifunction device 100, device 300, or device 500. In some embodiments, the electronic device includes a display. In some embodiments, the display is a touch-sensitive display. In some embodiments, the electronic device includes a touch-sensitive surface. In some embodiments, the electronic device includes a rotatable input mechanism.

FIGS. 6A-6F illustrate exemplary user interfaces for conducting breathing sequences, in accordance with some embodiments. The user interfaces in these figures are used to illustrate the processes described below, including the processes in FIG. 7.

Figure 6A:
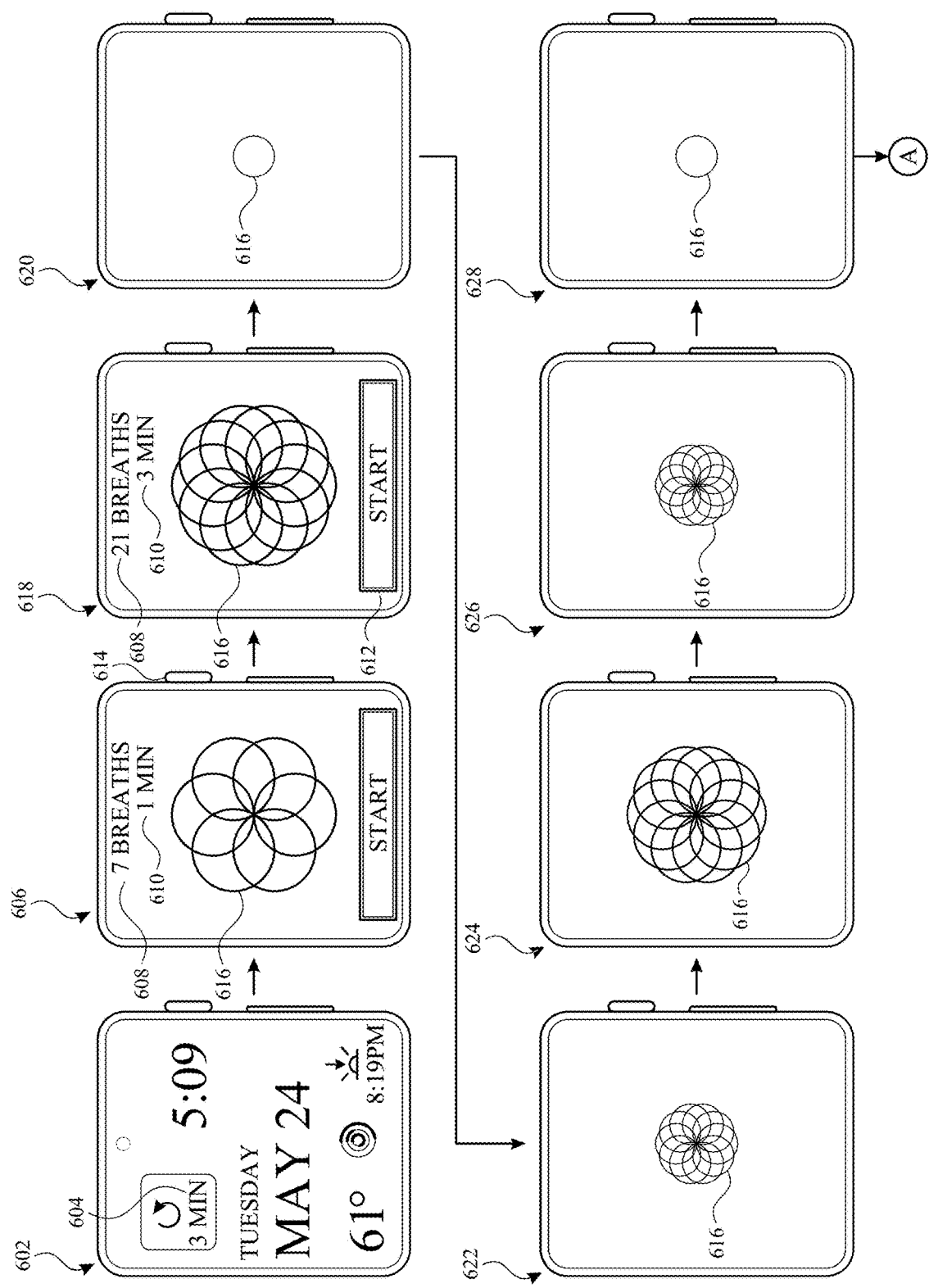
FIGS. 6A-6F illustrate exemplary user interfaces for conducting breathing sequences in accordance with some embodiments.

FIG. 6A illustrates exemplary user interfaces for initiating and conducting a breathing sequence, in accordance with some embodiments. User interface screen 602 depicts a home screen of the electronic device (hereinafter referred to as "device"). General information such as the date, time of day, temperature, and the like, are optionally presented on user interface screen 602. In some examples, user interface screen 602 is optionally displayed following device startup, and optionally in response to a user exiting an application running on the device. User interface screen 602 includes selectable affordance 604 which, when selected, optionally causes the device to launch an application used to conduct a breathing sequence. In some examples, the device is a wearable electronic watch, and affordance 604 is presented as a watch face complication on the watch display. Affordance 604 is optionally depicted as a miniaturized version of a progress indicator (as described below, for example, with respect to user interface screens 606-628). In this example, affordance 604 is depicted to include an image of a stylized arrow, which is a symbol associated with an application used to conduct breathing sequences on the device. Thus, the affordance 604 conveys that it is associated with accessing breathing sequences. In other examples, an image included with affordance 604 is any suitable image.

In accordance with some embodiments, affordance 604 is associated with textual information. In some examples, the device determines an aggregate amount of time and displays it as the textual information. In the example depicted, affordance 604 includes the text "3 MIN", representing that a user has conducted 3 minutes of breathing in one or more breathing sequences over a current period (e.g., today).

At user interface screen 602, the device receives user input corresponding to selection of affordance 604 and, in response, displays an exemplary configuration user interface as depicted in user interface screen 606.

User interface screen 606 illustrates an exemplary configuration user interface of a breathing sequence. In some embodiments, the configuration user interface is displayed during a configuration phase of the breathing sequence. In some examples, the configuration user interface is displayed after an application for conducting breathing sequences is started. The configuration user interface includes a prompt to select a number of cycles of the breathing sequence. For example, user interface screen 606 includes indicator 608, which represents a number of cycles of the breathing sequence that can be selected by the user. In this example, the number of cycles represents a number of breaths (e.g., comprised of an inhale period and an exhale period). In some examples, the breathing sequence will provide breathing cues to train the user during a user's breathing exercise, the exercise lasting for a number of breaths equal to the number of cycles. The number of breaths is important because it is an indication of the length of a breathing exercise to be performed by the user. By allowing the user to adjust the number of cycles (e.g., breaths), the user is given flexibility to customize their breathing exercises, increasing the likelihood that a user will perform breathing exercises, and thereby achieve the health benefits of conscious breathing. For example, if a user has a small amount of available time, they can opt to perform a short breathing exercise of only 7 breaths—that way, they can still achieve the health benefits while maintaining a busy schedule. The configuration user interface optionally includes an indication of a length of time of the breathing sequence (e.g., indicator 610) that is displayed in addition to, or in place of, the number of cycles of the breathing sequence (e.g., indicator 608). The configuration user interface optionally includes a progress indicator. For example, user interface screen 606 includes progress indicator 616, depicted as a plurality of graphical elements (e.g., overlapping circles). The progress indicator, discussed in more detail below, is a visual element that is optional and that provides visual cues to the user to guide their breathing throughout the breathing sequence.

In accordance with some embodiments, the device receives a first user input. For example, the first user input is received at the configuration user interface depicted in screen 606 and corresponds to a selection of the number of cycles of the breathing sequence.

User interface screen 618 illustrates an exemplary configuration user interface of a breathing sequence after the device has received user input corresponding to selection of the number of cycles. In the example depicted, the device receives user input at user interface screen 606 representing selection of the number of cycles of the breathing sequence. In response to the user input, the device adjusts the number of cycles. For example, at user interface screen 618, indicator 608 now reads "21 breaths", indicating that the number of cycles (e.g., breaths) has been increased to 21 from the previous number of 7 (e.g., indicator 608 reads "7 breaths" at screen 606). In some embodiments, the device receives the user input on a touch-sensitive surface or a touch-sensitive display. In some embodiments, the device includes a rotatable input mechanism and the user input is a rotation of the rotatable input mechanism. In the example depicted, the device received a rotation of rotatable input mechanism 614, which caused the device to adjust the number of cycles from 7 to 21. In some examples, because the number of cycles has been adjusted (e.g., increased by a factor of 3), the length of time of the breathing sequence is also adjusted (e.g., increased by a factor of 3). For example, indicator 610 at user interface screen 618 now reads "3 min" (e.g., indicating a length of three minutes). As will be appreciated by one of skill in the art, in the example depicted, the logical relationship between the number of cycles and the length of time of the breathing sequence is 7 cycles per minute. This logical relationship is also referred to hereinafter as a "cyclic rate". In some examples, the cyclic rate is a value other than 7 cycles per minute (e.g., 5 cycles per minute).

The number of cycles (e.g., breaths) may be determined based at least in part on the time (e.g., duration of the breathing phase) and a breath ratio (e.g., a ratio of the time it takes to inhale compared to the time it takes to exhale) applicable to the breathing sequence. For example, for a duration of 1 minute (60 seconds) and for a breath ratio of 1:1.5 (e.g., ratio of inhale to exhale), each full breath (e.g., an inhale and an exhale) will take 8.5 seconds, with 3.4 seconds for each inhale (e.g., based on the "1" of the 1:1.5 breath ratio) and 5.1 second for each exhale (e.g., based on the "1.5" of the 1:1.5 breath ratio). In some embodiments, the duration of a full cycle (e.g., breath) includes an added duration of time that is optionally added between inhale and exhale periods, in order to account for the slight delay that it takes for a person to transition from an inhale to an exhale (and vice versa). For example, the time between points 656 and 658 on cycle 650 of FIG. 6C illustrates such a duration of time. In this example, the exhale and inhale periods would thus be slightly shorter than 5.1 and 3.4 seconds, respectively, in order to maintain a breath ratio of 1:1.5 if the added duration is included in the duration of a full breath. The added duration is, for example, 0.5 seconds. In some examples, an added duration inserted at a transition from an inhale to an exhale period is a different length of time than the added duration inserted at a transition from an exhale to an inhale period. In some embodiments, an added duration is not included in a cycle. In some embodiments, only one transition between the periods (during a cycle) has an added duration. In some embodiments, both transitions between the periods (during a cycle) have an added duration.

In some embodiments, adjusting the number of cycles causes the appearance of a displayed indicator to change. For example, as shown in screen 606 of FIG. 6A, indicator 616 is created from 6 graphical elements (e.g., overlapping circles) when the number of cycles is set to 7 breaths, but is created from 10 graphical elements (e.g., overlapping circles) when the number of cycles is set to 21 breaths, as shown in screen 618. Accordingly, the appearance of indicator 616 can be varied in accordance with the selected number of cycles to provide visual indication to the user of the selected number of cycles, thus creating a more intuitive human-machine interface for configuring a breathing sequence.

In accordance with some embodiments, at user interface screen 618, the device receives user input representing a request to initiate a breathing phase of the breathing sequence. For example, the user input can be user selection of start affordance 612 at user interface screen 618.

In accordance with some embodiments, in response to receiving the user input representing a request to progress to (e.g., initiate) the breathing phase of the breathing sequence, the device progresses to (e.g., initiates) the breathing phase of the breathing sequence. In accordance with some embodiments, during the breathing phase of the breathing sequence, the device displays a first version of a progress indicator. In the example depicted, the first version of the progress indicator is a version that is created from 10 overlapping circles (e.g., indicator 616 shown in user interface screen 618). In accordance with some embodiments, the device fluctuates the first version of the progress indicator in accordance with the selected number of cycles during the breathing phase of the breathing sequence.

In accordance with some embodiments, prior to initiating the breathing phase of the breathing sequence, the device receives a second user input and, in response to receiving the second user input, progresses to the breathing phase of the breathing sequence. In the example depicted, the received second user input is selection of start affordance 612 of user interface screen 618 and, in response, the device progresses to (e.g., initiates) the breathing phase and displays and fluctuates a progress indicator (e.g., as shown in screens 620-628).

In some embodiments, progressing to the breathing phase of the breathing sequence includes initiating the breathing phase of the breathing sequence in response to the second user input. In some embodiments, progressing to the breathing phase of the breathing sequence includes initiating a preliminary phase (described below with respect to screens 668A-668E of FIG. 6D) of the breathing sequence in response to the second user input, and initiating the breathing phase after completion of the preliminary phase of the breathing sequence.

In some embodiments, the first and second user inputs are distinct user inputs. For example, the first user input can be a rotation of a rotatable input mechanism 614 to select a number of cycles, and the second user input can be a touch input on start affordance 612. In some embodiments, the first user input and the second user input are the same. For example, the user may accept a default number of cycles that is presented on the display at user interface screen 606 by providing touch input on start affordance 612. In response, the device sets the selected number of cycles to the default number of cycles that are displayed (e.g., 7 cycles). Thus, the first and second user inputs would both be the same input on the start affordance 612 in this instance.

In accordance with some embodiments, during the breathing phase of the breathing sequence, a progress indicator fluctuates in accordance with a selected number of cycles. User interface screens 620-628 depict an exemplary fluctuation of a progress indicator 616 in accordance with one cycle. In this example, the cycle (of a breathing sequence) represents one complete inhale period and one complete exhale period, wherein the beginning of the inhale period coincides with the beginning of the cycle, and wherein the end of the cycle coincides with the end of the exhale period.

User interface screen 620 depicts progress indicator 616 at the beginning of the cycle. In this example, as shown in user interface 620, progress indicator 616 is displayed at its smallest size, relative to any other time during the cycle, at the beginning of the cycle. The progress indicator 616 being displayed at its smallest form signals the beginning of the inhale period to the user, and thus that the user should begin inhaling. In some examples, the progress indicator is a simple circle at its smallest size, as shown in screen 620. Thus, the user is provided a visual cue during the breathing phase that displays the appropriate breathing action that the user should be performing during the breathing sequence.

User interface screen 622 depicts progress indicator 616 halfway through the inhale period of the cycle. In some embodiments, the progress indicator changes in size during the inhale period of the cycle. For example, as shown in user interface screen 622, progress indicator 616 has grown in size during an inhale period, and will continue to do so throughout the inhale period. In some examples, the change is size is the result of the movement of graphical elements (e.g., circles), which began collapsed into one small circle (e.g., all circles perfectly overlapping each other), and expanded outward to form a partially-overlapping collection of graphical elements (e.g., circles), as seen in screen 622. The changing size of the progress indicator during an inhale period (e.g., by growing) provides an intuitive visual cue to the user that they should be inhaling (e.g., increasing the size of their lungs by drawing in air). Accordingly, the cognitive burden on the user when following breathing cues is reduced.

User interface screen 624 depicts progress indicator 616 at the transition between the inhale period and the exhale period. In the example depicted, progress indicator 616 is at its largest size, relative to any other time during the cycle, at the transition between the inhale and exhale periods of the cycle, as shown in user interface 624. The progress indicator 616 being at its largest signals the end of the inhale period and the beginning of the exhale period to the user, and thus that the user should begin exhaling.

In some examples, in order to complete fluctuation of the progress indicator in accordance with a cycle, the progress indicator returns to its original size. User interface screens 626 and 628 depict the progress indicator during an exemplary exhale period that follows the inhale period of the cycle. At user interface screen 626, progress indicator 616 is depicted halfway through the exhale period of the cycle, and it has shrunk in size (since the display at screen 624). At user interface 628, progress indicator 616 has returned to its smallest size at the end of the exhale period, which also corresponds to the end of the cycle and the beginning of an inhale period for the next cycle. As can be seen, the progress indicator in user interface screen 628 (end of cycle) is the same size as the progress indicator in user interface screen 620 (beginning of cycle). In some examples, the size of the progress indicator returns to the same size, signaling to the user that the cycle is over and that a new cycle may begin (e.g., and repeat fluctuating the progress indicator as shown in user interface screens 620-628).

The change from the progress indicator in screen 620 to the progress indicator in screen 624 may correspond to a first breath event (e.g., an inhale period), and the length of time it takes to change can correspond to a length time of the first breath event (e.g., 3.4 seconds for a 1:1.5 breath ratio at 7 breaths/minute). The change from the progress indicator of screen 624 to the progress indicator of screen 628 may correspond to a second breath event (e.g., an exhale period), and the length of time it takes to change can correspond to a length of time of the second breath event (e.g., 5.1 seconds for a 1:1.5 breath ratio at 7 breaths/minute). It is understood that the transition (e.g., fluctuation) of the progress indicator between screens 620-628 optionally includes many more displays (not depicted here) of the progress indicators in order to produce a smooth transition.

As mentioned above, fluctuating the progress indicator (e.g., as illustrated in screens 620-628) provides the user with intuitive visual cues to follow during a breathing phase. The user can utilize these visual cues to train their breathing during a breathing exercise when conducting a breathing sequence on the device. Fluctuating an indicator as described herein is an intuitive signal to the user, as it resembles the rhythmic nature of an individual's natural breathing pattern. Thus, these visual cues reduce the cognitive burden on the user when conducting breathing sequences, increase the effectiveness of the training provided by the breathing sequences, and reinforce healthy conscious breathing patterns for breathing exercises performed by the user.

In some examples, different versions of the progress indicator can each fluctuate in a distinct manner. For example, a first version of a progress indicator can fluctuate between a first size and a second size (e.g., between 50% and 100%), and second version can fluctuate between the second size and a third size (e.g., between 25% and 50%).

In some embodiments, a progress indicator is displayed, and if selected, causes the device to progress to a breathing phase, launch an application for conducting breathing sequences, or cause the device to display a configuration user interface. In some examples, the progress indicator 616 is displayed (as depicted in 606, however without other displayed elements such as indicator 608, start affordance 612) on the screen, in response to a user of the device performing certain actions with respect to the device (e.g., lifting the device, viewing the device, and the like), randomly, or according to some interval. In some examples, presentation of the progress indicator on the display functions as a reminder to the user to participate in a breathing exercise (e.g., to conduct a breathing sequence).

Figure 6B:
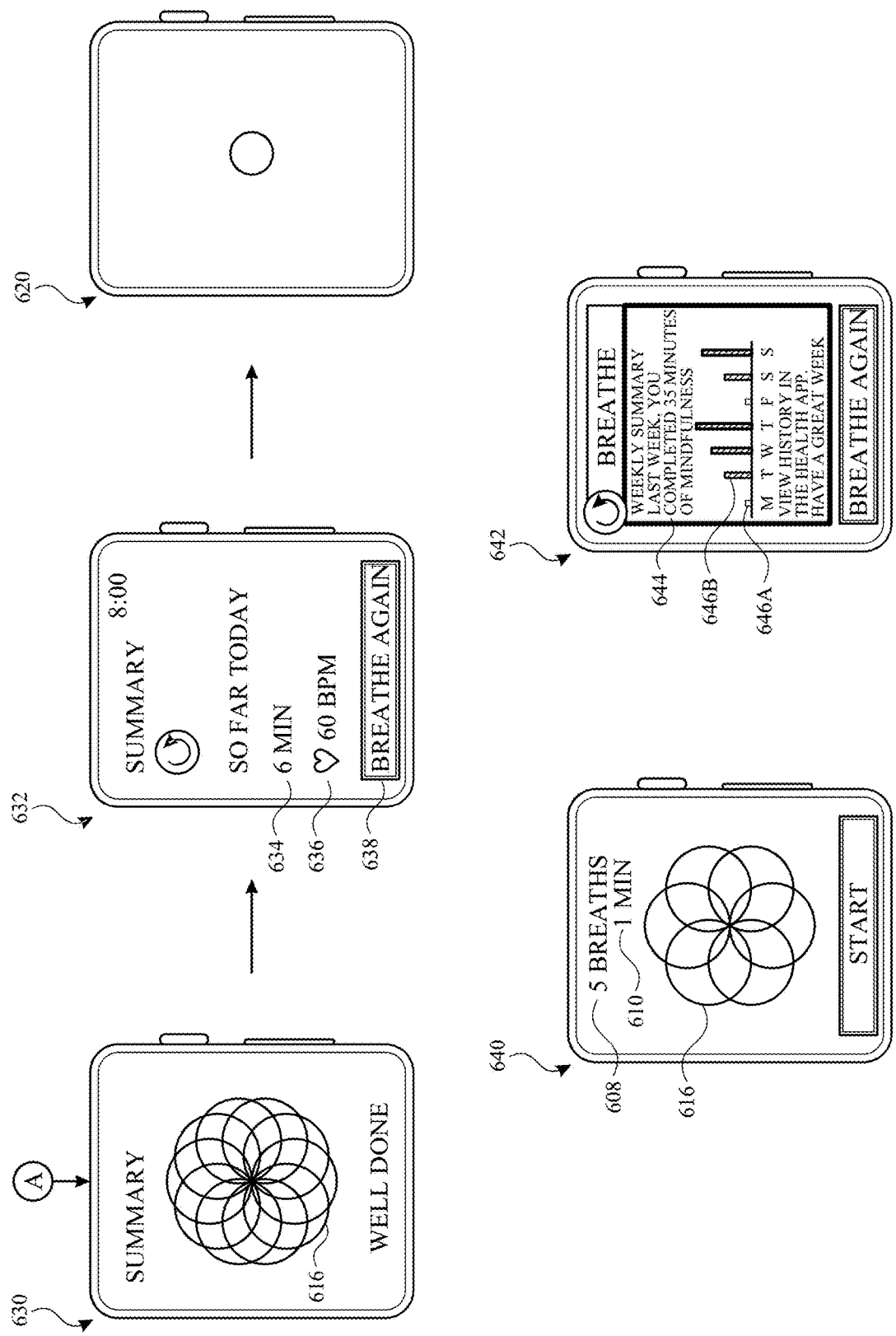
Figure 6C:
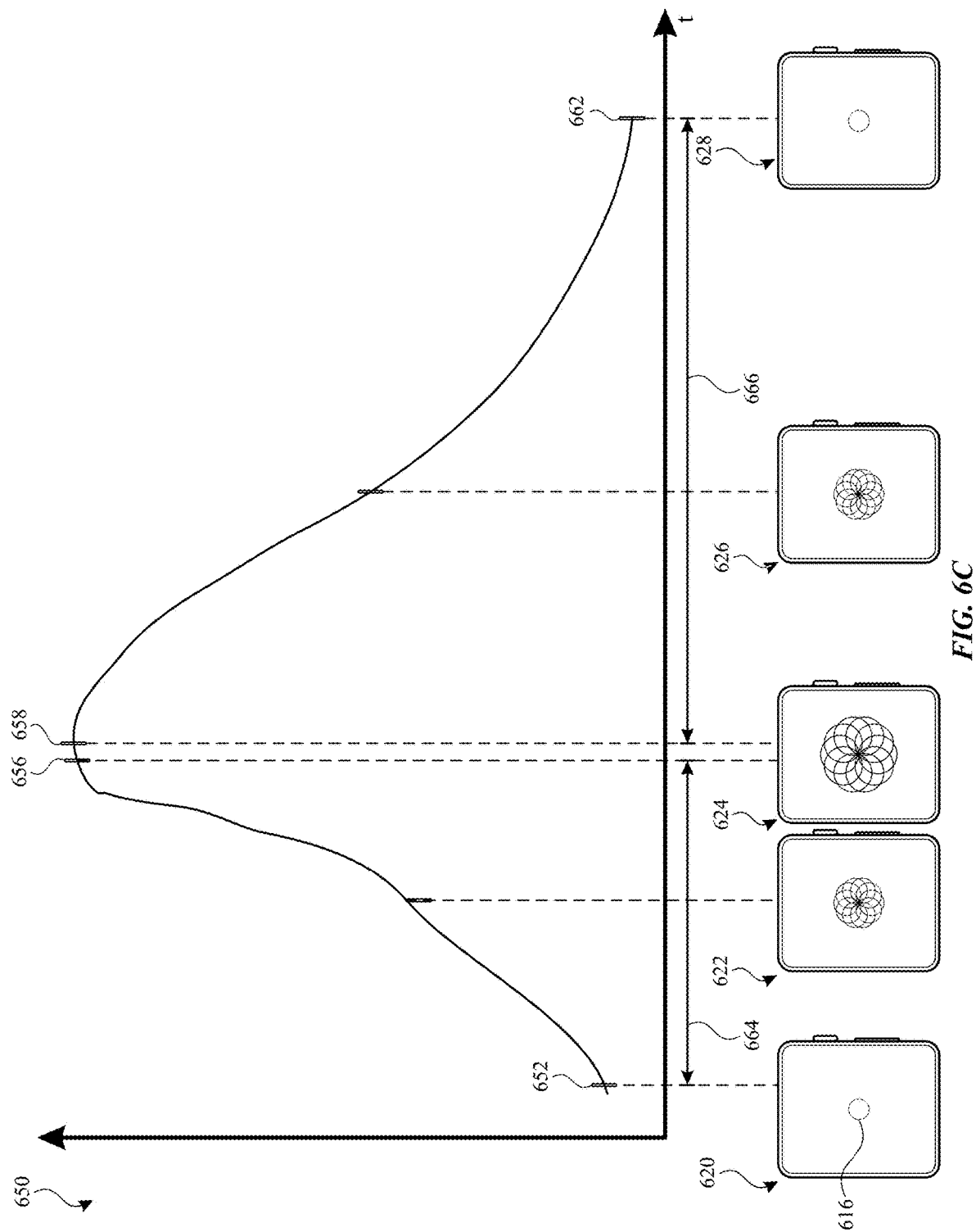

At the conclusion of the breathing phase of the breathing sequence, the display may present the user interface screen 630, shown in FIG. 6B. User interface screen 630 depicts an exemplary completion interface that includes an enlarged progress indicator 616 (e.g., larger than at any point during the breathing phase). After completion of the breathing phase, the progress indicator can also change colors, pulsate, rotate, animate, or the like, in order to signal to the user that the breathing phase is complete. In some examples, the visual behavior of a displayed progress indicator differs from the first or second version of the progress indicator displayed during a breathing or preliminary phase—that way, the progress indicator 616 can provide an extra visual cue to the user, specifically, that the breathing phase is complete. At user interface screen 630, the device may automatically progress to display another completion interface (e.g., user interface screen 632), or may do in response to user input. For example, the user input may be selection of the progress indicator 616, or any other user input. In some embodiments, the user interfaces screens 630 and 632 are displayed during a concluding phase of the breathing sequence.

User interface screen 632 depicts an exemplary completion interface, which is displayed after the completion of the breathing phase. The completion interface optionally includes information about the breathing sequence. In some examples, a completion interface indicates that the user completed the breathing sequence (e.g., user interface screen 630 includes the textual information "Well Done"). In some examples, a completion interface indicates a quantitative performance metric ("You hit 90% of your breaths") and/or indicates a suggestion ("Try taking deeper breaths next time"), and/or any other suitable information. The information included in a completion interface may provide reinforcement of the benefits of taking time to breathe each day, thereby encouraging the user to continue and progress with conducting breathing sequences to guide their breathing. Similarly, the information included in a completion interface may encourage the user to work to improve her health metrics (e.g., heart rate).

In some examples, sensor data collected during the preliminary phase is compared to sensor data collected during the concluding phase to determine whether participating in the breathing sequence effected a change in any health metric. For example, heart rates of the user can be compared, heart rate variability measures can be compared, pulse rates of the user can be compared, any other metric that can be indicative of stress, anxiety, and the like. Providing these comparisons, or similar ones, to the user can serve to reinforce the benefits of conducting breathing sequences by providing the user feedback that allows the user to track long-term progress (e.g., reduce physiological indicators of chronic stress) and short-term progress (e.g., relax by lowering a heart rate).

In some examples, a completion interface is not displayed after completion of the breathing phase. For example, in response completion of the breathing phase of the breathing sequence, the display can display a configuration user interface, or may display a home screen of the device.

In accordance with some embodiments, the device determines an aggregate amount of time representing a completed number of cycles of the breathing sequence over a goal period. In accordance with some embodiments, the goal period is the current day. For example, the time representing a completed number of cycles represents a total breathing time completed today. In response to detecting completion of the breathing phase of the breathing sequence, the device displays, on the display, a completion interface comprising: an indication of the aggregate amount of time, and a third affordance. For example, user interface screen 632 depicts an exemplary completion interface, and includes indicator 634, which depicts an exemplary indication of the aggregate amount of time (e.g., 6 minutes). User interface screen 632 also depicts an exemplary third affordance, breathe again affordance 638.

The user may wish to conduct another breathing sequence after completion a first breathing sequence. For example, the user may wish to repeat the completed breathing sequence. In accordance with some embodiments, the device receives user input selection of the third affordance and, in response, progresses to the breathing phase of the breathing sequence. For example, as shown in FIG. 6B, the device progresses to display user interface 620 (reproduced from FIG. 6A and depicting the beginning of a breathing phase) in response to selection of the breathe again affordance 638. In some examples, the device uses the selected number of cycles of the completed breathing phase (e.g., restarts with the same settings).

In accordance with some embodiments, detecting completion of the breathing phase includes detecting that a predetermined amount of time has elapsed. For example, if three minutes elapses without an interruption, the user is assumed to have completed a breathing phase of 21 cycles at 7 cycles per minute.

In accordance with some embodiments, the completion interface further includes an indication of an estimated heart rate. For example, the exemplary completion interface shown in user interface screen 632 includes heart rate indicator 636, which is an exemplary indication of an estimated heart rate. In some examples, the heart rate indicator 636 pulsates on the display at a rate that corresponds to the estimated heart rate of the user.

In accordance with some embodiments, the device includes a sensor, and the device receives a first signal from the sensor during the breathing phase of the breathing sequence. The device determines the estimated heart rate based at least in part on the received first signal, and displays, on the display, an indication of the estimated heart rate. For example, the determined estimated heart rate is displayed as heart rate indicator 636 on user interface screen 632.

In accordance with some embodiments, the indication of the estimated heart rate is displayed subsequent to completion of the breathing phase. For example, user interface screen 632 of FIG. 6B, which includes heart rate indicator 636, is displayed subsequent to the completion of the breathing phase (e.g., after a progress indicator has fluctuated in accordance with the selected number of cycles as illustrated in user interface screens 620-628 of FIG. 6A).

Measuring the heart rate during the breathing exercise and displaying it afterward provides a high-fidelity reading of the user's resting heart rate, which can indicate the user's overall health or a current physiological state. If a user is breathing for relaxation, for example, providing an indication of an estimated heart rate increases the effectiveness of the breathing exercises by providing real-time (or nearly real-time) feedback of the user's physiological state, which can motivate the user to continue with another breathing exercise to achieve their relaxation goal.

In accordance with some embodiments, the first version of the progress indicator fluctuates at a first cyclic rate (e.g., 7 breaths per minute), and the aggregate amount of time is determined based at least in part on the first cyclic rate (e.g., 28 breaths completed divided by 7 breaths/minute is 4 minutes of breathing). For example, the aggregate amount of time is determined by dividing a completed number of cycles by the cyclic rate. For instance, if the first cyclic rate is 7 cycles per minute, and a completed number of cycles is 42, the aggregate amount of time is (42 cycles)÷(7 cycles per minute), which equals 6 minutes (depicted by indicator 634 in user interface screen 632). Cyclic rates are discussed in greater detail below, for example, with respect to user interface 640.

The device optionally displays a summary of an aggregate amount of time for each of a plurality of periods, for example, such as a weekly summary of the past 7 days. In accordance with some embodiments, the device determines an aggregate amount of time representing a completed number of cycles of the breathing sequence over a goal period for each of a plurality of goal periods. For example, the device determines a completed number of cycles for each day of the previous week (seven days). The device displays, on the display, a summary interface comprising an indicator for each of the plurality of goal periods, wherein the indicator for each of the plurality of goal periods represents the determined aggregate amount of time for its respective goal period of the plurality of goal periods. For example, user interface screen 642 of FIG. 6B depicts an exemplary summary interface, and includes an indicator for each goal period (e.g., indicators 646A and 646B), wherein each goal period is a day. Indicators 646A and 646B indicate the aggregate amount of time for the goal periods corresponding to Monday and Tuesday of the last week in the form of a bar chart. However, any visible representation suitable to indicate an aggregate amount of time can be used. A summary interface optionally includes an indicator of an aggregate amount of time for all periods of the plurality of goal periods. For example, indicator 644 indicates the total number of minutes of breathing performed over the last 7 days.

In accordance with some embodiments, the goal period is a day, and the plurality of goal periods is seven days.

As discussed briefly above, in accordance with some embodiments, the first version of the progress indicator fluctuates at a first cyclic rate. In some embodiments, a cyclic rate is a predetermined number of cycles per unit of time. In the example depicted at user interface screen 606, an exemplary first cyclic rate is 7 cycles per minute (e.g., breaths per minute). In some examples, the cyclic rate of a breathing sequence may be higher (e.g., which is generally less challenging for individuals) or lower (e.g., which is generally more challenging for individuals).

A user can optionally specify a cyclic rate of a breathing sequence. In accordance with some embodiments, the device receives a value of the first cyclic rate. For example, the device can receive the value via user input. In response to receiving the value of the first cyclic rate, the device sets the first cyclic rate to the received value. For example, user interface screen 640 of FIG. 6B depicts a configuration user interface similar to user interface screen 606 of FIG. 6A, but the cyclic rate value has been set to 5 cycles (e.g., breaths) per minute, as illustrated by indicators 608 and 610.

In accordance with some embodiments, the value of the first cyclic rate is set via user input received at the device. For example, the device can receive a touch input contact on a touch-sensitive surface or touch-sensitive display, the contact having a characteristic intensity that exceeds a threshold intensity and, in response, display a menu providing the user the ability to select a value. In this example, the device receives user selection of the value, and sets the value of the first cyclic rate to the selected value.

In some embodiments, the device is a first device, and the value of the first cyclic rate is received at the first device via transmission from a second device. The second device can be, for example, a smartphone paired to the device over one or more of a wired or wireless connection. For example, a user may select the value of the first cyclic rate using an application executed on a smartphone (e.g., the second device). In this example, the first device receives the value of the first cyclic rate via transmission from the smartphone over a wireless connection (e.g., via a Bluetooth connection, or any other suitable transmission protocol).

The cyclic rate (which can also be referred to as a breathing rate) associated with the breathing sequence can be a predetermined rate, a user-selected rate, or can be a rate associated with the breathing profile and/or health data associated with the user, as described above. For example, the device may access a user's breathing profile which, for example, indicates the user's baseline breathing rate, past breathing sequence settings, physiological signals, and the like. The device can use this information to select an appropriate cyclic rate for a breathing sequence. An appropriate cyclic rate, for example, can be the user's baseline breathing rate reduced by a predetermined amount (e.g., by a percentage).

In accordance with some embodiments, each cycle of the selected number of cycles includes a first period of time and a second period of time distinct from the first period. For example, FIG. 6C depicts an exemplary cycle 650 of user respiration, represented by a curve. In some examples, the curve represents the size of a progress indicator (e.g., as it fluctuates over time). The cycle 650 has a first period 664 (the time between points 652 and 656 of the respiration curve) and a second period 666 (the time between points 658 and 662 of the respiration curve). In this example, the first period 664 corresponds to an inhale period of the cycle, and second period 666 corresponds to an exhale period of the cycle. As shown, the first period 664 and the second period 666 of cycle 650 are distinct (e.g., they are unequal lengths of time). Points 656 and 658 are illustrated with a gap between them. As discussed above, this optional gap can be included in a cycle when determining the lengths of the inhale and exhale periods. This added duration of time represents the brief moment it takes for a person to switch between inhaling and exhaling. In some examples, there is no gap between points 656 and 658. In some examples, there is a gap between both transitions (e.g., between the transition from inhale to exhale, and between the transition from exhale to inhale).

In accordance with some embodiments, fluctuating the first version of the progress indicator includes: during each cycle of the selected number of cycles: changing, at the start of the first period of time, a first variable visual characteristic of the progress indicator; and changing, at the start of the second period of time, the first variable visual characteristic of the progress indicator.

In accordance with some embodiments, the first variable visual characteristic is the size of the displayed progress indicator, and wherein changing, at the start of the first period of time, the first variable visual characteristic includes increasing the size of the displayed progress indicator, and wherein changing, at the start of the second period of time, the first variable visual characteristic includes decreasing the size of the displayed progress indicator. As described above with respect to user interface screens 620-628, increasing and decreasing the size of a progress indicator provides a visual cue that coincides with a breathing pattern of the breathing sequence, and thus lowers the cognitive burden on the user to perform guided breathing exercises.

In accordance with some embodiments, the second period of time is greater than the first period of time. For example, period 666 is greater than period 664 in FIG. 6C. Thus, in this example, the exhale period is greater in length than the inhale period. A breathing pattern with unequal periods of inhale and exhale is important to the effectiveness of breathing exercises. The effectiveness of a breathing exercise is enhanced if the breathing pattern performed by the user is disruptive of the user's normal breathing pattern. For example, an individual's breathing pattern is typically composed of roughly equal inhale and exhale periods. However, for example, a breathing pattern that includes a longer exhale period than inhale period can increase the beneficial effects of to a user performing conscious breathing, such as increasing relaxation and decreasing anxiety. A ratio of the exhale period to the inhale period (also referred to as the "breath ratio") is preferably a value between 1:1.2 and 1:1.5, however the ratio can be lower or higher. In some embodiments, this ratio is configurable by user input. A higher ratio (exhale period relative to inhale period) is typically more difficult for an individual to learn and maintain. In some examples, the ratio value is set to 1:2.0. A user may specify the ratio of 1:2.0, for example, if they are an experienced conscious breather or desire to conduct a more challenging breathing sequence.

The breath ratio applicable to the breathing sequence may be included in a breathing profile. The breathing profile may be a default profile selected for all users, all new users, or defined for a particular user. For example, if the user has indicated via a setting, or otherwise, that she is a beginner breather a simpler ratio such as 1:1.2 or 1:1.5 may be the default. If the user has indicated that she is an advanced breather, a more difficult ratio such as 1:2 may be selected as the default. In some examples, the breathing profile may be particular to the user and may be configured via a setting or by collecting actual sensor data and estimating an appropriate breath ratio to be included in the user's breathing profile. For example, if the user participates in the preliminary phase of the breathing sequence (e.g., as discussed with respect to FIG. 6D below), the ratio may be determined based on the preliminary phase. In some examples, the user may participate in a practice breathing exercise to determine the breath ratio to be included in the breathing profile. The breathing profile may also include other information about the user. For example, the breathing profile may indicate metrics relating to breathing sequences completed by the user, breathing goals, and the like, any of which may be presented by an activity application running on the device and/or a second electronic device (e.g., a paired device). For example, the activity application may include a summary of activities performed and/or goals reached by the user during a time period (e.g., day, week, month, year, etc.). This summary can also include information about the breathing sequences completed by the user during the same time period. In some examples, the breathing profile may be determined for the user based on health information relating to the user. For example, health information, whether collected by the device or otherwise, may indicate certain health statistics (e.g., pulse rate, blood pressure, body temperature, respiratory rate, perspiration, etc.), and the health statistics may be used to determine an appropriate breathing profile for the user. In this manner, the breathing profile may be particularized to the user's health conditions, and may therefore be used as part of a plan for improving and/or addressing the health conditions. For example, if the health information indicates that the user has a higher-than-average respiratory rate, a breathing profile may be determined that aims to reduce the user's respiratory rate.

In accordance with some embodiments, fluctuating the first version of the progress indicator includes: displaying, on the display, the first version of the progress indicator in a first state; animatedly transitioning, during a first segment of time, the first version of the progress indicator from the first state to a second state; and animatedly transitioning, during a second segment of time, the first version of the progress indicator from the second state to the first state. For example, user interface screen 620 depicts a progress indicator in a first state (e.g., 50% of its size) and user interface screen depicts a progress indicator in a second state (e.g., 100% of its size), as shown in FIG. 6C. During the first segment of time (e.g., the first period 664), the progress indicator animatedly transitions (e.g., as shown in screen 622, which depicts an intermediate state between first and second states) from the first state to the second state. During the second segment of time (e.g., the second period 664), the progress indicator animatedly transitions (e.g., as shown in screen 626, which depicts an intermediate state between second and first states) from the second state back to the first state.

In accordance with some embodiments, the second segment of time is greater than the first segment of time. For example, second period 666 is greater than first period 664. In some examples, the periods may be switched, such that the longer period is the first period, and the short period is the second period. In some examples, the exhale period occurs before the inhale period during a cycle.

In accordance with some embodiments, prior to displaying the configuration user interface, the device determines whether a prompting criteria has been met. In accordance with a determination that the prompting criteria has been met, the device displays a prompt that includes a first affordance. The device receives user input selection of the first affordance, and in response, displays the configuration user interface. For example, the device may display a notification reminding the user to breathe, the notification including an affordance for launching (e.g., opening) an application used to conduct breathing sequences. The concepts related to displaying a prompt in accordance with a prompting criteria are described greater detail in the description of FIGS. 9A-9B below, and thus are not discussed in detail here.

In accordance with some embodiments, the device determines whether a prompting criteria has been met by determining whether a predetermined period of time has passed after a time associated with a previous breathing sequence. In some examples, the device sets and starts a timer for n number hours from the time associated with the previous breathing sequence, wherein n number of hours is the predetermined period of time related to the prompting frequency (e.g., if the prompting frequency is once every two hours, n is 2). In some examples, the device determines a time that is n number of hours from the time associated with the previous breathing sequence. The previous breathing sequence can be any breathing sequence that was previously accessed or displayed, by the device or an associated device. In some embodiments, the prompting criteria is met when the timer expires. In some embodiments, the prompting criteria is met when the determined time occurs.

In accordance with some embodiments, the time associated with the previous breathing sequence is a beginning time associated with the previous breathing sequence. In some embodiments, the beginning time associated with the previous breathing sequence can be the time of: display of the configuration user interface during the previous breathing sequence, or initiation of the breathing phase of the previous breathing sequence.

In accordance with some embodiments, the time associated with the previous breathing sequence is a completion time associated with the previous breathing sequence. In some embodiments, the completion time associated with the previous breathing sequence can be the time of: completion of a breathing phase of the previous breathing sequence, the display of a completion summary after completion of the breathing phase of the previous breathing sequence, or an exit from an application used to conduct the previous breathing sequence.

In accordance with some embodiments, prior to initiating the breathing phase of the breathing sequence, the device initiates a preliminary phase of the breathing sequence. For example, FIG. 6D includes user interface screens 668A-668E that depict a series of screens displayed during the preliminary phase of a breathing sequence. In some examples, the preliminary phase may be initiated after the user selects a start affordance at the configuration screen, but before the device initiates the breathing phase and fluctuates the first version of the progress indicator in accordance with the selected number of cycles.

In according with some embodiments, during the preliminary phase of the breathing sequence, the device displays a second version of the progress indicator and fluctuates the second version of the progress indicator in accordance with a preliminary number of cycles.

In some examples, the cycles of the preliminary number of cycles represent "training breaths". In some examples, the training breath cycles are in addition to the selected number of cycles (e.g., breaths) of the breathing phase. In some examples, the preliminary number of cycles is some small number of cycles, such as 2. By fluctuating a progress indicator for a few preliminary cycles before beginning a breathing phase, the preliminary phase provides the user with time to focus on and prepare their breathing in the moments before beginning a guided breathing exercise during the breathing phase. Furthermore, the preliminary phase provides visual cues (e.g., the fluctuation of the second version of the progress indicator) that the user can follow in order to gradually adjust (e.g., slow) their breathing in preparation for a breathing exercise, and use to synchronize their breathing to the breathing pattern of the breathing sequence. Thus, the full length of the breathing phase is utilized more effectively (e.g., the user is ready to breathe (e.g., is "warmed up") when the breathing phase starts) and the cognitive and physical burden of the user trying quickly to determine the correct pace and timing and adjust their breathing accordingly (e.g., if the breathing phase were to start suddenly without being preceded by the preliminary phase) is reduced. Accordingly, the preliminary phase increases the benefits of breathing sequences conducted in accordance with the embodiments described herein.

In the example depicted in user interface screens 668A-668E, an exemplary second version of the progress indicator (e.g., progress indicator 669) is shown. In this example, the second version of the progress indicator, progress indicator 669, is a version that fluctuates between 25% in size and 50% in size (e.g., relative to the size of the first version). Recall that in the example described in FIG. 6A, the first version of the progress indicator (e.g., progress indicator 616) fluctuates between 50% of its size and 100% of its size (e.g., in user interface screens 620-628). The difference in displayed appearance of the second version as compared to the first version provides a visual cue to the user that the device is currently in the preliminary phase. This visual cue improves the human-machine interface between the user and the device by intuitively notifying the user that they should be breathing along with the progress indicator, but that the actual breathing phase has not yet begun.

User interface screens 668A-668E are similar to user interface screens 620-628, in that they show fluctuation of a progress indicator over the course of one cycle. However the cycle of user interface screens 668-668E is a preliminary cycle, and the progress indicator displayed is a second version. In some examples, a preliminary cycle is shorter in length than a cycle used during the breathing phase (e.g., and thus can be more similar to normal breathing cycle). In some examples, a preliminary cycle has a different breath ratio as the cycles of the breathing phase (e.g., and thus can be more similar to a normal breathing ratio). The second version, as described above, is a reduced-size version of the first version of the progress indicator, yet fluctuates in a similar manner: the indicator is at its smallest at the beginning of a first period of the preliminary cycle (e.g., an inhale period), and is at its largest at the beginning of a second period of the preliminary cycle (e.g., an exhale period). Note that progress indicator 669 in user interface screen 668C is about 50% of the size of progress indicator 616 of user interface screen 624, though they are at the same relative point in their respective cycles (e.g., beginning of an exhale period). Thus, during the preliminary phase, the user is provided with a familiar visual cue (e.g., fluctuation of a progress indicator) that they can utilize to train their breathing, and additional visual indication that the device is in a training period (e.g., a second version that is a reduced size).

The second version of the progress indicator need not be a reduced size version of the first version. In some examples, the second version of a progress indicator can optionally pulsate, rotate, oscillate, disappear and reappear, or perform any other suitable graphical change during the preliminary phase. The aforementioned behavior is optionally different than the behavior of the first version of the progress indicator. In some examples, the first version of the progress indicator optionally exhibits one these aforementioned behaviors, in addition to, or in place of fluctuating. In some examples, a second version of a progress indicator fluctuates at a cyclic rate corresponding to an estimated breathing pattern (e.g., predefined, or measured from user health data).

Textual information is optionally provided during the preliminary phase. For example, textual information is displayed with the user interface screens 668A and 668B. User interface screen 668A includes textual information instructing the user to "Be still, and bring your attention to your breath". User interface screen 668B contains text instructing the user to "Now breathe along with the animation". In some examples, the textual information is displayed the first time that a user conducts a breathing sequence. The display of textual information provides the user with further visual cues which, when coupled with the other visual cues, functions to further reduce the cognitive burden on the user (especially new users) when conducting breathing sequences in accordance with the embodiments described herein.

In accordance with some embodiments, the device uses the preliminary phase to detect the user's breathing so that the device can synchronize the initiation of the breathing phase with the user's estimated breathing pattern. Synchronizing the initiation of the breathing phase is described in more detail below in the description of estimated breathing pattern 690 of FIG. 6F. For instance, in some examples, sensor data is collected during the preliminary phase that corresponds to heart measures and/or respiratory measures of the user. This sensor data can be used to determine an estimated breathing pattern of the user (e.g., a model of the user's breathing pattern during the preliminary phase or otherwise).

In accordance with some embodiments, the preliminary number of cycles is independent of the selected number of cycles. For example, the preliminary number of cycles is optionally a predetermined number of cycles. In accordance with some embodiments, the user can select the preliminary (e.g., predetermined) number of cycles.

In accordance with some embodiments, the first version of the progress indicator fluctuates at a first cyclic rate, and the second version of the progress indicator fluctuates at a second cyclic rate, which is greater than the first cyclic rate. For example, fluctuating a progress indicator at a cyclic rate which is closer to an individual's normal breath rate during the preliminary phase further increases the effectiveness of the preliminary phase by providing a transition between normal breathing and more challenging breathing (e.g., during the breathing phase). In some examples, a second cyclic rate is 12 cycles (e.g., breaths) per minute (closer to normal breathing), and greater than a first cyclic rate, which is 7 cycles per minute. These values are not intended to be limiting, and in other examples the first and second cyclic rates are any suitable values.

In accordance with some embodiments, the first version of the progress indicator includes a second variable visual characteristic. Examples of variable visual characteristics include the complexity, the color, the opacity of the displayed progress indicator, a number of displayed visual elements, and the like. Further in response to receiving the first user input, the device selects an initial state of the second variable visual characteristic in accordance with the selected number of cycles. For example, the visual complexity of the indicator may be dependent on (and thus selected in accordance with) the selected number of cycles.

Figure 6D:
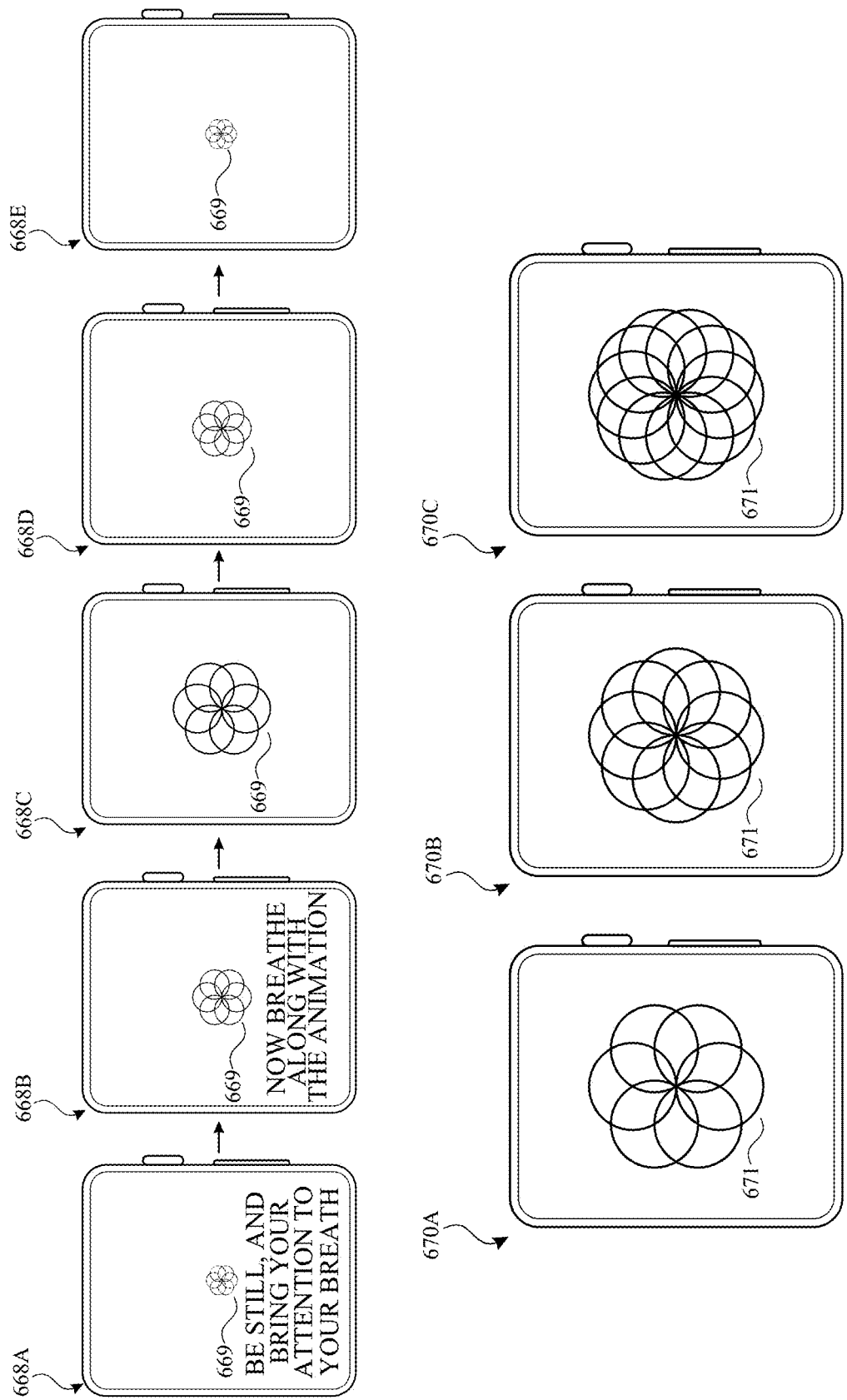
Figure 6E:
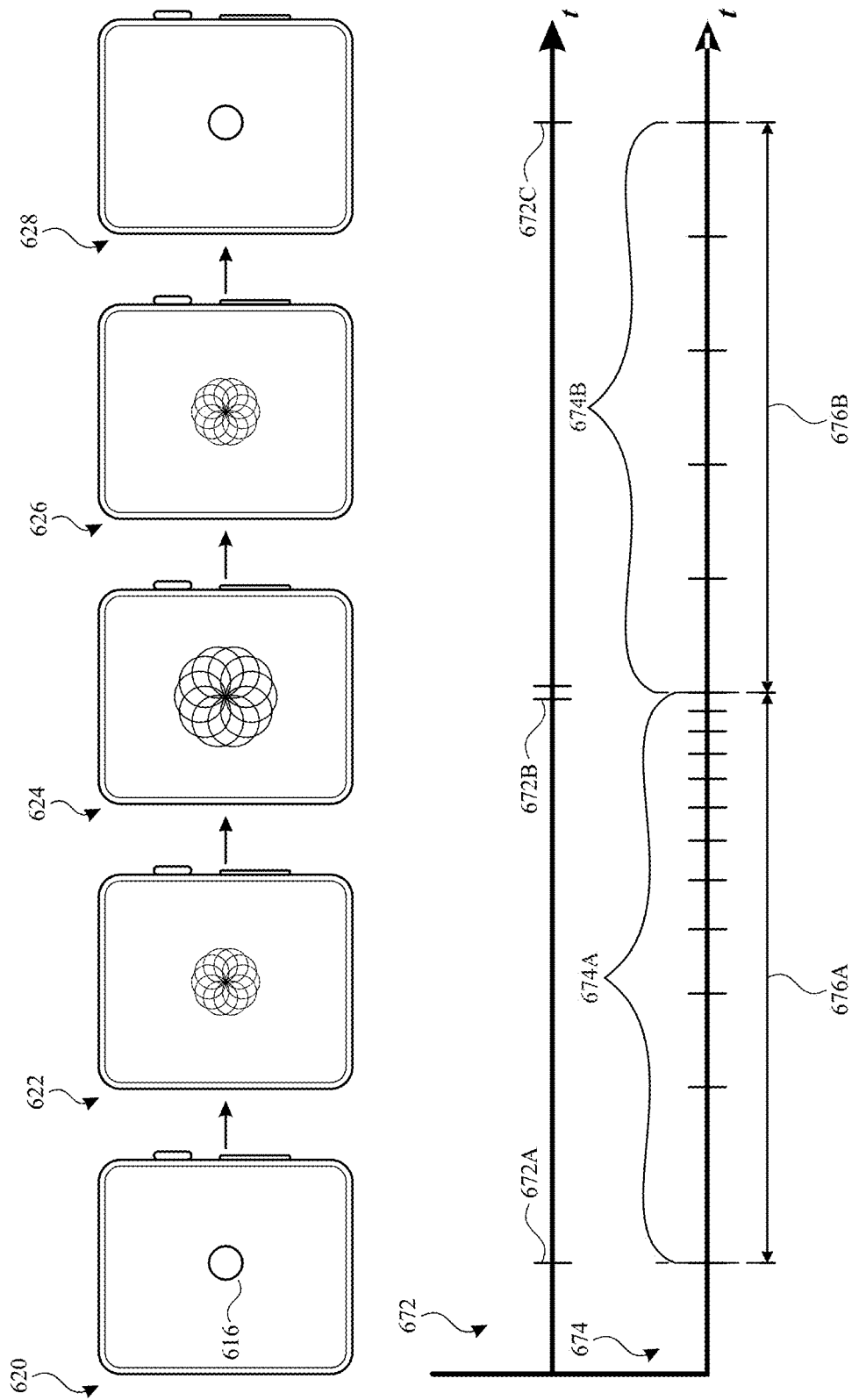

User interface screens 670A-670C of FIG. 6D depict an exemplary progress indicator 671 with a second variable visual characteristic (e.g., visual complexity level) selected based on the selected number of cycles. For instance, user interface screen 670A depicts progress indicator 671 created from six graphical elements (e.g., overlapping circles) when the selected number of cycles is set to seven. Screen 670B depicts progress indicator 671 created from eight graphical elements (e.g., overlapping circles) when the number of cycles is set to fourteen, and appears more visually complex. Screen 670C depicts progress indicator 671 created from ten graphical elements (e.g., overlapping circles) when the number of cycles is set to twenty-one, and appears more visually complex still.

In some examples, the variable visual characteristic is a variable visual element. Variable visual elements may take any form and be configured in any suitable manner. In some examples, the variable visual elements may be circular shapes (e.g., overlapping circles) aligned around a center point of the progress indicator 671 and may have at least some overlapping areas. In some examples, the variable visual elements may have any other suitable shape. In some examples, the variable visual elements may be partially transparent such that areas where the variable visual elements overlap may be darker than other areas. For example, an area with no overlap may be the most transparent, followed by areas with more overlap having increasingly less transparency. In this manner, the center of the progress indicator 671 may appear darker than the outer edges (e.g., due to circles overlapping).

In accordance with some embodiments, during the breathing phase of the breathing sequence, the device detects completion of a portion of the selected number of cycles and, in response, changes the second variable visual characteristic of the progress indicator. In some examples, changing the second variable visual characteristic includes reducing the complexity of the progress indicator. For example, if a user selected a number of cycles equal to 21, the first version of the progress indicator initially displayed after initiation of the breathing phase can resemble the ten graphical element progress indicator 671 of user interface screen 670C. Upon detecting completion of a portion of the selected number of cycles (e.g., detecting that 7 cycles have been completed), the complexity of the displayed progress indicator may be reduced. In some examples, the reduced complexity first version of the progress indicator can resemble the eight graphical element progress indicator 671 of user interface screen 670B after detecting completion of 7 cycles, thus matching the appearance of the progress indicator corresponding to 14 cycles (e.g., the initial complexity of a progress indicator when 14 cycles is selected initially).

In accordance with some embodiments, the device detects completion of the portion of the selected number of cycles by determining whether the progress indicator has fluctuated in accordance with a predetermined number of cycles. In some examples, the device detects completion of a particular number of cycles. For instance, as in the example above, the device determines that the progress indicator has fluctuated in accordance with 7 cycles, and thus changes the second variable visual characteristic (e.g., reduces the complexity) of progress indicator 671 from ten graphical elements to eight graphical elements.

In accordance with some embodiments, the device detects completion of the portion of the selected number of cycles by detecting whether a predetermined amount of time has passed during the breathing phase of the breathing sequence.

For instance, using the example above, the device determines (e.g., detects) that the progress indicator has fluctuated for an amount of time equal to one minute, and in response, changes the second variable visual characteristic. As should be apparent, in the example described, because the cyclic rate is set to 7 cycles per minute, the effect would be the same (e.g., the second variable visual characteristic is changed after one minute, which is equivalent to 7 cycles in this example).

In some embodiments, detecting whether a predetermined amount of time has passed during the breathing phase includes setting a timer equal to the predetermined amount of time, and detecting whether the timer has expired. For example, the device can set and start a timer equal to one minute in response to initiation of the breathing phase, and change the second variable visual characteristic in response to the timer expiring. In some embodiments, detecting whether a predetermined amount of time has passed during the breathing phase includes determining a second time that is the predetermined amount of time after a first time, and detecting whether the second time has occurred. For example, if the breathing phase is started at 8:00 AM, the device can determine that the second variable visual characteristic will be changed at 8:01 AM, and do so when it detects that this latter time has occurred.

In accordance with some embodiments, the first version of the progress indicator includes a plurality of graphical elements, and wherein to change the second variable visual characteristic of the progress indicator, the device changes a number of the displayed graphical elements of the plurality of graphical elements. For example, referring back to the example described above describe with respect to 670A-670C, the device may reduce the number of graphical elements displayed from 10 (e.g., as in screen 670C) to 6 (e.g., as in screen 670A) during the breathing phase.

In accordance with some embodiments, the device includes a haptic output device and, during the breathing phase of the breathing sequence, the device outputs one or more haptic breathing cues according to a haptic profile. An exemplary haptic breathing cue is a discrete haptic output (e.g., a vibration) for a short duration (e.g., less than one second). These cues can serve as signals (to a user) of the current period and progress of a cycle of the breathing sequence, such as beginning or end of inhale or exhale periods during the breathing sequence. In some examples, a haptic breathing cue is continuous and for a longer duration.

A haptic breathing profile refers to the pattern and/or timing of haptic breathing cues during a breathing sequence. In some examples, depending on the active haptic breathing profile, the device outputs haptic breathing cues at one or more of: the initiation of a breathing phase inhale period, during the inhale period, at the initiation of the breathing phase exhale period, and during the exhale period. This list is not exhaustive, and other cues are contemplated by this disclosure.

The output of haptic breathing cues by the device improves the human-machine interface between a user and the device, because the user can perceive breathing cues corresponding to the breathing sequence by touch (e.g., by vibrations), which provides strong non-visual reinforcement of the pattern of a breathing sequence. In this way, the haptic breathing cues can increase the effectiveness of breathing exercises conducted in accordance with a breathing sequence as describe herein. For example, if a user is conducting a breathing sequence in order to relax, the user can following along with the breathing sequence using the haptic breathing cues while keeping their eyes closed, further increasing their relaxation. In some examples, the output of haptic breathing cues allows a user to follow along with a breathing sequence when they cannot see the display (e.g., in bright sunlight, or if the user is visually impaired), or when illumination from the display is distracting or undesired (e.g., during a meeting, or in a dark theater), or when the user cannot safely view the display to follow along with a displayed progress indicator (e.g., while driving). In some examples, the device is a wearable device, such as an electronic watch, and during the output of haptic breathing cue (e.g., a vibration) the user would feel a buzzing sensation on their wrist.

In accordance with some embodiments, to output the one or more haptic breathing cues according to the haptic profile, the device outputs a first plurality of haptic breathing cues at a first frequency between cues during a first period of time (e.g., the inhale period), and the device outputs a second plurality of haptic breathing cues at a second frequency between cues during a second period of time (e.g., the exhale period). For example, the frequency between cues refers to the time between the output of discrete haptic breathing cues.

In accordance with some embodiments, the first frequency between cues is an increasing frequency, and the second frequency between cues is a constant frequency. This is referred to as a "crescendo" haptic profile and is illustrated graphically at haptic profile diagram 674 of FIG. 6E, which depicts one cycle. User interface screens 620-628 are reproduced in FIG. 6E, and are aligned with haptic profile diagram 674. Haptic profile diagram 674 has an axis t representing time, and a plurality of vertical lines along the axis, each representing the time of an output of a discrete haptic cue. Haptic profile diagram 674 is shown under the user interface screens 620-628. Each screen 620-628 is positioned along the axis t and aligns with the respective time during the cycle at which each screen would be displayed by the device during a breathing phase of a breathing sequence. During the first period 676A, which can represent the inhale period of a cycle (e.g., breath), the device outputs haptic breathing cues 674A, wherein each cue is represented by a vertical mark on axis t of diagram 674. As can be seen, the spacing between each of haptic breathing cues 674A gets smaller as the time during the first (e.g., inhale) period 676A progresses—thus, the frequency between cues is increasing. Accordingly, the haptic breathing cues 674A are output at an increasing frequency between cues. At the end of the first period (corresponding to the time on axis t aligned with screen 624), the second period 676B begins. During the second period (e.g., the exhale period), the device outputs haptic breathing cues 674B at a constant frequency—that is, the period of time between the output of each of haptic breathing cues 674B is the same. The distinction in frequency between haptic breathing cues during the inhale and exhale periods provides a non-visual cue to the user, indicating the position and progress of the breathing sequence during a cycle. For example, as the frequency between cues gets higher, the user knows that the inhale period is coming to an end and that they should prepare to exhale.

In accordance with some embodiments, to output the one or more haptic breathing cues according to the haptic profile, the device outputs, at the start of the first period of time, a first number of haptic breathing cues, and outputs, at the start of the second period of time, a second number of haptic breathing cues. In accordance with some embodiments, the first number and the second number are different. This is referred to as the "one tap, two tap" haptic profile and is illustrated graphically at haptic profile diagram 672. Haptic profile diagram 672 has an axis t representing time, and a plurality of vertical lines along the axis, each representing the time of an output of a discrete haptic cue. Haptic profile diagram 672 is shown under user interface screens 620-628, and depicts one cycle. Similar to haptic profile diagram 674 described above, each screen 620-628 is positioned along the axis t and aligns with the respective time during the cycle at which each screen would be displayed by the device during a breathing sequence. At the beginning of the first period 676A, which can represent the inhale period of the cycle (e.g., breath), the device outputs one haptic breathing cue 672A, wherein the cue is represented by a vertical mark on axis t of diagram 672. At the end of the first period (corresponding to the time on axis t aligned with screen 624), the second period 676B begins. At the beginning of the second period (e.g., the exhale period), the device outputs two haptic breathing cues 672B. Haptic breathing cue 672C, similar to 672A, and represents the beginning of a new period. Thus, the one tap, two tap haptic profile can provide a minimal number of haptic outputs yet still signal to a user the transition between inhale and exhale periods. Accordingly, the benefits of the non-visual breathing training provided by the haptic breathing cues is still achieved, while potentially reducing power consumption of the device.

In accordance with some embodiments, the device suppresses, during the breathing phase of the breathing sequence, the output of at least a subset of alerts that the device is configured to output. For example, during the breathing phase, the device may suppress some or all audible, visible, or haptic alerts not associated the breathing sequence. For example, these alerts are generated by the device receiving a phone call, the device receiving an electronic message (e.g., SMS, email, or iMessage), a scheduled alarm, a reminder, a calendar event, a notification (e.g., from a news application on the device), or the like. Suppressing some or all alerts that the device is configured to generate, prevents potential interruptions to a user conducting a breathing sequence, and allows the user to focus on the breathing sequence and not be disturbed, thereby increasing the benefits of conducting breathing sequences in accordance with the embodiments described herein.

While conducting a breathing sequence, a user may cause the breathing sequence to be interrupted. In accordance with some embodiments, during the breathing phase of the breathing sequence, the device receives a user input (e.g., representing an interruption), and the device determines whether the user input meets a breathing sequence interrupt criteria. For example, the device can detect that a user has navigated away from a breathing application (e.g., exited, switched applications) being used to conduct a breathing sequence, that a user started physical activity (e.g., walking), that the user has answered a phone call on the device or on a coupled device, or any other condition that indicates that the user is not performing a breathing exercise in accordance with the breathing sequence.

Figure 6F:
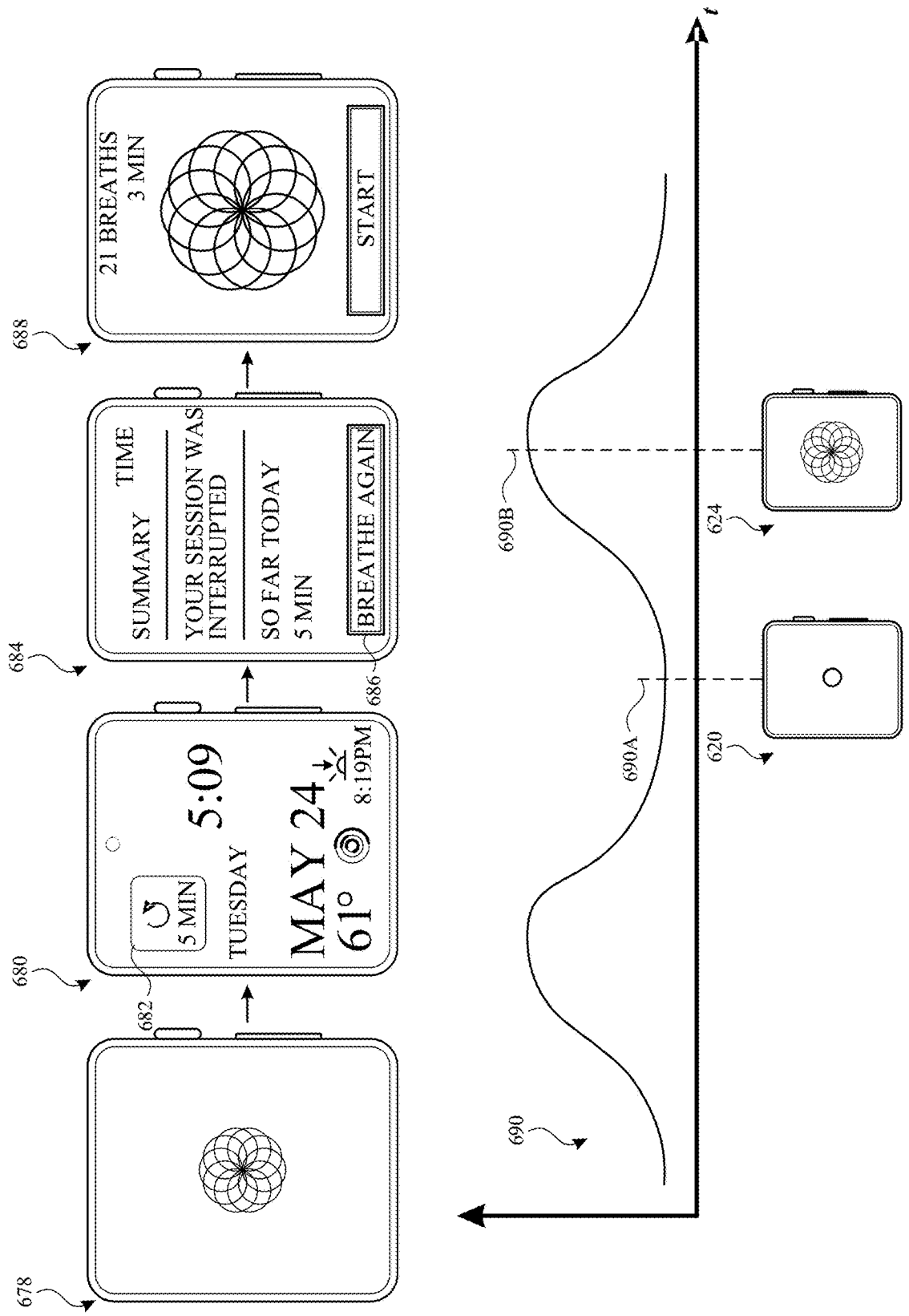
Figure 7A:
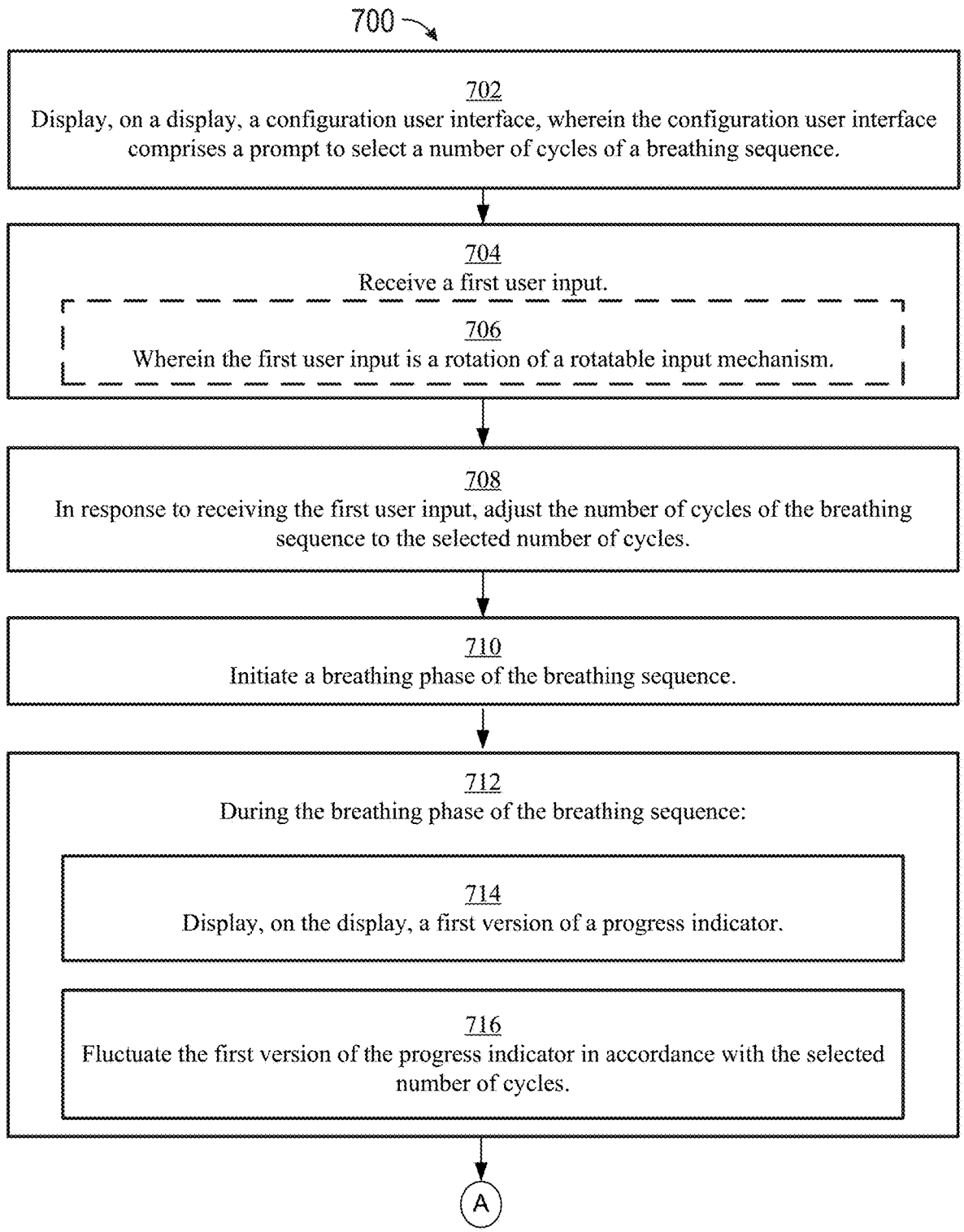
Figure 7B:
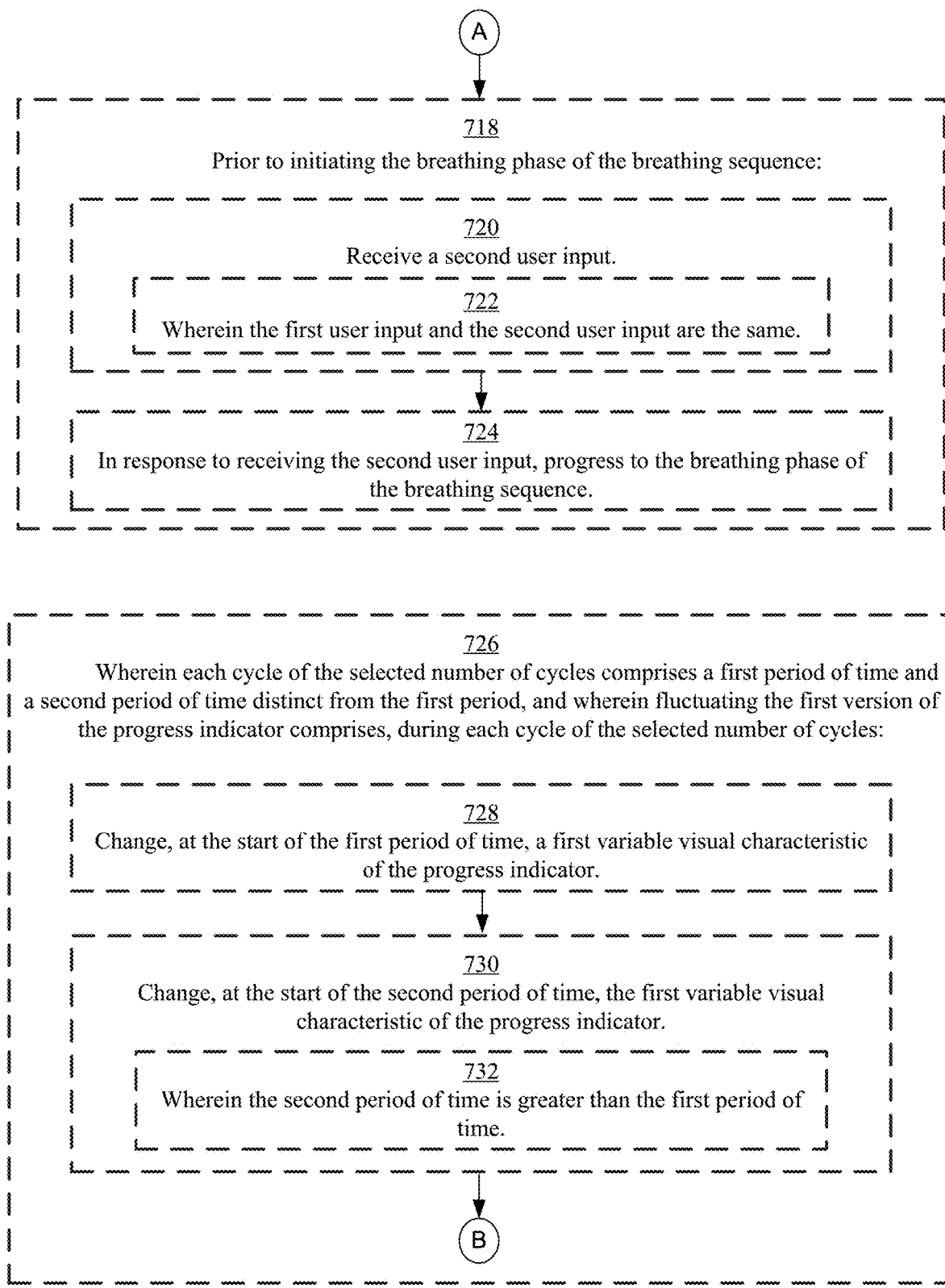
Figure 7C:
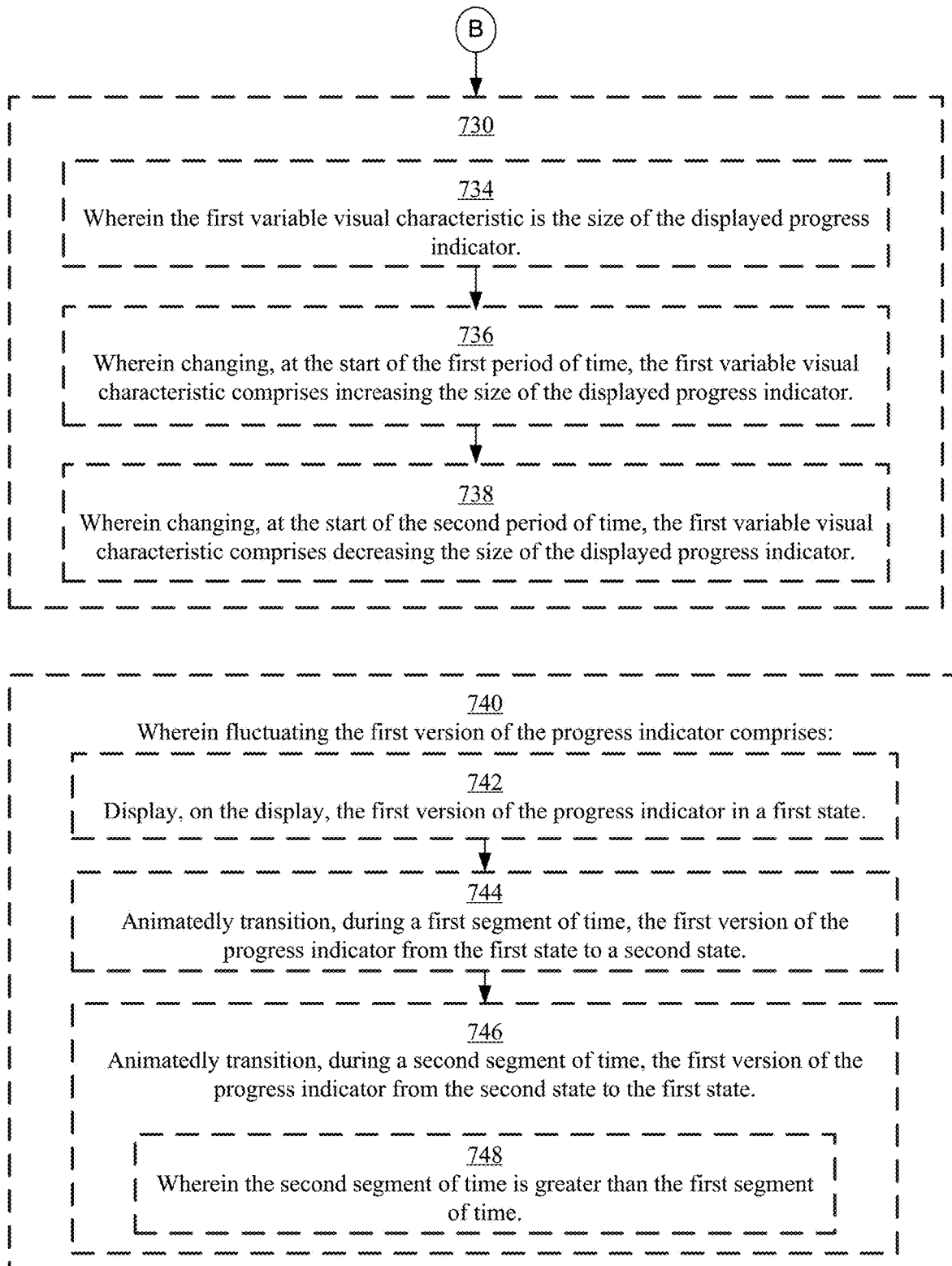
Figure 7D:
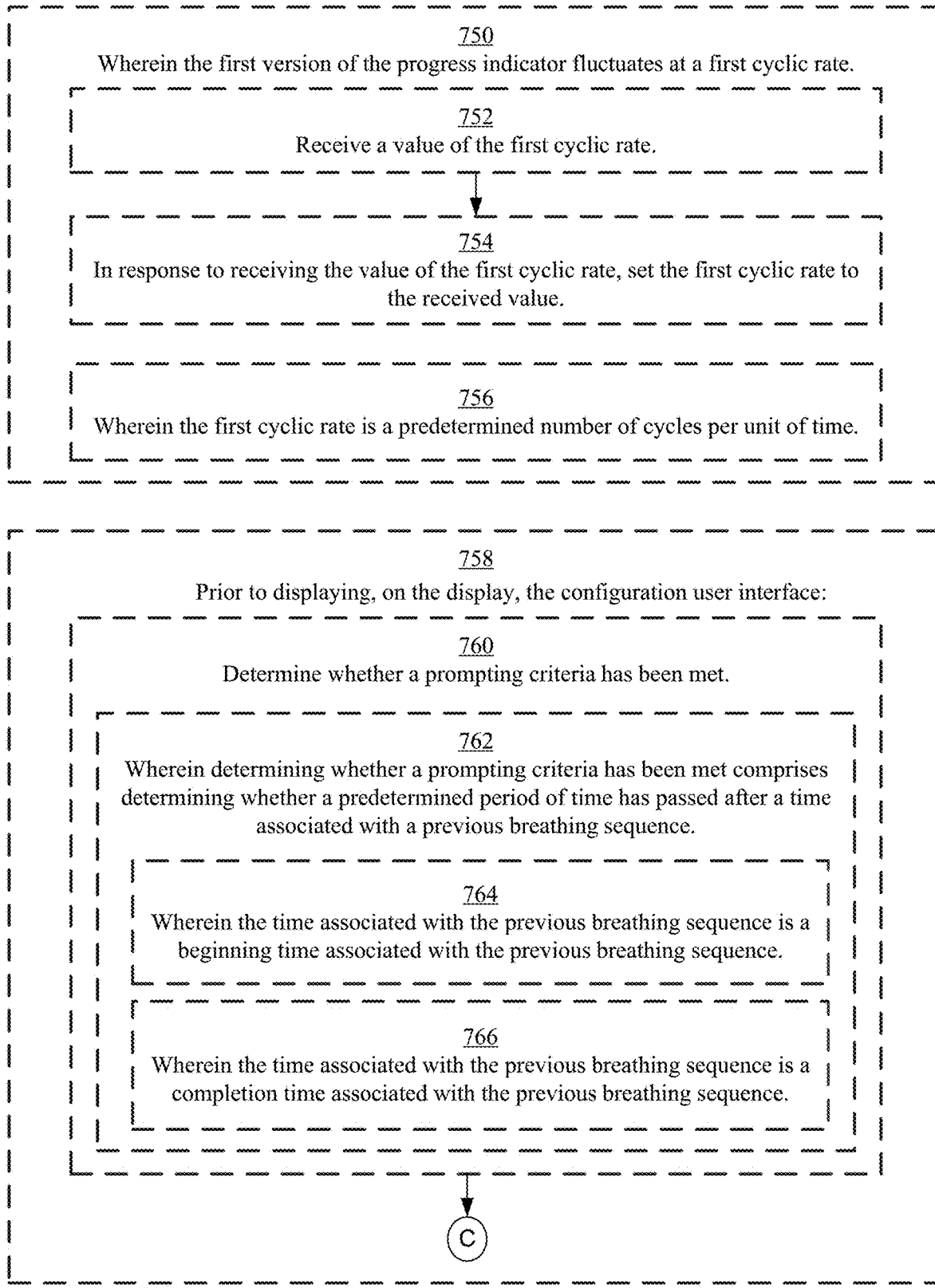
Figure 7E:
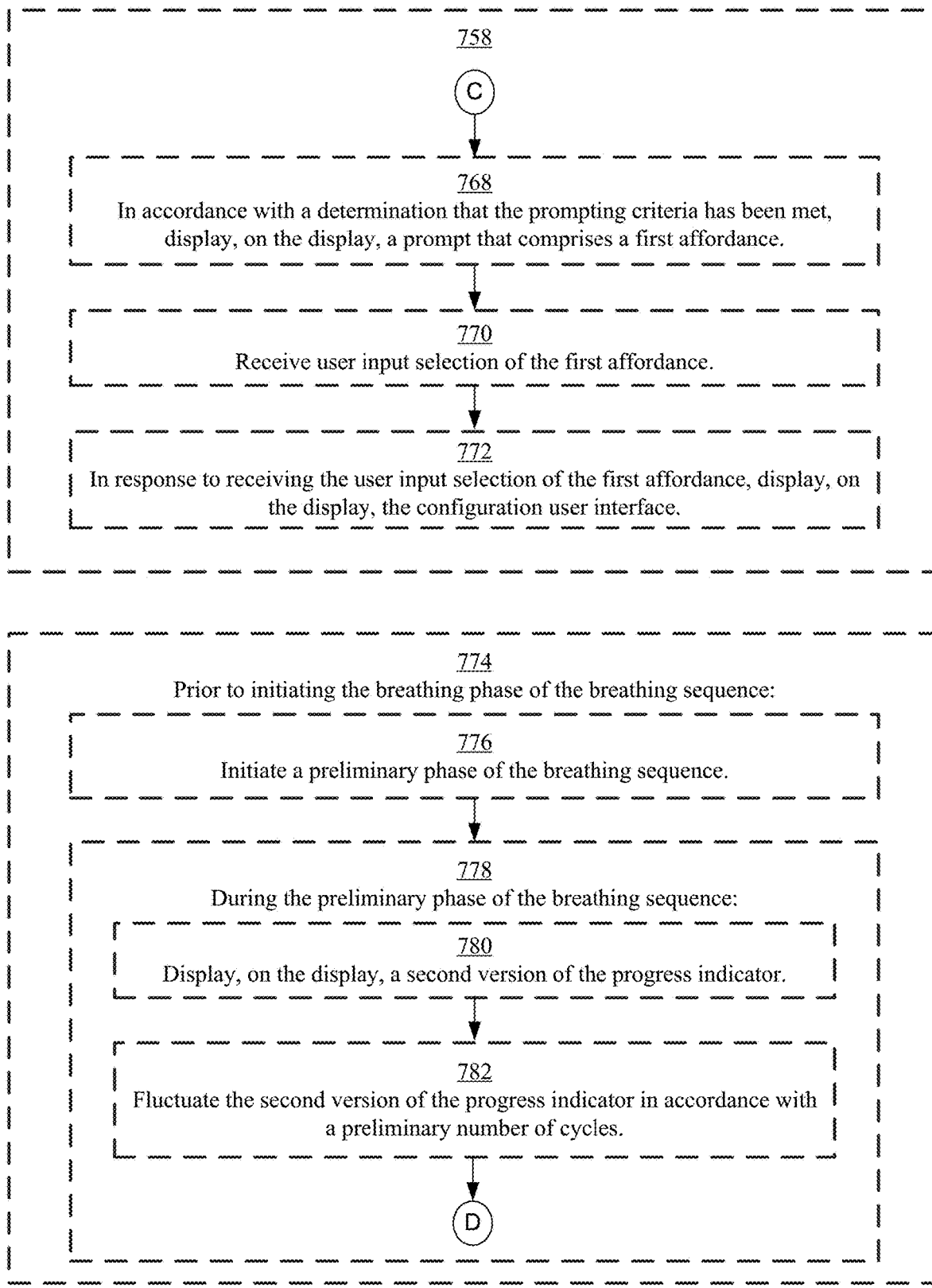
Figure 7F:
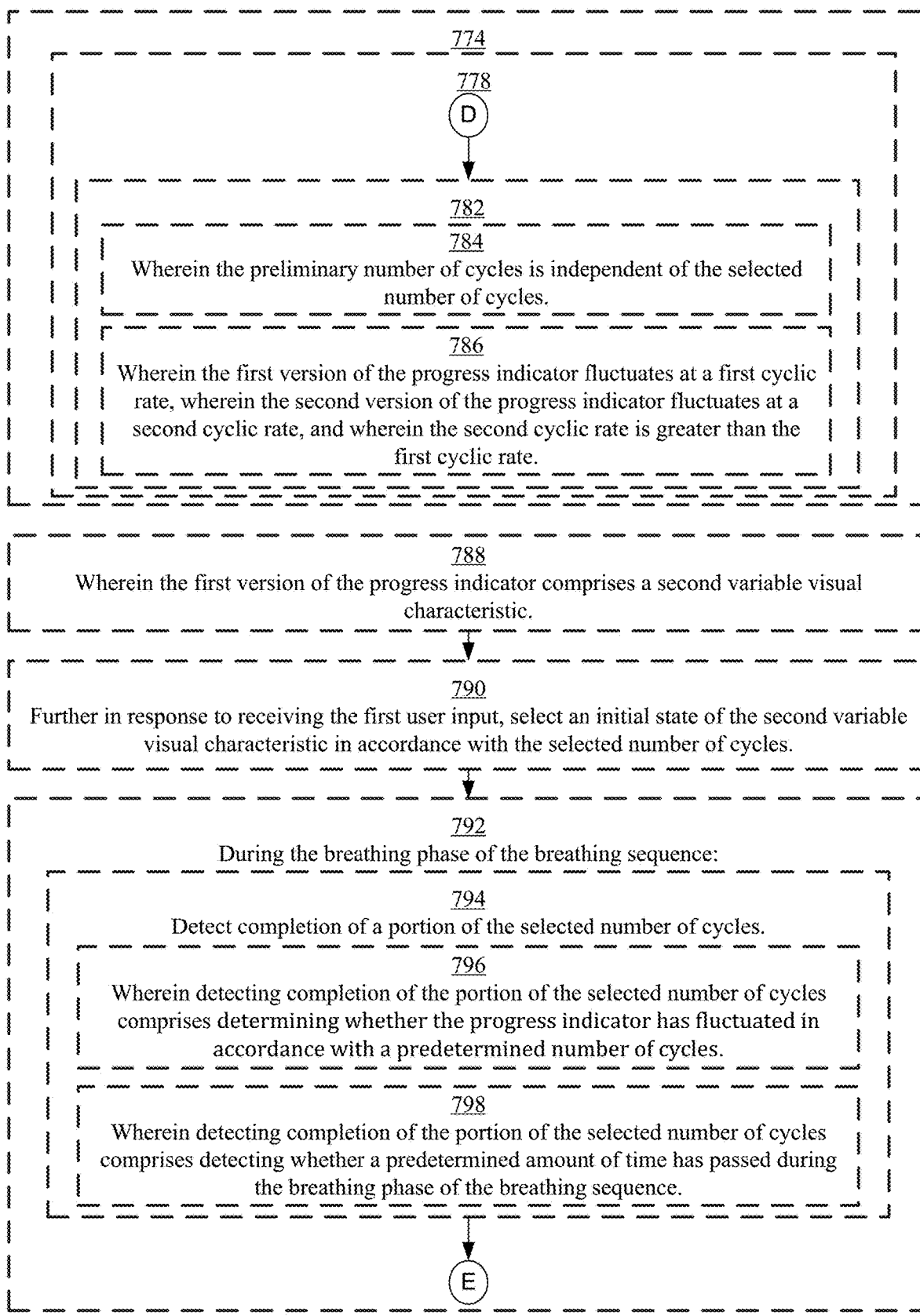
Figure 7H:
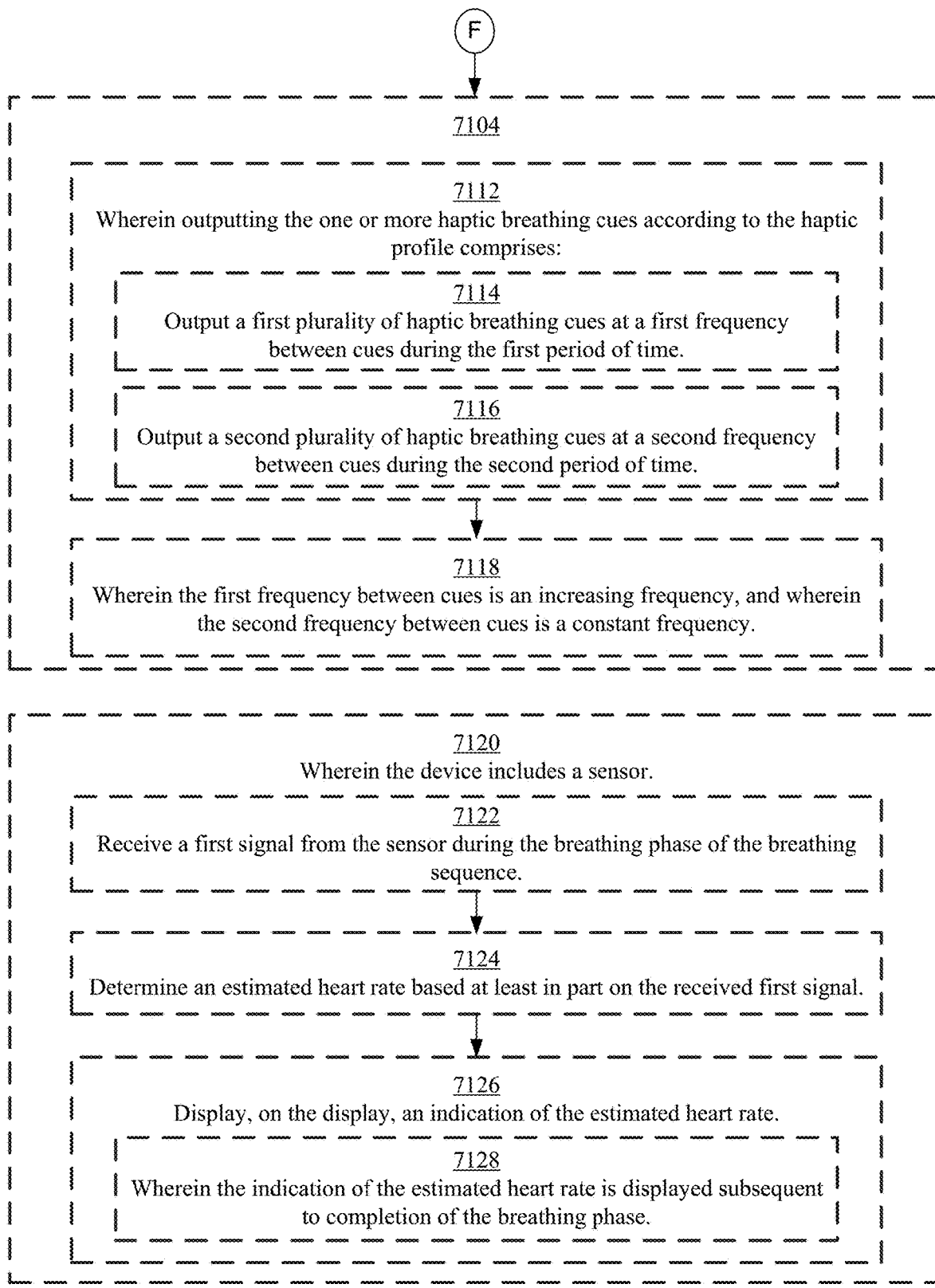
Figure 7I:
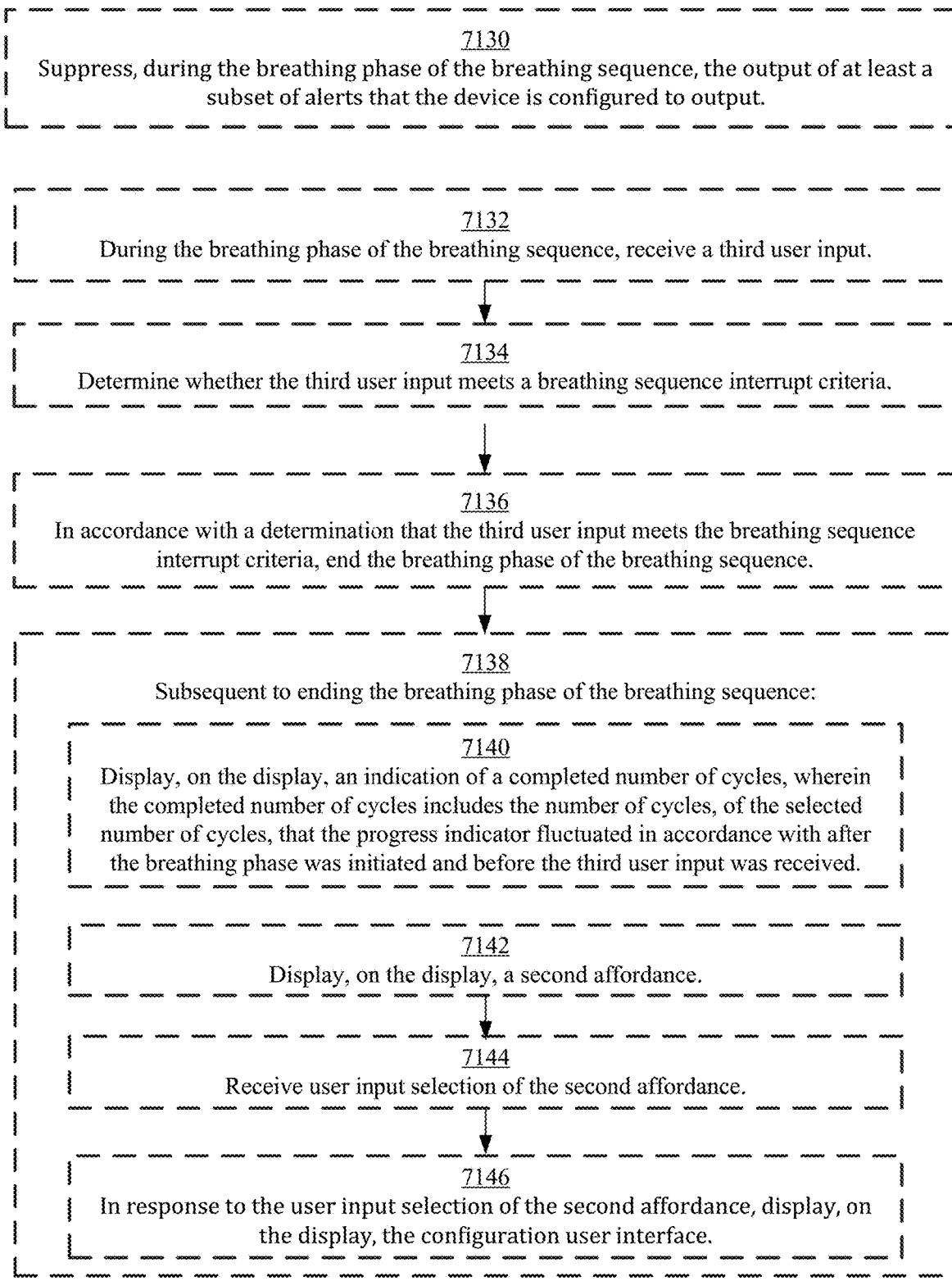
Figure 7L:
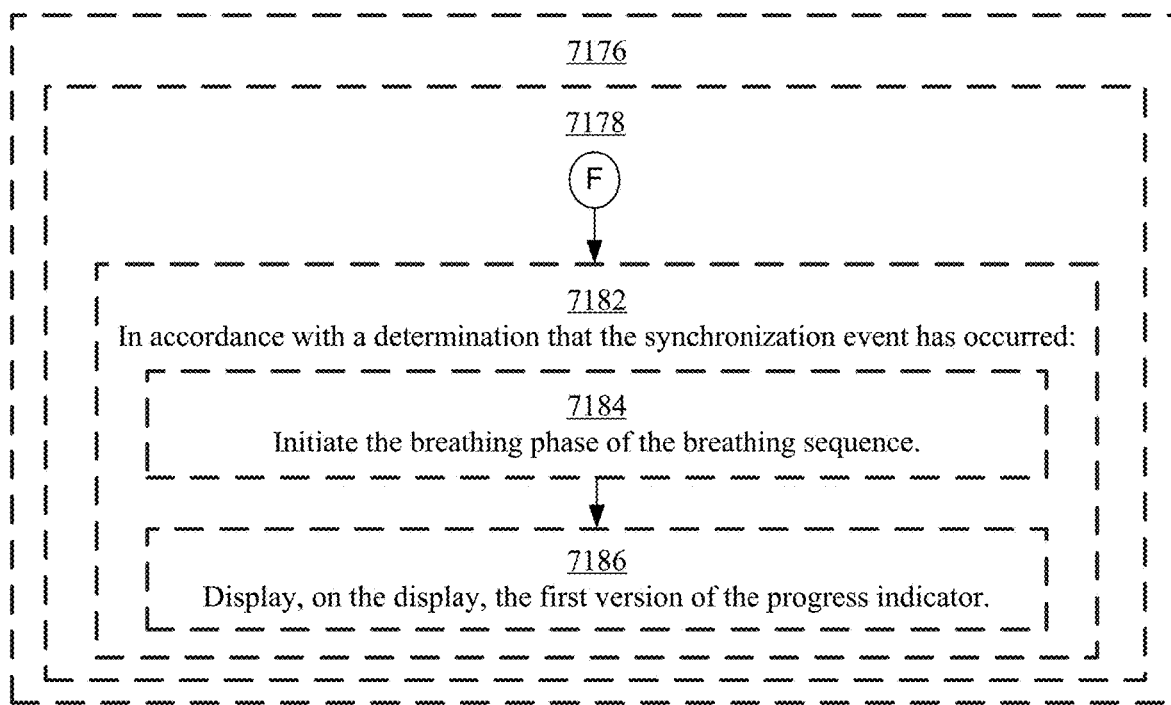
Figure 7L:
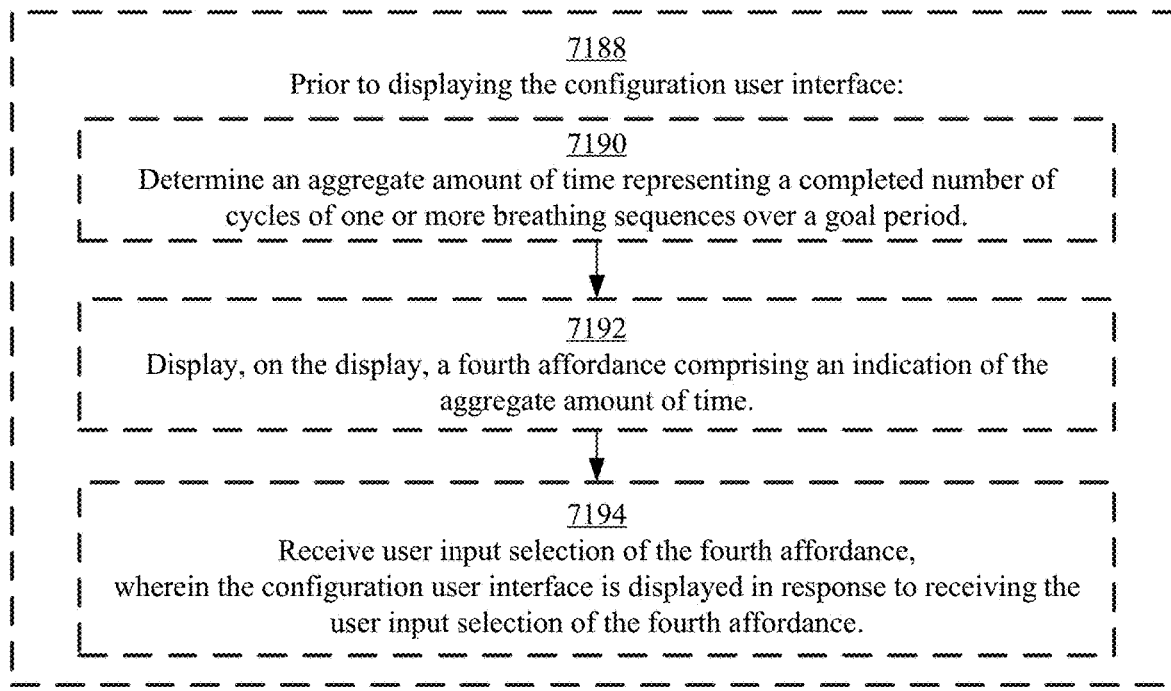

User interface screen 678 of FIG. 6F depicts a progress indicator displayed during a breathing phase of a breathing sequence. In this example, the device receives user input while displaying user interface screen 678, wherein the user input represents a request to display a home screen of the device. In response to the input, for example, the device displays user interface screen 680, which depicts an exemplary home screen of the device that includes affordance 682.

In accordance with a determination that the user input meets the breathing sequence interrupt criteria, the device ends the breathing phase of the breathing sequence. For example, even though a program being used to conduct the breathing sequence may be still be open as a background application after the interrupting user input is received (e.g., causing the home screen to be displayed), the device ends the breathing sequence. In this way, the breathing phase does not continue when the device detects a condition indicating that the user is likely not following along with the breathing sequence.

Subsequent to ending the breathing phase of the breathing sequence, the device displays, on the display, an indication of a completed number of cycles. In some examples, the completed number of cycles includes the number of cycles, of the selected number of cycles, that the progress indicator fluctuated in accordance with after the breathing phase was initiated and before the user input (e.g., causing the breathing phase to end) was received. For example, if a user causes the device to re-display the application (used for conducting breathing sequences) for the first time subsequent to receiving the user input (e.g., representing the interruption), the device displays the amount of breathing that the user completed before the interruption.

The amount of breathing can be displayed, for example, on an interrupted session user interface. An exemplary interrupted session user interface is depicted in user interface screen 684 of FIG. 6F. User interface screen 684 includes textual information informing the user that the previous breathing sequence (e.g., session) was interrupted, as well as the amount of breathing (e.g., "SO FAR TODAY 5 MIN").

In some examples, the amount of breathing is the total breathing for the current day. Alternatively, in some examples the amount of breathing is the total breathing completed during the interrupted breathing sequence. In some examples, if the user interrupts the breathing phase after 7 cycles, and the selected number of cycles is 21 at a cyclic rate of 7 cycles per minute, the indication of the completed number of cycles includes the 7 cycles (e.g., breaths), or alternatively one minute (e.g., (7 cycles)÷(7 cycles per minute)), which the user completed before the breathing sequence was interrupted. In some examples, the completed number of cycles can also include the total number of completed cycles for a period of time, such as today. For example, if the user previously completed 28 cycles in the current day, in addition to the 7 cycles during the interrupted breathing phase, the indication of the completed number of cycles can include 35 cycles, five minutes (e.g., (35 cycles)÷(7 cycles per minute)), or both. This example is illustrated at user interface screen 684, which depicts an indication of the number of completed cycles ("SO FAR TODAY 5 MINS"). As discussed above, the indication of the completed number can also be a number of cycles (not depicted) (e.g., "SO FAR TODAY 35 BREATHS").

In accordance with some embodiments, subsequent to ending the breathing phase of the breathing sequence, the device displays, on the display, a second affordance (e.g., for conducting another breathing sequence). For example, user interface screen 684 includes an exemplary second affordance, breathe again affordance 686. The device receives user input selection of the second affordance and, in response, displays, on the display, the configuration user interface. For example, in response to receiving selection of breathe again affordance 686, the device displays user interface screen 688, depicting an exemplary configuration screen. At the configuration user interface, the user can select a new number of cycles and cause the device to progress to a new breathing phase.

By returning the user to the configuration user interface after selection of a breathe again affordance, the user is provided several options for resuming a breathing exercise after an interruption. The user can, for example, select the number of cycles for the new sequence to be equal to the number of cycles remaining in the previous sequence before it was interrupted. For instance, if the user had completed 7 cycles of a 21 cycle breathing phase, the user can set the number of cycles for a new breathing phase to 14 cycles, in order to complete the original goal of 21 cycles (e.g., 7 cycles+14 cycles). Alternatively, the user may elect to conduct a breathing sequence with the full 21 cycles again. In accordance with some embodiments, in response to receiving user input selection of the second affordance, the device can automatically progress to a new breathing sequence. For example, during the new breathing phase, the device can fluctuate the progress indicator in accordance with the previously-selected number of cycles (of the interrupted breathing phase). Allowing the user to bypass the configuration user interface, and automatically progress to a new breathing sequence, reduces the number of user interfaces displayed, thereby reducing cognitive burden on the user, and saving time and device resources.

In accordance with some embodiments, the device receives a second signal during the breathing sequence. For example, the second signal can represent health data or measurements usable to determine a user's estimated breathing pattern. The device determines an estimated breathing pattern based at least in part on the received second signal, and synchronizes the initiation of the breathing phase of the breathing sequence and the display of the progress indicator during the breathing phase of the breathing sequence with the estimated breathing pattern. For example, the device determines the user's estimated breathing pattern based on a signal representing the user's respiration (or usable to calculate the user's respiration), and then synchronizes the beginning of the breathing phase with the appropriate time during the user's estimated breathing pattern.

In accordance with some embodiments, the device includes a sensor, and receives the second signal from the sensor during the breathing sequence. Exemplary techniques for measuring user respiration and determining a breathing pattern are found, for example, in the related applications U.S. Provisional Application Ser. No. 62/348,804, entitled "Breathing Synchronization and Monitoring", filed on Jun. 10, 2016; and U.S. Provisional Application Ser. No. 62/348, 808, entitled "Fluctuating Progress Indicator", filed on Jun. 10, 2016. The content of these applications is hereby incorporated by reference in their entirety for all purposes.

In some examples, the device collects health data. The health data is optionally collected using one or more sensors of the device. In some examples, the device determines respiratory measures based at least in part on the health data. The respiratory measures include, for example, a breathing pattern (e.g., a cyclic pattern of inhale breaths and exhale breaths), a breathing rate (e.g., a number of full breaths taken during a time period), a breath ratio (e.g., a comparison of time allocated to inhale breaths compared to exhale breaths), and any other related measure. In some examples, using the respiratory measures, the device generates breathing cues. For example, the device presents a breathing element (e.g., a progress indicator) to lead a breathing sequence in accordance with the breathing cues, and as discussed throughout this specification. For example, the breathing element is optionally a fluctuating progress indicator, various versions of which can be presented on a display of the device to lead the user in the breathing sequence.

FIG. 6F depicts exemplary estimated breathing pattern 690, represented by a curve. Exemplary estimated breathing pattern 690 represents an approximation of the respiration of a user over time. In some examples, the curve represents the size of a progress indicator (e.g., as it fluctuates over time). Point 690A of estimated breathing pattern 690 represents a transition between the end of an exhale period (sloping down and to the right) and the beginning of the inhale period (sloping up and to the right). Using estimated breathing pattern 690, the device can determine the occurrence of the transition event in order to synchronize the breathing phase such that it is initiated to match the user's estimated breathing pattern. For example, if a breathing phase begins with an inhale period (e.g., the progress indicator growing in size), the device will initiate the breathing phase at the point 690A in the estimated breathing pattern 690, representing an estimate of when the user is beginning their inhale. In some examples, the point 690B representing the transition between the end of the inhale period and the beginning of the exhale period can be used. For instance, if a breathing phase begins with an exhale period (e.g., the progress indicator shrinking in size), the device will initiate the breathing phase at the point 690B in the estimated breathing pattern 690, representing an estimate of when the user is beginning their exhale. User interface screens 620 and 624 (representing the progress indicator at its smallest and largest relative sizes, respectively, for the breathing phase fluctuations illustrated in FIG. 6A) are included for reference to illustrate examples of what is displayed by the device at each of the respective points 690A and 690B.

In some examples, the device determines the estimated breathing pattern during the preliminary phase. During the preliminary phase the device can be receiving signal data from the one or more sensors. Based at least in part on the signal data, the device can estimate an estimated breathing pattern corresponding to the user of the device. As described throughout, the breathing pattern may be a cyclic pattern of breath events (e.g., inhale, exhale) and times corresponding to the breath events. For example, the cyclic pattern may include a series of inhale breath events and a series of exhale breath events. In some examples, the preliminary phase may continue at least until the device is able to estimate a breathing pattern (e.g., to determine an estimated breathing pattern) or may continue for a fixed time or until a fixed number of breaths have been identified (e.g., for a preliminary number of cycles).

In accordance with some embodiments, to synchronize the initiation of the breathing phase of the breathing sequence and the display of the progress indicator during the breathing phase of the breathing sequence with the estimated breathing pattern, the device determines a synchronization event that is a transition between an inhale period and an exhale period of the estimated breathing pattern. An exemplary synchronization event is a transition between an inhale period and an exhale period. For example, the device can determine either of points 690A and 690B as an exemplary synchronization event. In accordance with a determination that the synchronization event has occurred, the device initiates the breathing phase of the breathing sequence, and displays, on the display, the first version of the progress indicator. For example, as illustrated in FIG. 6F, the device may display user interface screen 620, depicting an exemplary first version of a progress indicator, at point 690A, and proceed to fluctuate the progress indicator in accordance with the operations described with respect to screens 620-628 of FIG. 6A.

In accordance with some embodiments, prior to displaying the configuration user interface, the device determines an aggregate amount of time representing a completed number of cycles of one or more breathing sequences over a goal period. For example, the device determines the total breathing time completed for today. The device displays, on the display, a fourth affordance comprising an indication of the aggregate amount of time. For example, if the device is an electronic watch, the fourth affordance can be a selectable watch face complication that includes the number of minutes of breathing completed today. The device receives user input selection of the fourth affordance and, in response to receiving the user input selection of the fourth affordance, displays the configuration user interface. For example, in response to selection of the watch face complication, the device launches a breathing application for conducting breathing sequences and displays the configuration user interface (e.g., for selecting a number of cycles and progressing to a breathing phase). Referring back to FIG. 6A, user interface 602 depicts an exemplary watch face complication, affordance 604. In response to the selection of affordance 604, the device displays an exemplary configuration user interface, user interface screen 606.

FIG. 7 is a flow diagram illustrating a method for conducting a breathing sequence using an electronic device in accordance with some embodiments. Method 700 is performed at a device (e.g., 100, 300, 500) with a display. Some operations in method 700 are, optionally, combined, the order of some operations are, optionally, changed, and some operations are, optionally, omitted.

As described below, method 700 provides an intuitive way for conducting a breathing sequence. The method reduces the cognitive burden on a user for using an electronic device for breathing training, thereby creating a more efficient human-machine interface. For battery-operated computing devices, enabling a user to configure a breathing sequence faster and more efficiently conserves power and increases the time between battery charges.

At block 702, the device displays, on the display, a configuration user interface (e.g., user interface screen 606 of FIG. 6A), wherein the configuration user interface includes a prompt to select a number of cycles of a breathing sequence.

At block 704, the devices receives a first user input (e.g., selection of start affordance 612 of FIG. 6A). In accordance with some embodiments, the device includes a rotatable input mechanism (e.g., rotatable input mechanism 614), and wherein the first user input is a rotation of the rotatable input mechanism (block 706).

At block 708, in response to receiving the first user input, the device adjusts the number of cycles of the breathing sequence to the selected number of cycles. For example, in FIG. 6A, the device has adjusted the number of cycles (e.g., breaths), as represented by indicator 608, from 7 cycles to 21 cycles.

At block 710, the device initiates a breathing phase of the breathing sequence. For example, user interface screen 620 depicts the beginning of an exemplary breathing phase.

At block 712, during the breathing phase of the breathing sequence: the device displays, on the display, a first version of a progress indicator (block 714), and fluctuates the first version of the progress indicator in accordance with the selected number of cycles (block 716). For example, in user interface screen 620, the device displays a progress indicator 616 at the initiation of an exemplary breathing phase. In this example, the device fluctuates the progress indicator 616 (in accordance with a single exemplary cycle) as illustrated in user interface screens 620-628.

In accordance with some embodiments, at block 718, prior to initiating the breathing phase of the breathing sequence, the device: receives a second user input (block 720). In accordance with some embodiments, the first user input and the second user input are the same (block 722). In response to receiving the second user input, the device progresses to the breathing phase of the breathing sequence (block 724).

In accordance with some embodiments, at block 726, each cycle of the selected number of cycles includes a first period of time (e.g., period 664 of FIG. 6C) and a second period of time (e.g., period 666 of FIG. 6C) distinct from the first period, and wherein fluctuating the first version of the progress indicator includes: during each cycle of the selected number of cycles, the device: changes, at the start of the first period of time, a first variable visual characteristic of the progress indicator (block 728), and changes, at the start of the second period of time, the first variable visual characteristic of the progress indicator (block 730). For example, as shown in FIG. 6C, the progress indicator in user interfaces screens 620-628 changes in size (an exemplary first visual characteristic) throughout the cycle (e.g., as visually smooth animation). Thus, the size of the progress indicator changes at the start of period 664 (e.g. begins growing) and the start of period 666 (e.g., begins shrinking). In accordance with some embodiments, the second period of time is greater than the first period of time (block 732).

In accordance with some embodiments, the first variable visual characteristic is the size of the displayed progress indicator (block 734), and wherein changing, at the start of the first period of time, the first variable visual characteristic includes increasing the size of the displayed progress indicator (block 736), and wherein changing, at the start of the second period of time, the first variable visual characteristic includes decreasing the size of the displayed progress indicator (block 738).

In accordance with some embodiments, at block 740, fluctuating the first version of the progress indicator includes: the device displays, on the display, the first version of the progress indicator in a first state (block 742), the device animatedly transitions, during a first segment of time, the first version of the progress indicator from the first state to a second state (block 744), and the device animatedly transitions, during a second segment of time, the first version of the progress indicator from the second state to the first state (block 746). In accordance with some embodiments, the second segment of time is greater than the first segment of time (block 748). For example, screen 620 depicts a first state of a progress indicator, and screen 624 depicts a second state of a progress indicator. In this example, period 664 represents an exemplary first segment of time and period 666 represents an exemplary second segment of time. During the first period 664, the device animatedly transitions the progress indictor from the first state to the second state (e.g., intermediate screen 622 shows the progress indicator at a point during this transition). During the second period 666, the device animatedly transitions the progress indictor from the second state to the first state (e.g., intermediate screen 626 shows the progress indicator at a point during this transition).

In accordance with some embodiments, the first version of the progress indicator fluctuates at a first cyclic rate (block 750). In accordance with some embodiments, at block 752, the device receives a value of the first cyclic rate. At block 754, in response to receiving the value of the first cyclic rate, the device sets the first cyclic rate to the received value. In accordance with some embodiments the first cyclic rate is a predetermined number of cycles per unit of time (block 756). For example, the first cyclic rate is a number of cycles (e.g., breaths) per minute.

In accordance with some embodiments, at block 758, prior to displaying, on the display, the configuration user interface, the device determines whether a prompting criteria has been met (block 760). In accordance with a determination that the prompting criteria has been met, the device displays, on the display, a prompt that includes a first affordance (block 768). The device receives user input selection of the first affordance (block 770). In response to receiving the user input selection of the first affordance, the device displays, on the display, the configuration user interface (block 772).

In accordance with some embodiments, at block 762, determining whether a prompting criteria has been met includes determining whether a predetermined period of time has passed after a time associated with a previous breathing sequence. In accordance with some embodiments, the time associated with the previous breathing sequence is a beginning time associated with the previous breathing sequence (block 764). In accordance with some embodiments, the time associated with the previous breathing sequence is a completion time associated with the previous breathing sequence (block 766).

In accordance with some embodiments, at block 774, prior to initiating the breathing phase of the breathing sequence, the device initiates a preliminary phase of the breathing sequence (block 776). During the preliminary phase of the breathing sequence (block 778), the device displays, on the display, a second version of the progress indicator (block 780) and fluctuates the second version of the progress indicator in accordance with a preliminary number of cycles (block 782). In accordance with some embodiments, the preliminary number of cycles is independent of the selected number of cycles (block 784). The first version of the progress indicator fluctuates at a first cyclic rate, the second version of the progress indicator fluctuates at a second cyclic rate, and the second cyclic rate is greater than the first cyclic rate (block 786).

In accordance with some embodiments, at block 788, the first version of the progress indicator includes a second variable visual characteristic. At block 790, the device, further in response to receiving the first user input, selects an initial state of the second variable visual characteristic in accordance with the selected number of cycles.

At block 792, during the breathing phase of the breathing sequence, the device detects completion of a portion of the selected number of cycles (block 794), and, in response to detecting completion of the portion of the selected number of cycles, changes the second variable visual characteristic of the progress indicator (block 7100). In accordance with some embodiments, detecting completion of the portion of the selected number of cycles includes: determining whether the progress indicator has fluctuated in accordance with a predetermined number of cycles (block 796). In accordance with some embodiments, detecting completion of the portion of the selected number of cycles includes: detecting whether a predetermined amount of time has passed during the breathing phase of the breathing sequence (block 798). In accordance with some embodiments, the first version of the progress indicator includes a plurality of graphical elements, and changing the second variable visual characteristic of the progress indicator includes: changing a number of the displayed graphical elements of the plurality of graphical elements (block 7102).

In accordance with some embodiments, at block 7104, the device includes a haptic output device and, during the breathing phase of the breathing sequence, the device outputs one or more haptic breathing cues according to a haptic profile.

In accordance with some embodiments, at block 7112, outputting the one or more haptic breathing cues according to the haptic profile includes: outputting a first plurality of haptic breathing cues at a first frequency between cues during the first period of time (block 7114), and outputting a second plurality of haptic breathing cues at a second frequency between cues during the second period of time (block 7116). In accordance with some embodiments, the first frequency between cues is an increasing frequency, and wherein the second frequency between cues is a constant frequency (block 7118).

In accordance with some embodiments, at block 7106, outputting the one or more haptic breathing cues according to the haptic profile includes: outputting, at the start of the first period of time, a first number of haptic breathing cues (block 7108), and outputting, at the start of the second period of time, a second number of haptic breathing cues, wherein the first number and the second number are different (block 7110).

In accordance with some embodiments, at block 7120, the device includes a sensor. At block 7122, the device receives a first signal from the sensor during the breathing phase of the breathing sequence. At block 7124, the device determines an estimated heart rate based at least in part on the received first signal. At block 7126, the device displays, on the display, an indication of the estimated heart rate. In accordance with some embodiments, the indication of the estimated heart rate is displayed subsequent to completion of the breathing phase (block 7128). For example, an exemplary indication 636 of an estimated heart rate is displayed on the completion interface illustrated in user interface 632 in FIG. 6B.

In accordance with some embodiments, at block 7130, the device suppresses, during the breathing phase of the breathing sequence, the output of at least a subset of alerts that the device is configured to output.

In accordance with some embodiments, at block 7132, during the breathing phase of the breathing sequence, the device receives a third user input. At block 7134, the device determines whether the third user input meets a breathing sequence interrupt criteria. At block 7136, in accordance with a determination that the third user input meets the breathing sequence interrupt criteria, the device ends the breathing phase of the breathing sequence. At block 7138, subsequent to ending the breathing phase of the breathing sequence, the device: displays, on the display, an indication of a completed number of cycles, wherein the completed number of cycles includes the number of cycles, of the selected number of cycles, that the progress indicator fluctuated in accordance with after the breathing phase was initiated and before the third user input was received (block 7140). For example, the device displays interrupted session user interface 684, which includes an indication of the completed number of cycles (e.g., in the form of a total breathing time completed today ("SO FAR TODAY 5 MIN"), which includes the number of cycles of the interrupted session).

In accordance with some embodiments, at block 7142, subsequent to ending the breathing phase of the breathing sequence, the device: displays, on the display, a second affordance. For example, breathe again affordance 686 is an exemplary second affordance. At block 7144, the device receives user input selection of the second affordance. At block 7146, in response to the user input selection of the second affordance, the device displays, on the display, the configuration user interface. For example, user interface 688 depicts an exemplary configuration user interface displayed after breathe again affordance 686 is selected.

In accordance with some embodiments, at block 7148, the device determines an aggregate amount of time representing a completed number of cycles of the breathing sequence over a goal period. In accordance with some embodiments, the first version of the progress indicator fluctuates at a first cyclic rate, and the aggregate amount of time is determined based at least in part on the first cyclic rate (block 7150). In accordance with some embodiments, the goal period is the current day (block 7152). At block 7154, in response to detecting completion of the breathing phase of the breathing sequence, the device displays, on the display, a completion interface comprising: an indication of the aggregate amount of time, and a third affordance. For example, the device displays exemplary completion interface shown in user interface screen 632, which includes an indication of the aggregate amount of time (e.g., in the form of a total breathing time completed today ("SO FAR TODAY 6 MIN") and a breathe again affordance 638. At block 7160, the device receives user input selection of the third affordance. For example, the device receives selection of breathe again affordance 638. At block 7162, in response to receiving the user input selection of the third affordance, the device progresses to the breathing phase of the breathing sequence. For example, the device initiates a preliminary phase (e.g., as illustrated in screens 668A-668E), a breathing phase (e.g., as illustrated in screens 620-628), or a preliminary phase followed by a breathing phase.

In accordance with some embodiments, at block 7156, detecting completion of the breathing phase includes detecting that a predetermined amount of time has elapsed.

In accordance with some embodiments, at block 7158, the completion interface further includes an indication of an estimated heart rate. For example, user interface screen includes indicator 636, indicating an estimated heart rate.

In accordance with some embodiments, at block 7164, the device determines an aggregate amount of time representing a completed number of cycles of the breathing sequence over a goal period for each of a plurality of goal periods. In accordance with some embodiments, the goal period is a day, and the plurality of goal periods is seven days (block 7166). At block 7168, the device displays, on the display, a summary interface comprising an indicator for each of the plurality of goal periods, wherein the indicator for each of the plurality of goal periods represents the determined aggregate amount of time for its respective goal period of the plurality of goal periods. For example, the device displays the exemplary summary interface shown in user interface 642, depicting a daily summary for the last week, of completed (e.g., aggregate) amount of breathing time for each day. In this example, the goal period is a day, and the plurality of goal periods is seven days.

In accordance with some embodiments, at block 7170, the device receives a second signal during the breathing sequence. At block 7174, the device determines an estimated breathing pattern based at least in part on the received second signal. At block 7176, the device synchronizes the initiation of the breathing phase of the breathing sequence and the display of the progress indicator during the breathing phase of the breathing sequence with the estimated breathing pattern. For example, the device may synchronize the beginning of a breathing phase (e.g., as depicted in screen 620) with the appropriate point (point 690A of estimated breathing pattern 690 in FIG. 6F) of the estimated breathing pattern. That is, the device starts the breathing phase (e.g., beginning with an inhale period) at an appropriate time based on the estimated pattern (e.g., when the estimated pattern signals that the user is about to begin inhaling).

In accordance with some embodiments, at block 7178, synchronizing the initiation of the breathing phase of the breathing sequence and the display of the progress indicator during the breathing phase of the breathing sequence with the estimated breathing pattern includes: determining a synchronization event that is a transition between an inhale period and an exhale period of the estimated breathing pattern (block 7180), and, in accordance with a determination that the synchronization event has occurred (block 7182): initiating the breathing phase of the breathing sequence (7184) and displaying, on the display, the first version of the progress indicator (block 7186). For example, points 690A and 690B show transition events between exemplary inhale and exhale periods of an estimated breathing pattern.

In accordance with some embodiments, at block 7172, the device includes a sensor, and wherein receiving the second signal includes receiving the second signal from the sensor during the breathing sequence.

In accordance with some embodiments, at block 7188, prior to displaying the configuration user interface: the device determines an aggregate amount of time representing a completed number of cycles of one or more breathing sequences over a goal period (block 7190), displays, on the display, a fourth affordance comprising an indication of the aggregate amount of time (block 7192), and receives user input selection of the fourth affordance, wherein the configuration user interface is displayed in response to receiving the user input selection of the fourth affordance (block 7194). For example, user interface screen 602 of FIG. 6A depicts an exemplary fourth affordance, affordance 604. When the device receives selection of affordance 604, the configuration user interface depicted in user interface screen 606 is displayed.

Note that details of the processes described above with respect to method 700 (e.g., FIG. 7) are also applicable in an analogous manner to the methods described below. For example, method 1000 optionally includes one or more of the characteristics of the various methods described above with reference to method 700. For example, the exemplary configuration user interface depicted in user interface screen 606 can be displayed in response to receiving selection of an affordance 906 at the display of user interface 904 shown in FIG. 9A, depicting an exemplary displayed prompt. As another example, user interface 632 can correspond to user interface 902, and user interface 618 can correspond to user interface 910. For brevity, these details are not repeated below.

Figure 8:
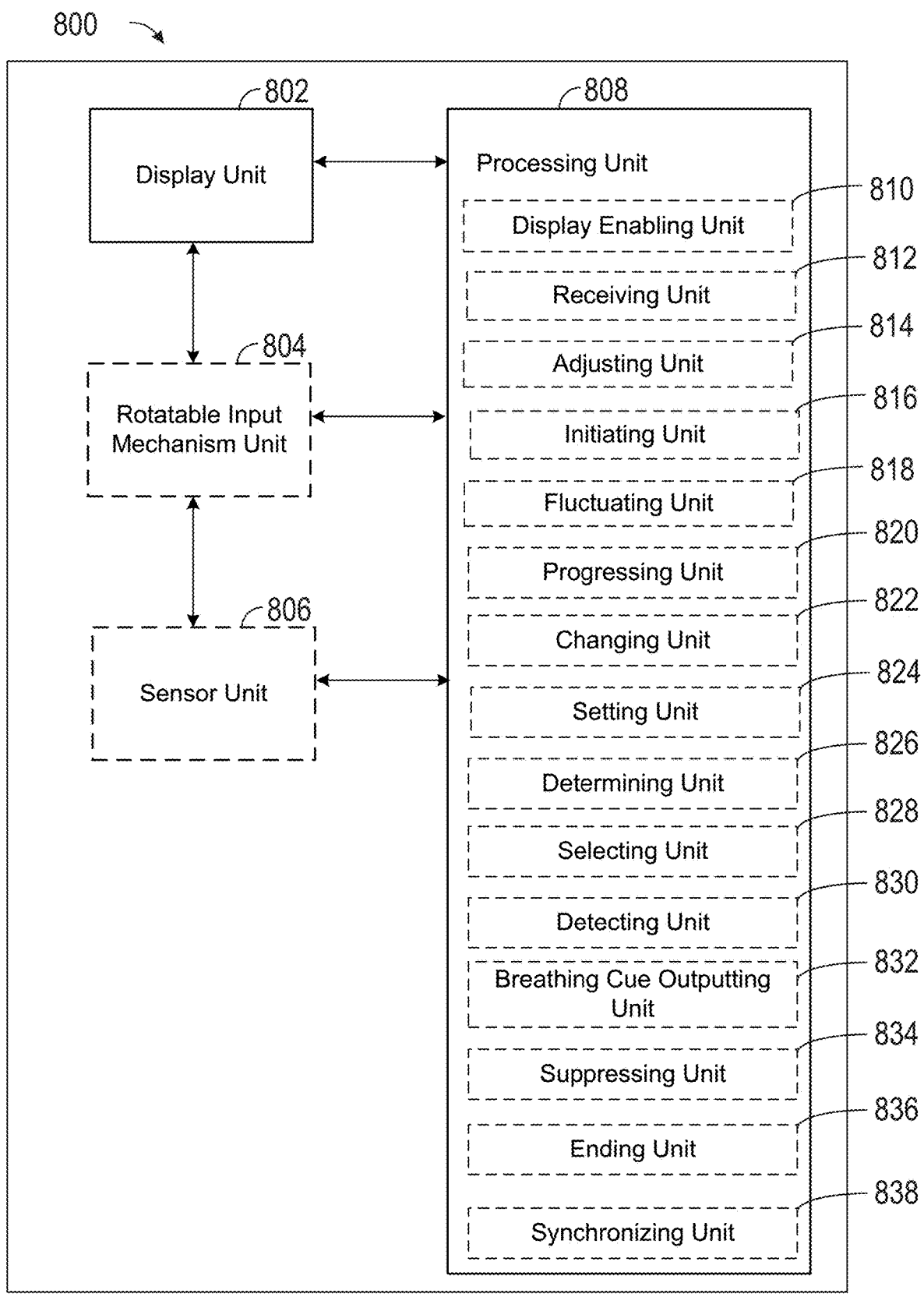
FIG. 8 illustrates a functional block diagram of an electronic device in accordance with some embodiments.

In accordance with some embodiments, FIG. 8 shows an exemplary functional block diagram of an electronic device 800 configured in accordance with the principles of the various described embodiments. In accordance with some embodiments, the functional blocks of electronic device 800 are configured to perform the techniques described above. The functional blocks of the device 800 are, optionally, implemented by hardware, software, or a combination of hardware and software to carry out the principles of the various described examples. It is understood by persons of skill in the art that the functional blocks described in FIG. 8 are, optionally, combined or separated into sub-blocks to implement the principles of the various described examples. Therefore, the description herein optionally supports any possible combination or separation or further definition of the functional blocks described herein.

As shown in FIG. 8, an electronic device 800 includes a display unit 802 configured to display a graphic user interface, and optionally, a rotatable input mechanism unit 804, and optionally, a sensor unit 806, and a processing unit 808 coupled to the display unit 802 and, optionally, the rotatable input mechanism unit 804 and the sensor unit 806. In some embodiments, the processing unit 808 includes a display enabling unit 810, a receiving unit 812, an adjusting unit 814, an initiating unit 816, and a fluctuating unit 818. In some embodiments, the processing unit 808 includes one or more of a progressing unit 820, a changing unit 822, a setting unit 824, a determining unit 826, a selecting unit 828, a detecting unit 830, a breathing cue outputting unit 832, a suppressing unit 834, an ending unit 836, and a synchronizing unit 838.

The processing unit 808 is configured to: enable display (e.g., with display enabling unit 810) of, on the display unit 802, a configuration user interface, wherein the configuration user interface includes a prompt to select a number of cycles of a breathing sequence; receive (e.g., with receiving unit 812) a first user input; in response to receiving the first user input, adjust (e.g., with adjusting unit 814) the number of cycles of the breathing sequence to the selected number of cycles; initiate (e.g., with initiating unit 816) a breathing phase of the breathing sequence; and during the breathing phase of the breathing sequence: enable display (e.g., with display enabling unit 810) of, on the display unit 802, a first version of a progress indicator; and fluctuate (e.g., with fluctuating unit 818) the first version of the progress indicator in accordance with the selected number of cycles.

In some embodiments, the device includes a rotatable input mechanism unit 804, coupled to the display unit 802 and the processing unit 808, and wherein the first user input is a rotation of the rotatable input mechanism unit 804.

In some embodiments, the processing unit 808 is further configured to: prior to initiating the breathing phase of the breathing sequence: receive (e.g., with receiving unit 812) a second user input; in response to receiving the second user input, progress (e.g., with progressing unit 820) to the breathing phase of the breathing sequence.

In some embodiments, wherein the first user input and the second user input are the same.

In some embodiments, the processing unit 808 is further configured to: wherein each cycle of the selected number of cycles includes a first period of time and a second period of time distinct from the first period, and wherein fluctuating the first version of the progress indicator includes: during each cycle of the selected number of cycles: change (e.g., with changing unit 822), at the start of the first period of time, a first variable visual characteristic of the progress indicator; and change (e.g., with changing unit 822), at the start of the second period of time, the first variable visual characteristic of the progress indicator.

In some embodiments, the first variable visual characteristic is the size of the displayed progress indicator, wherein changing, at the start of the first period of time, the first variable visual characteristic includes increasing the size of the displayed progress indicator, and wherein changing, at the start of the second period of time, the first variable visual characteristic includes decreasing the size of the displayed progress indicator.

In some embodiments, the second period of time is greater than the first period of time.

In some embodiments, fluctuating the first version of the progress indicator includes: enabling display (e.g., with display enabling unit 810) of, on the display unit 802, the first version of the progress indicator in a first state; animatedly transitioning (e.g., with display enabling unit 810), during a first segment of time, the first version of the progress indicator from the first state to a second state; and animatedly transitioning (e.g., with display enabling unit 810), during a second segment of time, the first version of the progress indicator from the second state to the first state.

In some embodiments, the second segment of time is greater than the first segment of time.

In some embodiments, the first version of the progress indicator fluctuates at a first cyclic rate.

In some embodiments, the processing unit 808 is further configured to: receive (e.g., with receiving unit 812) a value of the first cyclic rate; and in response to receiving the value of the first cyclic rate, set (e.g., with setting unit 824) the first cyclic rate to the received value.

In some embodiments, the first cyclic rate is a predetermined number of cycles per unit of time.

In some embodiments, the processing unit 808 is further configured to: prior to enabling display of, on the display unit 802, the configuration user interface: determine (e.g., with determining unit 826) whether a prompting criteria has been met; in accordance with a determination that the prompting criteria has been met, enable display (e.g., with display enabling unit 810) of, on the display unit 802, a prompt that includes a first affordance; receive (e.g., with receiving unit 812) user input selection of the first affordance; and in response to receiving the user input selection of the first affordance, enable display (e.g., with display enabling unit 810) of, on the display unit 802, the configuration user interface.

In some embodiments, determining whether a prompting criteria has been met includes determining whether a predetermined period of time has passed after a time associated with a previous breathing sequence.

In some embodiments, the time associated with the previous breathing sequence is a beginning time associated with the previous breathing sequence.

In some embodiments, the time associated with the previous breathing sequence is a completion time associated with the previous breathing sequence.

In some embodiments, the processing unit 808 is further configured to: prior to initiating the breathing phase of the breathing sequence: initiate (e.g., with initiating unit 816) a preliminary phase of the breathing sequence; and during the preliminary phase of the breathing sequence: enable display (e.g., with display enabling unit 810) of, on the display unit 802, a second version of the progress indicator; and fluctuate (e.g., with fluctuating unit 818) the second version of the progress indicator in accordance with a preliminary number of cycles.

In some embodiments, the preliminary number of cycles is independent of the selected number of cycles.

In some embodiments, the first version of the progress indicator fluctuates at a first cyclic rate, wherein the second version of the progress indicator fluctuates at a second cyclic rate, and wherein the second cyclic rate is greater than the first cyclic rate.

In some embodiments, the first version of the progress indicator includes a second variable visual characteristic, the processing unit 808 is further configured to: further in response to receiving the first user input, select (e.g., with selecting unit 828) an initial state of the second variable visual characteristic in accordance with the selected number of cycles.

In some embodiments, the processing unit 808 is further configured to: during the breathing phase of the breathing sequence: detect (e.g., with detecting unit 830) completion of a portion of the selected number of cycles; and in response to detecting completion of the portion of the selected number of cycles, change (e.g., with changing unit 822) the second variable visual characteristic of the progress indicator.

In some embodiments, detecting completion of the portion of the selected number of cycles includes: determining whether the progress indicator has fluctuated in accordance with a predetermined number of cycles.

In some embodiments, detecting completion of the portion of the selected number of cycles includes: detecting whether a predetermined amount of time has passed during the breathing phase of the breathing sequence.

In some embodiments, the first version of the progress indicator includes a plurality of graphical elements, and wherein changing the second variable visual characteristic of the progress indicator includes: changing a number of the displayed graphical elements of the plurality of graphical elements.

In some embodiments, the device includes a haptic output device, the processing unit 808 is further configured to: during the breathing phase of the breathing sequence, output (e.g., with breathing cue outputting unit 832) one or more haptic breathing cues according to a haptic profile.

In some embodiments, outputting the one or more haptic breathing cues according to the haptic profile includes: outputting a first plurality of haptic breathing cues at a first frequency between cues during the first period of time; and outputting a second plurality of haptic breathing cues at a second frequency between cues during the second period of time.

In some embodiments, the first frequency between cues is an increasing frequency, and wherein the second frequency between cues is a constant frequency.

In some embodiments, outputting the one or more haptic breathing cues according to the haptic profile includes: outputting, at the start of the first period of time, a first number of haptic breathing cues; and outputting, at the start of the second period of time, a second number of haptic breathing cues, wherein the first number and the second number are different.

In some embodiments, the device includes a sensor unit 806, coupled to the display unit 802 and the processing unit 808, the processing unit 808 is further configured to: receive (e.g., with receiving unit 812) a first signal from the sensor unit 806 during the breathing phase of the breathing sequence; determine (e.g., with determining unit 826) an estimated heart rate based at least in part on the received first signal; and enable display (e.g., with display enabling unit 810) of, on the display unit 802, an indication of the estimated heart rate. For example, user interface screen 632 of FIG. 6B depicts heart rate indicator 636, which is an exemplary indication of an estimated heart rate. As discussed in the example above, user interface screen 632, is an exemplary completion interface that is displayed after completion of a breathing phase of a breathing sequence. Accordingly, heart rate indicator 636 can represent an estimated heart rate that was determined using a signal from a sensor received during the breathing phase.

In some embodiments, the indication of the estimated heart rate is displayed subsequent to completion of the breathing phase.

In some embodiments, the processing unit 808 is further configured to: suppress (e.g., with suppressing unit 834), during the breathing phase of the breathing sequence, the output of at least a subset of alerts that the device is configured to output.

In some embodiments, the processing unit 808 is further configured to: during the breathing phase of the breathing sequence, receive (e.g., with receiving unit 812) a third user input; determine (e.g., with determining unit 826) whether the third user input meets a breathing sequence interrupt criteria; in accordance with a determination that the third user input meets the breathing sequence interrupt criteria, end (e.g., with ending unit 836) the breathing phase of the breathing sequence; and subsequent to ending the breathing phase of the breathing sequence: enable display (e.g., with display enabling unit 810) of, on the display unit 802, an indication of a completed number of cycles, wherein the completed number of cycles includes the number of cycles, of the selected number of cycles, that the progress indicator fluctuated in accordance with after the breathing phase was initiated and before the third user input was received.

In some embodiments, the processing unit 808 is further configured to: subsequent to ending the breathing phase of the breathing sequence: enable display (e.g., with display enabling unit 810) of, on the display unit 802, a second affordance; receive (e.g., with receiving unit 812) user input selection of the second affordance; and in response to the user input selection of the second affordance, enable display (e.g., with display enabling unit 810) of, on the display unit 802, the configuration user interface.

In some embodiments, the processing unit 808 is further configured to: determine (e.g., with determining unit 826) an aggregate amount of time representing a completed number of cycles of the breathing sequence over a goal period; in response to detecting completion of the breathing phase of the breathing sequence, enable display (e.g., with display enabling unit 810) of, on the display unit 802, a completion interface comprising: an indication of the aggregate amount of time; and a third affordance; receive (e.g., with receiving unit 812) user input selection of the third affordance; and in response to receiving the user input selection of the third affordance, initiate (e.g., with initiating unit 816) the breathing phase of the breathing sequence.

In some embodiments, detecting completion of the breathing phase includes detecting that a predetermined amount of time has elapsed.

In some embodiments, the completion interface further includes an indication of an estimated heart rate.

In some embodiments, the goal period is the current day.

In some embodiments, the first version of the progress indicator fluctuates at a first cyclic rate, and wherein the aggregate amount of time is determined based at least in part on the first cyclic rate.

In some embodiments, the processing unit 808 is further configured to: determine (e.g., with determining unit 826) an aggregate amount of time representing a completed number of cycles of the breathing sequence over a goal period for each of a plurality of goal periods; enable display (e.g., with display enabling unit 810) of, on the display unit 802, a summary interface comprising an indicator for each of the plurality of goal periods, wherein the indicator for each of the plurality of goal periods represents the determined aggregate amount of time for its respective goal period of the plurality of goal periods.

In some embodiments, the goal period is a day, and wherein the plurality of goal periods is seven days.

In some embodiments, the processing unit 808 is further configured to: receive (e.g., with receiving unit 812) a second signal during the breathing sequence; determine (e.g., with determining unit 826) an estimated breathing pattern based at least in part on the received second signal; and synchronize (e.g., with synchronizing unit 838) the initiation of the breathing phase of the breathing sequence and the display of the progress indicator during the breathing phase of the breathing sequence with the estimated breathing pattern.

In some embodiments, synchronizing the initiation of the breathing phase of the breathing sequence and the display of the progress indicator during the breathing phase of the breathing sequence with the estimated breathing pattern includes: determining a synchronization event that is a transition between an inhale period and an exhale period of the estimated breathing pattern; and in accordance with a determination that the synchronization event has occurred: initiating the breathing phase of the breathing sequence; and enabling display of, on the display unit 802, the first version of the progress indicator.

In some embodiments, the device includes a sensor unit 806, coupled to the display unit 802 and the processing unit 808, and wherein receiving the second signal includes: receiving the second signal from the sensor unit 806 during the breathing sequence.

In some embodiments, the processing unit 808 is further configured to: prior to enabling display of the configuration user interface: determine (e.g., with determining unit 826) an aggregate amount of time representing a completed number of cycles of one or more breathing sequences over a goal period; enable display (e.g., with display enabling unit 810) of, on the display unit 802, a fourth affordance comprising an indication of the aggregate amount of time; and receive (e.g., with receiving unit 812) user input selection of the fourth affordance, wherein the configuration user interface is displayed in response to receiving the user input selection of the fourth affordance.

The operations described above with reference to FIG. 7A-7L are, optionally, implemented by components depicted in FIGS. 1A-1B or FIG. 8. For example, displaying operation 702, receiving operation 704, and adjusting operation 708 are, optionally, implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 optionally utilizes or calls data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

FIG. 9A illustrates exemplary user interfaces for prompting a user to conduct breathing sequences, in accordance with some embodiments. The user interfaces in these figures are used to illustrate the processes described below, including the processes in FIG. 10. FIG. 9B illustrates an exemplary list of times for displaying reminders, in accordance with some embodiments.

In accordance with some embodiments, an electronic device detects a time associated with a first breathing sequence. For example, the time associated with the first breathing sequence is a beginning or an ending time of the first breathing sequence. In some examples, the detected time can be associated with a first detected activity performed by the user in the current day. For example, the first time can be the time that user activity was first performed today. That is, when the user wakes up for the day, they will not have conducted a previous breathing sequence that day. Accordingly, they can be prompted based on the user's activity (e.g., when they first wake up, or otherwise start physical activity). The first detected activity can be detected, for example, by detecting physical activity or determined based on user interaction with the device (or a second device paired, connected, or otherwise in communication with the device).

User interface screen 902 of FIG. 9A depicts a completion interface displayed after completion of the breathing phase of an example first breathing sequence. In this example, the breathing phase of the first breathing sequence (e.g., a previous breathing sequence) ended at 8:00 AM, as depicted by time indicator 903 on the completion interface 902. In this example, the time associated with the first breathing sequence is an ending time (e.g., the ending of the breathing phase) associated with the first breathing sequence. In some examples, the time is a beginning time (e.g., the beginning of the breathing phase), which in this example would be 7:57 AM if the breathing phase lasted for 3 minutes.

In accordance with some embodiments, the device generates a prompting criteria based on a predetermined prompting frequency and the detected time associated with the first breathing sequence. For example, the prompting criteria can be: the occurrence of a particular time, or the expiration of a timer. The predetermined prompting frequency can be a frequency with which the device outputs (e.g., displays) a prompt. In this example, the predetermined prompting frequency is every 2 hours, or simply, 2 hours. A prompt can be a visual, textual, audible, and/or haptic output which, for example, reminds or encourages a user to conduct a breathing sequence. For example, a prompt can include textual information encouraging a user to conduct a breathing sequence (e.g., "Take time to breathe", as shown in user interface 904). A prompt may take the form of a notification on the display of the device (e.g., as shown in user interface 904).

The device determines if the prompting criteria has been met. In accordance with a determination that the prompting criteria has been met, the device displays, on the display, a prompt to initiate a second breathing sequence. For example, an exemplary prompt is shown at user interface screen 904 of FIG. 9A. In this example, the prompting frequency is every two hours and the time associated with the first (e.g., previous) breathing sequence is the end of the breathing phase, as discussed above. Thus, the device displays user interface screen 904 two hours after the completion of the breathing phase of the first breathing sequence. In this example, because the prompting frequency is every two hours, the prompting criteria can be the occurrence of 10:00 AM (e.g., two hours after 8:00 AM) or the expiration of a two hour timer (e.g., started at 8:00 AM). In either case, user interface screen 904 is displayed at 10:00 AM, as shown by time indicator 905, and thus the prompt is displayed in response to the prompting criteria being met.

In some examples, the prompt includes a first affordance. For example, user interface screen 904 includes start affordance 906. The device receives user input selection of the first affordance and, in response, displays, on the display, a second breathing sequence user interface. For example, if the device receives user input selection of start affordance 906, it can display exemplary configuration user interface screen 910. At user interface screen 910, the user may set the number of cycles, and cause the device to progress to a breathing phase of a breathing sequence (e.g., by pressing start affordance 911) as described above with respect to FIG. 6A. For example, after receiving selection of start affordance 911 at user interface screen 910, user interface screen 912 is displayed (which corresponds to user interface screen 620 of FIG. 6A), which depicts an exemplary a progress indicator at the beginning of a breathing phase, during which it will fluctuate in accordance with a selected number of cycles.

In accordance with some embodiments, the predetermined prompting frequency is a predetermined length of time. For example, the predetermine prompting frequency may be two hours (e.g., representing a prompt every two hours).

In accordance with some embodiments, to generate the prompting criteria, the device determines a prompting time that occurs the predetermined length of time after the time associated with the first breathing sequence. In some embodiments, the prompting time is a particular time after the time associated with the first breathing sequence. For example, if the predetermined length of time is two hours and the time associated with the first breathing sequence is 10:00 AM, the prompting time is 12:00 PM, two hours after the time associated with the first breathing sequence. To determine if the prompting criteria has been met, the device determines if the prompting time has occurred. For example, the device determines that the prompting time has occurred when the current time is 12:00 PM.

In accordance with some embodiments, to generate the prompting criteria, the device sets a timer in accordance with the predetermined length of time. For example, if the predetermined length of time is two hours, the device sets a two hour timer. The device starts the timer. To determine if the prompting time has occurred, the device determines whether the timer has expired. For example, the timer expires if it counts down to a value of zero from a set value, or up to the set value from zero.

In accordance with some embodiments, to detect the time associated with the first breathing sequence, the device detects a time that occurred during the first breathing sequence. In some embodiments, the time associated with the first breathing sequence (e.g., a previous breathing sequence) can be any time during which an application used to conduct the breathing sequence was open. In some embodiments, the time associated with the previous breathing sequence is any time during which any user interface of the previous breathing sequence was displayed.

In some embodiments, the time associated with a previous breathing sequence is an initiation time associated with the previous breathing sequence, for example, that is determined based on the time of: display of a configuration user interface of the previous breathing sequence, or initiation of a breathing or preliminary phase of the previous breathing sequence.

In some embodiments, the time associated with a previous breathing sequence is a completion time associated with the previous breathing sequence, for example, that is determined based on the time of: ending of a breathing phase of the previous breathing sequence, display of a completion summary of the previous breathing sequence, or the exiting of a breathing application used to conduct the previous breathing sequence.

In accordance with some embodiments, to detect the time associated with the first breathing sequence, the device detects an initiation time of a breathing phase of the first breathing sequence. For example, the detected time associated with the first breathing sequence is the time at which a breathing phase of the first (e.g., previous) breathing sequence was initiated, representing the beginning of a user participating in a breathing exercise.

In accordance with some embodiments, to detect the time associated with the first breathing sequence, the device detects a completion time of a breathing phase of the first breathing sequence. For example, the detected time associated with the first breathing sequence is the time at which a breathing phase of the first (e.g., previous) breathing sequence ended, which represents the completion of a user participating in a breathing exercise.

In some examples, the user may conduct a breathing sequence before the prompt is scheduled to be displayed. In accordance with some embodiments, prior to a determination that the prompting criteria has been met, the device detects a time associated with a third breathing sequence. For example, before the user is prompted at the regularly-scheduled prompting time, the device detects that the user has conducted an intervening breathing sequence without being prompted. In accordance with a detection of the time associated with the third breathing sequence, the device updates the prompting criteria based on the predetermined prompting frequency and the detected time associated with the third breathing sequence. For example, if the prompting frequency is every two hours, the device can set the new prompting criteria such that it will be satisfied two hours after the time associated with the third breathing sequence (e.g., a time during the third breathing sequence). For example, the time associated with the third breathing sequence is 9:20 AM. This time occurs between the previous breathing sequence (e.g., 8:00 AM as shown in screen 902) and a previously-scheduled prompting time (e.g., 10:00 AM as shown in screen 904). Thus, in this example, the new prompting criteria is set to be the occurrence of the time 11:20 AM (or the expiration of a timer at that time), which is two hours after the time associated with the intervening (third) breathing sequence. Accordingly, if a user decides to conduct a breathing exercise early (e.g., without being prompted), a scheduled prompt can automatically be adjusted in order to maintain the prompting frequency (e.g., every two hours) instead of again prompting the user at 10:00 AM, only forty minutes after conducting an intervening breathing sequence (e.g., the third breathing sequence).

In accordance with some embodiments, the device receives a first user input. For example, at user interface screen 910, the device receives user input corresponding to a selection of start affordance 911. In response to receiving the first user input, the device progresses to a breathing phase of the second breathing sequence. During the breathing phase of the second breathing sequence, the device displays, on the display, a first version of a progress indicator and fluctuates the first version of the progress indicator in accordance with a selected number of cycles. For example, the device progresses to the breathing phase and displays fluctuation of a progress indicator, as illustrated in screen 912, which corresponds to screen 920 of FIG. 6A. The device optionally fluctuates a first version of a progress indicator in accordance with the operations described above, for example, with respect to user interface screens 920-928 of FIG. 6A.

In accordance with some embodiments, prior to initiating the breathing phase of the second breathing sequence, the device receives a second user input. In response to receiving the second user input, the device adjusts a number of cycles of the second breathing sequence to the selected number of cycles. For example, the device receives a rotation of a rotatable input mechanism, as described above with respect to user interface 606 of FIG. 6A, and, in response, adjusts the number of cycles as shown in user interface screen 618, which corresponds to user interface screen 910 of FIG. 9A.

In accordance with some embodiments, the prompt to initiate the second breathing sequence includes a second affordance. In some examples, the second affordance is a "snooze" or "dismiss" affordance, or the like. For example, user interface screen 904 includes snooze affordance 908. The device receives user input selection of the second affordance and, in response, ceases display, on the display, of the prompt and updates the prompting criteria. For example, in response to receiving user selection of snooze affordance 906, the device ceases display of user interface 904 representing a prompt, and displays the exemplary home screen depicted in user interface screen 916. Also in response to the user selection in this example, the device updates the prompting criteria, which is explained in more detail below.

In accordance with some embodiments, to update the prompting criteria, the device updates the prompting criteria based on the predetermined prompting frequency and the detected time associated with the first breathing sequence. For example, the prompting criteria can be the occurrence of a particular time, or the expiration of a timer, and updating can include determining a new time, or setting a new timer (or resetting an existing timer).

In some embodiments, the updated prompting criteria can be based on the first breathing sequence. For example, if the device receives user input selection of the second affordance (e.g., snooze affordance 908), the device can update the prompting criteria to be the occurrence of a time that will occur after a length of time equal to an integer multiple of the predetermined length of time (the predetermined prompting frequency) since the time associated with the first breathing sequence. For instance, if the predetermined prompting frequency is every two hours, the prompting criteria can be the occurrence of a prompting time four hours after the time associated with the first breathing sequence—that is, the prompting time occurs two integer multiples of the predetermined prompting frequency after the time associated with the first breathing sequence. In some examples, the multiple is not an integer.

In accordance with some embodiments, to update the prompting criteria, the device detects a time associated with the received user input selection of the second affordance and updates the prompting criteria based on the predetermined prompting frequency and the detected time associated with the received user input selection of the second affordance. In some examples, the updated prompting criteria is based on a time associated with the received user input selection of the second affordance. For example, if the device receives selection of snooze affordance 908 at 10:00 AM, the device can set the prompting criteria to be the expiration of a timer equal to the length of the predetermined prompting frequency, wherein the device starts the timer at the time associated with the received user input selection snooze affordance 908 (10:00 AM), or soon thereafter. If the predetermined prompting frequency is every two hours, for example, the prompting criteria is the expiration of a timer that is two hours long and that starts after the time associated with the received user input selection of the second affordance. In this example, the updated prompting criteria would be satisfied at 12:00 PM, or two hours after the snooze affordance 904 was selected. In some examples, after receiving selection of the snooze affordance 904, the device ceases display of the prompt and displays exemplary home screen 916. When the updated prompting criteria is met at 12:00 PM, the device displays user interface screen 920. User interface screen 920 is similar to user interface screen 904, but is displayed at the 12:00 PM, as shown by time indicator 922.

In some examples, the prompt can optionally be dismissed for a period of time less than the predetermined prompting frequency. In accordance with some embodiments, to update the prompting criteria, the device updates the prompting criteria based on a snooze interval, wherein the predetermined prompting frequency is a predetermined length of time, and wherein the snooze interval is a length of time that is distinct from the predetermined prompting frequency. For example, if the predetermined prompting frequency is every two hours, the snooze interval can be fifteen minutes (a quarter of an hour). This alternative way to dismiss a prompt can be desirable if a user is presently unable to conduct a breathing sequence, but would like to be reminded earlier than the normal prompting frequency. In some examples, after receiving selection of the snooze affordance 904, the device ceases display of the prompt and displays exemplary home screen 916. When the updated prompting criteria is met (e.g., after the snooze interval, at 10:15 AM), the device displays user interface screen 924. User interface screen 924 is similar to user interface screen 904, but is displayed at the 10:15 AM, as shown by time indicator 926.

In accordance with some embodiments, further in response to receiving the user input selection of the second affordance, the device forgoes display of all prompts to initiate a breathing sequence during the remainder of a current day. For example, in response to receiving user selection of snooze affordance 908 at user interface 904, the device can dismiss the current prompt and prevent the display of further prompts for the rest of the current day. In this example, the next prompt (e.g., breathe reminder) would be displayed on the next day. For example, user interface screens 920 and/or 924 would not be displayed.

In accordance with some embodiments, the device determines if the updated prompting criteria has been met. In accordance with a determination that the updated prompting criteria has been met, the device displays, on the display, a prompt to initiate a fourth breathing sequence, wherein the prompt includes a third affordance. For example, after the user has snoozed/dismissed a breathe reminder (as described above), the device displays another prompt (e.g., user interface screens 920 or 924) that contains a third affordance (e.g., start affordance 921 or 925). The device receives user input selection of the third affordance and, in response, displays, on the display, a fourth breathing sequence user interface. In some examples, the fourth breathing sequence user interface is a configuration user interface. For example, the device displays a configuration user interface for selecting a number of cycles for the breathing sequence, as shown in user interface screen 910 (which corresponds to user interface screen 606 and 618 in FIG. 6A). In some examples, in response to selection of the third affordance, the device displays any other user interface screen as described herein with respect to a breathing sequence. For example, the device may automatically initiate a breathing sequence and display the user interface screens 620-628 of FIG. 6A, depicting the fluctuation of a progress indicator during a breathing phase.

In some examples, the device displays a prompt in response to any suitable input, information, or event. For example, the device optionally accesses calendar information associated with the user of the device in order to determine an appropriate time (e.g., a "free time") that may be good for breathing (e.g., a block of time with no scheduled events). The calendar information can optionally indicate a scheduled event related to breathing (event entitled "Time to Breathe")—in this case, the graphical user interface 904 may be presented in accordance with the time and date of the scheduled event. The device optionally accesses the calendar information to determine details about upcoming events in order to determine whether a breathing sequence could be helpful before the events. For example, user interface screen 904 is optionally presented a few minutes before meetings in order to help the user calm and prepare for the upcoming meetings. The determination of which meetings and when to present user interface screen 904 are optionally based on predefined configuration information (e.g., if the user has indicated that they want to breathe before all meetings, that they want to breathe before all meetings with more than five participants, that they want to breathe before all meetings with a particular person, and/or based at least in part on information learned from behaviors (e.g., the user regularly, occasionally, or always goes through a breathing sequence before certain meetings or at certain times).

The device optionally receives sensor data from one or more sensor, which may be used to infer an appropriate time to present user interface screen 904. For example, the sensor data can include motion information that indicates whether the device (and a user) is moving. If the device is moving at a pace similar to walking, then perhaps the user would not be interested in conducting in a breathing sequence, and thus user interface screen 904 is not displayed. However, if the device is moving at a quicker pace, then perhaps the user is driving and may be interested in conducting in a breathing sequence. The sensor data may also include user health data that indicates one or more health metrics of the user. For example, if the user health data indicates an elevated heart rate, user interface screen 904 is optionally presented. Participating in the breathing sequence may assist the user in reducing her heart rate. The user health data may also be used to infer aspects of user breath events, and user interface screen 904 is optionally presented in response to detection of a sequence of particular breath events. For example, if the user takes three deep breaths, the device may determine and/or infer that the user desires to conduct in a breathing sequence, and thus optionally presents user interface screen 904.

FIG. 9B illustrates table 930 including exemplary times for displaying prompts, in accordance with some embodiments. FIG. 9B is included to illustrate an example of the results of generating prompting criteria in accordance with different prompting frequencies.

Column 930A depicts an initiation time associated with the first breathing sequence. In this example, the initiation time is the time that the breathing phase of the first breathing sequence was initiated. For ease of comparison, the initiation time is the same for each example (e.g., row).

Column 930B depicts a completion time associated with the first breathing sequence. In this example, the initiation time is the time that the breathing phase of the first breathing sequence ended. For ease of comparison, the completion time is the same for each example (e.g., row).

Column 930C depicts a prompting frequency associated with each example (e.g., row). The prompting frequencies range from a value of 2 (e.g., prompting once every 2 hours) to a value of 12 (e.g., prompting once every 12 hours).

Column 930D depicts the ranges of time that the device can display a prompt, in accordance with some embodiments. For example, in the example with a prompting frequency of 2, the device can optionally prompt at any time between 9:57 AM to 10:00 AM, which represents a range of time during the first breathing sequence (and in particular, the breathing phase). The particular time within this range at which the device displays a prompt depends on the time associated with the first breathing sequence on which the device is configured to base its determination. For example, if the device is configured to prompt 2 hours from the initiation time of the previous breathing phase, the prompt is displayed at 9:57 AM. If the device is configured to prompt 2 hours from the completion time of the previous breathing phase, the prompt is displayed at 10:00 AM.

FIG. 10 is a flow diagram illustrating a method for prompting a user to conduct a breathing sequence using an electronic device in accordance with some embodiments. Method 1000 is performed at a device (e.g., 100, 300, 500) with a display. Some operations in method 1000 are, optionally, combined, the order of some operations are, optionally, changed, and some operations are, optionally, omitted.

As described below, method 1000 provides an intuitive way for prompting a user to conduct a breathing sequence. The method reduces the cognitive burden on a user for setting up breathing reminder prompts and interacting with a prompt—for example, to dismiss it or to access an application for conducting a breathing sequence—thereby creating a more efficient human-machine interface. For battery-operated computing devices, enabling a user to configure and dispose of prompts faster and more efficiently conserves power and increases the time between battery charges.

At block 1002, the device detects a time associated with a first breathing sequence. For example, the device detects that a first (e.g., previous) breathing sequence was completed at 8:00 AM, as shown in user interface screen 902 of FIG. 9A.

At block 1010, the device generates a prompting criteria based on a predetermined prompting frequency and the detected time associated with the first breathing sequence. For example, if the predetermined prompting frequency is every 2 hours, and the detected time is 8:00 AM, the device generates a prompting criteria based on these values. For example, the prompting criteria may be the occurrence of 10:00 AM, or the expiration of a 2 hour timer started at 8:00 AM (and thus, expiring at 10:00 AM).

At block 1014, the device determines if the prompting criteria has been met. For example, the device determines if a timer has expired, or whether the current time is 10:00 AM.

At block 1028, in accordance with a determination that the prompting criteria has been met, the device displays, on the display, a prompt to initiate a second breathing sequence, wherein the prompt includes a first affordance. For example, the device can display user interface screen 904 which includes start affordance 906.

At block 1030, the device receives user input selection of the first affordance.

At block 1032, in response to receiving the user input selection of the first affordance, the device displays, on the display, a second breathing sequence user interface. For example, in response to receiving user input selection of start affordance 906, the device displays user interface 910, depicting an exemplary configuration user interface.

In accordance with some embodiments, at block 1012, the predetermined prompting frequency is a predetermined length of time. For example, the predetermined prompting frequency is 2 hours, 4, hours, 8, hours, or the like.

In accordance with some embodiments, at block 1016, generating the prompting criteria includes: determining a prompting time that occurs the predetermined length of time after the time associated with the first breathing sequence. At block 1018, determining if the prompting criteria has been met includes: determining if the prompting time has occurred.

In accordance with some embodiments, at block 1020, generating the prompting criteria further includes: setting a timer in accordance with the predetermined length of time (block 1022), and starting the timer (block 1024), wherein determining if the prompting time has occurred includes: determining whether the timer has expired (block 1026).

In accordance with some embodiments, at block 1004, detecting the time associated with the first breathing sequence includes: detecting a time that occurred during the first breathing sequence.

In accordance with some embodiments, at block 1006, detecting the time associated with the first breathing sequence includes: detecting an initiation time of a breathing phase of the first breathing sequence.

In accordance with some embodiments, at block 1008, detecting the time associated with the first breathing sequence includes: detecting a completion time of a breathing phase of the first breathing sequence.

In accordance with some embodiments, at block 1034, prior to a determination that the prompting criteria has been met, the device: detects a time associated with a third breathing sequence (block 1036), and, in accordance with a detection of the time associated with the third breathing sequence, updates the prompting criteria based on the predetermined prompting frequency and the detected time associated with the third breathing sequence (block 1038).

In accordance with some embodiments, at block 1040, the device receives a first user input. At block 1042, in response to receiving the first user input, the device progresses to a breathing phase of the second breathing sequence. At block 1050, during the breathing phase of the second breathing sequence, the device: displays, on the display, a first version of a progress indicator (block 1052), and fluctuates the first version of the progress indicator in accordance with a selected number of cycles (block 1054).

In accordance with some embodiments, at block 1044, prior to initiating the breathing phase of the second breathing sequence, the device: receives a second user input (block 1046), and, in response to receiving the second user input, adjusts a number of cycles of the second breathing sequence to the selected number of cycles (block 1048).

In accordance with some embodiments, at block 1056, the prompt to initiate the second breathing sequence includes a second affordance. At block 1058, the device receives user input selection of the second affordance. At block 1060, in response to receiving the user input selection of the second affordance, the device: ceases display, on the display, of the prompt (block 1062), and updates the prompting criteria (block 1064).

In accordance with some embodiments, at block 1066, updating the prompting criteria includes: updating the prompting criteria based on the predetermined prompting frequency and the detected time associated with the first breathing sequence.

In accordance with some embodiments, at block 1068, updating the prompting criteria includes: detecting a time associated with the received user input selection of the second affordance; and updating the prompting criteria based on the predetermined prompting frequency and the detected time associated with the received user input selection of the second affordance.

In accordance with some embodiments, at block 1070, updating the prompting criteria includes: updating the prompting criteria based on a snooze interval, wherein the predetermined prompting frequency is a predetermined length of time, and wherein the snooze interval is a length of time that is distinct from the predetermined prompting frequency.

In accordance with some embodiments, at block 1072, further in response to receiving the user input selection of the second affordance, the device forgoes display of all prompts to initiate a breathing sequence during the remainder of a current day.

In accordance with some embodiments, at block 1074, the device determines if the updated prompting criteria has been met. At block 1076, in accordance with a determination that the updated prompting criteria has been met, the device displays, on the display, a prompt to initiate a fourth breathing sequence, wherein the prompt includes a third affordance. At block 1078, the device receives user input selection of the third affordance. At block 1080, in response to receiving the user input selection of the third affordance, the device displays, on the display, a fourth breathing sequence user interface.

Note that details of the processes described above with respect to method 1000 (e.g., FIG. 10 are also applicable in an analogous manner to the methods described above. For example, method 700 optionally includes one or more of the characteristics of the various methods described above with reference to method 1000. For example, the exemplary configuration user interface depicted in user interface screen 606 can be displayed in response to receiving selection of an affordance 906 at the display of user interface 904, depicting an exemplary displayed prompt. As another example, user interface 632 can correspond to user interface 902, and user interface 618 can correspond to user interface 910. For brevity, these details are not repeated below.

Figure 11:
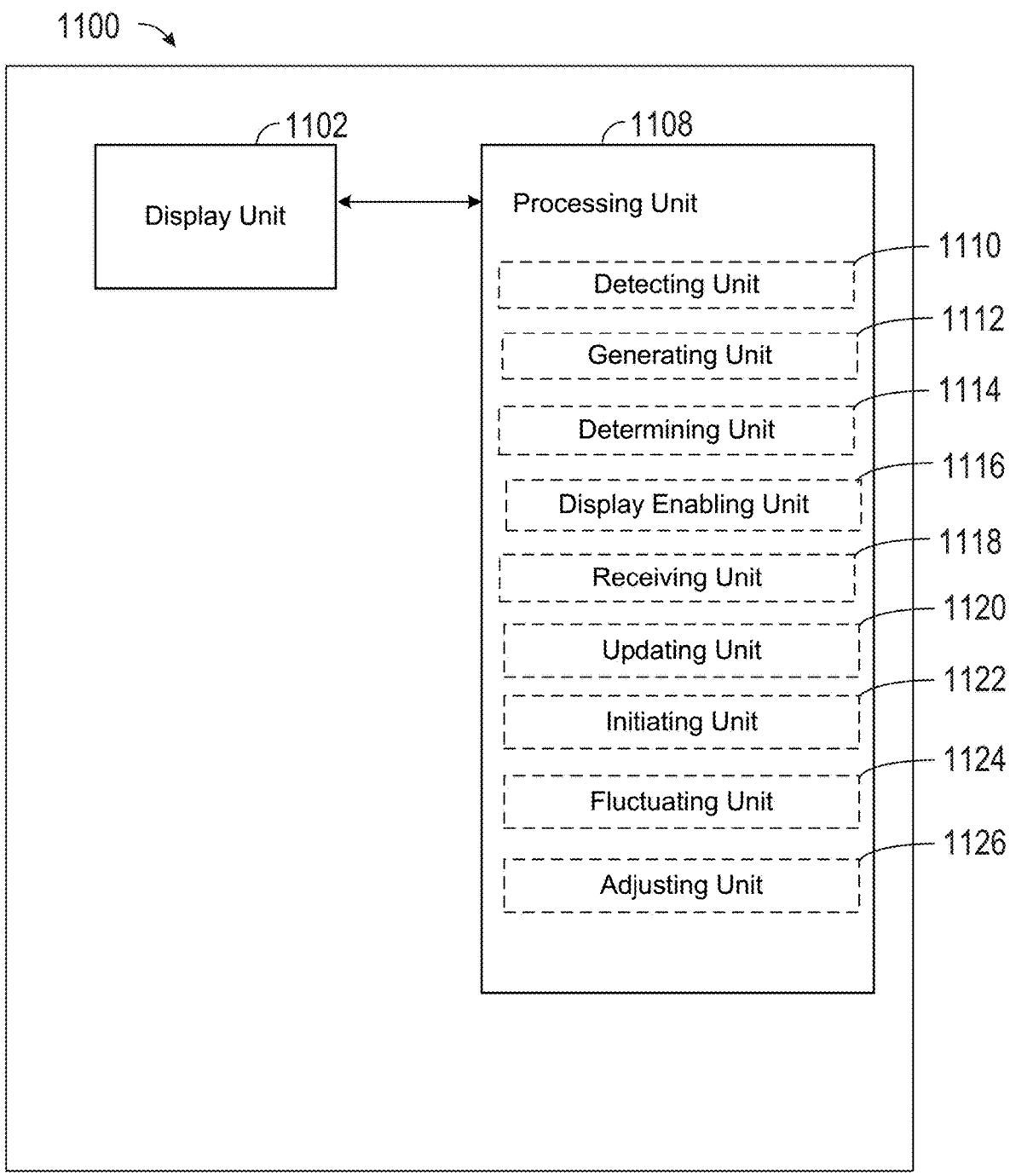
FIG. 11 illustrates a functional block diagram of an electronic device in accordance with some embodiments.

In accordance with some embodiments, FIG. 11 shows an exemplary functional block diagram of an electronic device 1100 configured in accordance with the principles of the various described embodiments. In accordance with some embodiments, the functional blocks of electronic device 1100 are configured to perform the techniques described above. The functional blocks of the device 1100 are, optionally, implemented by hardware, software, or a combination of hardware and software to carry out the principles of the various described examples. It is understood by persons of skill in the art that the functional blocks described in FIG. 11 are, optionally, combined or separated into sub-blocks to implement the principles of the various described examples. Therefore, the description herein optionally supports any possible combination or separation or further definition of the functional blocks described herein.

As shown in FIG. 11, an electronic device 1100 includes a display unit 1102 configured to display a graphic user interface, and a processing unit 1108 coupled to the display unit 1102. In some embodiments, the processing unit 1108 includes a detecting unit 1110, a generating unit 1112, a determining unit 1114, a display enabling unit 1116, and a receiving unit 1118. In some embodiments, processing unit 1108 also includes one or more of an updating unit 1120, an initiating unit 1122, a fluctuating unit 1124, and an adjusting unit 1126.

The processing unit 1108 is configured to: detect (e.g., with detecting unit 1110) a time associated with a first breathing sequence; generate (e.g., with generating unit 1112) a prompting criteria based on a predetermined prompting frequency and the detected time associated with the first breathing sequence; determine (e.g., with determining unit 1114) if the prompting criteria has been met; in accordance with a determination that the prompting criteria has been met, enable display (e.g., with display enabling unit 1116) of, on the display unit 1102, a prompt to initiate a second breathing sequence, wherein the prompt includes a first affordance; receive (e.g., with receiving unit 1118) user input selection of the first affordance; and in response to receiving the user input selection of the first affordance, enable display (e.g., with display enabling unit 1116) of, on the display unit 1102, a second breathing sequence user interface.

In some embodiments, the predetermined prompting frequency is a predetermined length of time.

In some embodiments, generating the prompting criteria includes: determining a prompting time that occurs the predetermined length of time after the time associated with the first breathing sequence; and wherein determining if the prompting criteria has been met includes: determining if the prompting time has occurred.

In some embodiments, generating the prompting criteria further includes: setting a timer in accordance with the predetermined length of time; and starting the timer; and wherein determining if the prompting time has occurred includes: determining whether the timer has expired.

In some embodiments, detecting the time associated with the first breathing sequence includes: detecting a time that occurred during the first breathing sequence.

In some embodiments, detecting the time associated with the first breathing sequence includes: detecting an initiation time of a breathing phase of the first breathing sequence.

In some embodiments, detecting the time associated with the first breathing sequence includes: detecting a completion time of a breathing phase of the first breathing sequence.

In some embodiments, the processing unit 1108 is further configured to: prior to a determination that the prompting criteria has been met: detect (e.g., with detecting unit 1110) a time associated with a third breathing sequence; and in accordance with a detection of the time associated with the third breathing sequence, update (e.g., with updating unit 1120) the prompting criteria based on the predetermined prompting frequency and the detected time associated with the third breathing sequence.

In some embodiments, the processing unit 1108 is further configured to: receive (e.g., with receiving unit 1118) a first user input; in response to receiving the first user input, initiate (e.g., with initiating unit 1122) a breathing phase of the second breathing sequence; and during the breathing phase of the second breathing sequence: enable display (e.g., with display enabling unit 1116) of, on the display unit 1102, a first version of a progress indicator; and fluctuate (e.g., with fluctuating unit 1124) the first version of the progress indicator in accordance with a selected number of cycles.

In some embodiments, the processing unit 1108 is further configured to: prior to initiating the breathing phase of the second breathing sequence: receive (e.g., with receiving unit 1118) a second user input; and in response to receiving the second user input, adjust (e.g., with adjusting unit 1126) a number of cycles of the second breathing sequence to the selected number of cycles.

In some embodiments, the processing unit 1108 is further configured to: wherein the prompt to initiate the second breathing sequence includes a second affordance, receive (e.g., with receiving unit 1118) user input selection of the second affordance; and in response to receiving the user input selection of the second affordance: cease display (e.g., with display enabling unit 1116), on the display unit 1102, of the prompt; and update (e.g., with updating unit 1120) the prompting criteria.

In some embodiments, updating the prompting criteria includes: updating the prompting criteria based on the predetermined prompting frequency and the detected time associated with the first breathing sequence.

In some embodiments, updating the prompting criteria includes: detecting a time associated with the received user input selection of the second affordance; and updating the prompting criteria based on the predetermined prompting frequency and the detected time associated with the received user input selection of the second affordance.

In some embodiments, updating the prompting criteria includes: updating the prompting criteria based on a snooze interval, wherein the predetermined prompting frequency is a predetermined length of time, and wherein the snooze interval is a length of time that is distinct from the predetermined prompting frequency.

In some embodiments, the processing unit 1108 is further configured to: further in response to receiving the user input selection of the second affordance: forgo display (e.g., with display enabling unit 1116) of all prompts to initiate a breathing sequence during the remainder of a current day.

In some embodiments, the processing unit 1108 is further configured to: determine (e.g., with determining unit 1114) if the updated prompting criteria has been met; in accordance with a determination that the updated prompting criteria has been met, enable display (e.g., with display enabling unit 1116) of, on the display unit 1102, a prompt to initiate a fourth breathing sequence, wherein the prompt includes a third affordance; receive (e.g., with receiving unit 1118) user input selection of the third affordance; and in response to receiving the user input selection of the third affordance, enable display (e.g., with display enabling unit 1116) of, on the display unit 1102, a fourth breathing sequence user interface.

The operations described above with reference to FIG. 10 are, optionally, implemented by components depicted in FIGS. 1A-1B or FIG. 11. For example, detecting operation 1002, generating operation 1010, determining operation 1014, and displaying operation 1028 are, optionally, implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 optionally utilizes or calls data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the delivery to users of invitational content or any other content that may be of interest to them. The present disclosure contemplates that in some instances, this gathered data may include personal information data that uniquely identifies or can be used to contact or locate a specific person. Such personal information data can include demographic data, location-based data, telephone numbers, email addresses, home addresses, health data, or any other identifying information.

The present disclosure recognizes that the use of such personal information data, in the present technology, can be used to the benefit of users. For example, the personal information data can be used to deliver targeted content that is of greater interest to the user. Accordingly, use of such personal information data enables calculated control of the delivered content. Further, other uses for personal information data that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services. In another example, users can select not to provide location information for targeted content delivery services. In yet another example, users can select to not provide precise location information, but permit the transfer of location zone information.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publically available information.

What is claimed is:
1. A computer-implemented method, comprising:
at a device with a display:
displaying, on the display, a configuration user interface, wherein the configuration user interface comprises a prompt to select a duration of a first breathing sequence;
receiving a first set of one or more inputs including a first user input including selection of a first duration of the first breathing sequence;
in response to receiving the first set of or more inputs, adjusting the duration of the first breathing sequence to the selected first duration;
initiating the first breathing sequence;
during the first breathing sequence:
displaying, on the display, a first version of a progress indicator; and
fluctuating the first version of the progress indicator, wherein the first version of the progress indicator includes a first set of graphical objects that are associated with the selected first duration of the first breathing sequence, and wherein fluctuating the first version of the progress indicator includes:
during a first segment of time, animatedly transitioning the first version of the progress indicator from a first state that includes a first subset of graphical objects from the first set of graphical objects to a second state that includes a second subset of graphical objects from the first set of graphical objects, wherein a number of graphical objects in the second subset of graphical objects is greater than a number of graphical objects in the first subset of graphical objects; and
during a second segment of time, animatedly transitioning the first version of the progress indicator from the second state to the first state;
receiving a second set of one or more inputs including a second user input including selection of a second duration of a second breathing sequence;

in response to receiving the second set of one or more inputs including the second user input, adjusting the duration of the second breathing sequence to the selected second duration;

initiating the second breathing sequence; and during the second breathing sequence:

displaying, on the display, a second version of a progress indicator; and fluctuating the second version of the progress indicator, wherein the second version of the progress indicator includes a second set of graphical objects that are associated with the selected second duration of the second breathing sequence, and wherein fluctuating the second version of the progress indicator includes:

during a third segment of time, animatedly transitioning the second version of the progress indicator from a third state that includes a third subset of graphical objects from the second set of graphical objects to a fourth state that includes a fourth subset of graphical objects from the second set of graphical objects, wherein a number of graphical objects in the fourth subset of graphical objects is greater than a number of graphical objects in the third subset of graphical objects; and during a fourth segment of time, animatedly transitioning the second version of the progress indicator from the fourth state to the third state.

2. The computer-implemented method of claim 1, wherein the device includes a rotatable input mechanism, and wherein the first user input and the second user input are a rotation of the rotatable input mechanism.

3. The computer-implemented method of claim 1, further comprising:

prior to initiating the first or the second breathing sequence:

receiving a third user input; and in response to receiving the third user input, progressing to the first or the second breathing sequence.

4. The computer-implemented method of claim 1, wherein each respective breathing sequence comprises a first period of time and a second period of time distinct from the first period, and wherein fluctuating the first or the second version of the progress indicator comprises:

during each respective breathing sequence:

changing, at a start of the first period of time, a first variable visual characteristic of the progress indicator; and changing, at the start of the second period of time, the first variable visual characteristic of the progress indicator.

5. The computer-implemented method of claim 4, wherein the first variable visual characteristic is a size of the displayed respective progress indicator, wherein changing, at the start of the first period of time, the first variable visual characteristic comprises increasing the size of the displayed respective progress indicator, and wherein changing, at the start of the second period of time, the first variable visual characteristic comprises decreasing the size of the displayed respective progress indicator.

6. The computer-implemented method of claim 4, wherein the device includes a haptic output device, the method further comprising:

during the first or the second breathing sequence, outputting one or more haptic breathing cues according to a haptic profile.

7. The computer-implemented method of claim 6, wherein outputting the one or more haptic breathing cues according to the haptic profile comprises:

outputting a first plurality of haptic breathing cues at a first frequency between cues during the first period of time; and outputting a second plurality of haptic breathing cues at a second frequency between cues during the second period of time.

8. The computer-implemented method of claim 7, wherein the first frequency between cues is an increasing frequency, and wherein the second frequency between cues is a constant frequency.

9. The computer-implemented method of claim 6, wherein outputting the one or more haptic breathing cues according to the haptic profile comprises:

outputting, at the start of the first period of time, a first number of haptic breathing cues; and outputting, at the start of the second period of time, a second number of haptic breathing cues, wherein the first number and the second number are different.

10. The computer-implemented method of claim 1, wherein the device includes a sensor, the method further comprising:

receiving a first signal from the sensor during the first or the second the breathing sequence;

determining an estimated heart rate based at least in part on the received first signal; and displaying, on the display, an indication of the estimated heart rate.

11. The computer-implemented method of claim 10, wherein the indication of the estimated heart rate is displayed subsequent to completion of the first or the second breathing sequence.

12. The computer-implemented method of claim 1, further comprising:

suppressing, during the first or the second breathing sequence, output of at least a subset of alerts that the device is configured to output.

13. The computer-implemented method of claim 1, further comprising:

during the first or the second breathing sequence, receiving a fourth user input;

determining whether the fourth user input meets a breathing sequence interrupt criteria;

in accordance with a determination that the fourth user input meets the breathing sequence interrupt criteria, ending the first or the second breathing sequence; and subsequent to ending the first or the breathing sequence:

displaying, on the display, an indication of an aggregate amount of completed duration of breathing sequences.

14. The computer-implemented method of claim 1, further comprising:

receiving a second signal during the respective breathing sequence;

determining an estimated breathing pattern based at least in part on the received second signal; and synchronizing the initiation of the first or the second breathing sequence and the display of the progress indicator during the first or the second breathing sequence with the estimated breathing pattern.

15. The computer-implemented method of claim 14, wherein synchronizing the initiation of the first or the second breathing sequence and the display of the progress indicator during the first or the second breathing sequence with the estimated breathing pattern comprises:
  determining a synchronization event that is a transition between an inhale period and an exhale period of the estimated breathing pattern; and
  in accordance with a determination that the synchronization event has occurred:
    initiating the first or the second breathing sequence; and
    displaying, on the display, the first version or the second version of the progress indicator, respectively.

16. The computer-implemented method of claim 14, wherein the device includes a sensor, and wherein receiving the second signal comprises:
  receiving the second signal from the sensor during the respective breathing sequence.

17. An electronic device, comprising:
a display;
one or more processors; and
memory storing one or more programs configured to be executed by the one or more processors, the one or more programs including instructions for:
  displaying, on the display, a configuration user interface, wherein the configuration user interface comprises a prompt to select a duration of a first breathing sequence;
  receiving a first set of one or more inputs including a first user input including selection of a first duration of the first breathing sequence;
  in response to receiving the first set of or more inputs, adjusting the duration of the first breathing sequence to the selected first duration;
  initiating the first breathing sequence;
  during the first breathing sequence:
    displaying, on the display, a first version of a progress indicator; and
    fluctuating the first version of the progress indicator, wherein the first version of the progress indicator includes a first set of graphical objects that are associated with the selected first duration of the first breathing sequence, and wherein fluctuating the first version of the progress indicator includes:
      during a first segment of time, animatedly transitioning the first version of the progress indicator from a first state that includes a first subset of graphical objects from the first set of graphical objects to a second state that includes a second subset of graphical objects from the first set of graphical objects, wherein a number of graphical objects in the second subset of graphical objects is greater than a number of graphical objects in the first subset of graphical objects; and
      during a second segment of time, animatedly transitioning the first version of the progress indicator from the second state to the first state;
  receiving a second set of one or more inputs including a second user input including selection of a second duration of a second breathing sequence;
  in response to receiving the second set of one or more inputs including the second user input, adjusting the duration of the second breathing sequence to the selected second duration;
  initiating the second breathing sequence; and
  during the second breathing sequence:
    displaying, on the display, a second version of a progress indicator; and
    fluctuating the second version of the progress indicator, wherein the second version of the progress indicator includes a second set of graphical objects that are associated with the selected second duration of the second breathing sequence, and wherein fluctuating the second version of the progress indicator includes:
      during a third segment of time, animatedly transitioning the second version of the progress indicator from a third state that includes a third subset of graphical objects from the second set of graphical objects to a fourth state that includes a fourth subset of graphical objects from the second set of graphical objects, wherein a number of graphical objects in the fourth subset of graphical objects is greater than a number of graphical objects in the third subset of graphical objects; and
      during a fourth segment of time, animatedly transitioning the second version of the progress indicator from the fourth state to the third state.

18. The electronic device of claim 17, wherein the device includes a rotatable input mechanism, and wherein the first user input and the second user input are a rotation of the rotatable input mechanism.

19. The electronic device of claim 17, the one or more programs further including instructions for:
  prior to initiating the first or the second breathing sequence:
    receiving a third user input; and
    in response to receiving the third user input, progressing to the first or the second breathing sequence.

20. The electronic device of claim 17, wherein each respective breathing sequence comprises a first period of time and a second period of time distinct from the first period, and wherein fluctuating the first or the second version of the progress indicator comprises:
  during each respective breathing sequence:
    changing, at a start of the first period of time, a first variable visual characteristic of the progress indicator; and
    changing, at the start of the second period of time, the first variable visual characteristic of the progress indicator.

21. The electronic device of claim 20, wherein the first variable visual characteristic is a size of the displayed respective progress indicator,
  wherein changing, at the start of the first period of time, the first variable visual characteristic comprises increasing the size of the displayed respective progress indicator, and
  wherein changing, at the start of the second period of time, the first variable visual characteristic comprises decreasing the size of the displayed respective progress indicator.

22. The electronic device of claim 20, wherein the device includes a haptic output device, the one or more programs further including instructions for:
  during the first or the second breathing sequence, outputting one or more haptic breathing cues according to a haptic profile.

23. The electronic device of claim 22, wherein outputting the one or more haptic breathing cues according to the haptic profile comprises:

outputting a first plurality of haptic breathing cues at a first frequency between cues during the first period of time; and outputting a second plurality of haptic breathing cues at a second frequency between cues during the second period of time.

24. The electronic device of claim 23, wherein the first frequency between cues is an increasing frequency, and wherein the second frequency between cues is a constant frequency.

25. The electronic device of claim 22, wherein outputting the one or more haptic breathing cues according to the haptic profile comprises:

outputting, at the start of the first period of time, a first number of haptic breathing cues; and outputting, at the start of the second period of time, a second number of haptic breathing cues, wherein the first number and the second number are different.

26. The electronic device of claim 17, wherein the device includes a sensor, the one or more programs further including instructions for:

receiving a first signal from the sensor during the first or the second the breathing sequence;

determining an estimated heart rate based at least in part on the received first signal; and displaying, on the display, an indication of the estimated heart rate.

27. The electronic device of claim 26, wherein the indication of the estimated heart rate is displayed subsequent to completion of the first or the second breathing sequence.

28. The electronic device of claim 17, the one or more programs further including instructions for:

suppressing, during the first or the second breathing sequence, output of at least a subset of alerts that the device is configured to output.

29. The electronic device of claim 17, the one or more programs further including instructions for:

during the first or the second breathing sequence, receiving a fourth user input;

determining whether the fourth user input meets a breathing sequence interrupt criteria;

in accordance with a determination that the fourth user input meets the breathing sequence interrupt criteria, ending the first or the second breathing sequence; and subsequent to ending the first or the breathing sequence:
displaying, on the display, an indication of an aggregate amount of completed duration of breathing sequences.

30. The electronic device of claim 17, the one or more programs further including instructions for:

receiving a second signal during the respective breathing sequence;

determining an estimated breathing pattern based at least in part on the received second signal; and synchronizing the initiation of the first or the second breathing sequence and the display of the progress indicator during the first or the second breathing sequence with the estimated breathing pattern.

31. The electronic device of claim 30, wherein synchronizing the initiation of the first or the second breathing sequence and the display of the progress indicator during the first or the second breathing sequence with the estimated breathing pattern comprises:

determining a synchronization event that is a transition between an inhale period and an exhale period of the estimated breathing pattern; and in accordance with a determination that the synchronization event has occurred:
initiating the first or the second breathing sequence; and
displaying, on the display, the first version or the second version of the progress indicator, respectively.

32. The electronic device of claim 30, wherein the device includes a sensor, and wherein receiving the second signal comprises:
receiving the second signal from the sensor during the respective breathing sequence.

33. A non-transitory computer-readable storage medium storing one or more programs configured to be executed by one or more processors of an electronic device with a display, the one or more programs including instructions for:

displaying, on the display, a configuration user interface, wherein the configuration user interface comprises a prompt to select a duration of a first breathing sequence;

receiving a first set of one or more inputs including a first user input including selection of a first duration of the first breathing sequence;

in response to receiving the first set of or more inputs, adjusting the duration of the first breathing sequence to the selected first duration;

initiating the first breathing sequence;

during the first breathing sequence:
displaying, on the display, a first version of a progress indicator; and
fluctuating the first version of the progress indicator, wherein the first version of the progress indicator includes a first set of graphical objects that are associated with the selected first duration of the first breathing sequence, and wherein fluctuating the first version of the progress indicator includes:
during a first segment of time, animatedly transitioning the first version of the progress indicator from a first state that includes a first subset of graphical objects from the first set of graphical objects to a second state that includes a second subset of graphical objects from the first set of graphical objects, wherein a number of graphical objects in the second subset of graphical objects is greater than a number of graphical objects in the first subset of graphical objects; and
during a second segment of time, animatedly transitioning the first version of the progress indicator from the second state to the first state;

receiving a second set of one or more inputs including a second user input including selection of a second duration of a second breathing sequence;

in response to receiving the second set of one or more inputs including the second user input, adjusting the duration of the second breathing sequence to the selected second duration;

initiating the second breathing sequence; and during the second breathing sequence:
displaying, on the display, a second version of a progress indicator; and
fluctuating the second version of the progress indicator, wherein the second version of the progress indicator includes a second set of graphical objects that are associated with the selected second duration of the second breathing sequence, and wherein fluctuating the second version of the progress indicator includes:

during a third segment of time, animatedly transitioning the second version of the progress indicator from a third state that includes a third subset of graphical objects from the second set of graphical objects to a fourth state that includes a fourth subset of graphical objects from the second set of graphical objects, wherein a number of graphical objects in the fourth subset of graphical objects is greater than a number of graphical objects in the third subset of graphical objects; and during a fourth segment of time, animatedly transitioning the second version of the progress indicator from the fourth state to the third state.

34. The computer-readable storage medium of claim 33, wherein the device includes a rotatable input mechanism, and wherein the first user input and the second user input are a rotation of the rotatable input mechanism.

35. The computer-readable storage medium of claim 33, the one or more programs further including instructions for:
prior to initiating the first or the second breathing sequence:
receiving a third user input; and
in response to receiving the third user input, progressing to the first or the second breathing sequence.

36. The computer-readable storage medium of claim 33, wherein each respective breathing sequence comprises a first period of time and a second period of time distinct from the first period, and wherein fluctuating the first or the second version of the progress indicator comprises:
during each respective breathing sequence:
changing, at a start of the first period of time, a first variable visual characteristic of the progress indicator; and
changing, at the start of the second period of time, the first variable visual characteristic of the progress indicator.

37. The computer-readable storage medium of claim 36, wherein the first variable visual characteristic is a size of the displayed respective progress indicator,
wherein changing, at the start of the first period of time, the first variable visual characteristic comprises increasing the size of the displayed respective progress indicator, and
wherein changing, at the start of the second period of time, the first variable visual characteristic comprises decreasing the size of the displayed respective progress indicator.

38. The computer-readable storage medium of claim 36, wherein the device includes a haptic output device, the one or more programs further including instructions for:
during the first or the second breathing sequence, outputting one or more haptic breathing cues according to a haptic profile.

39. The computer-readable storage medium of claim 38, wherein outputting the one or more haptic breathing cues according to the haptic profile comprises:
outputting a first plurality of haptic breathing cues at a first frequency between cues during the first period of time; and
outputting a second plurality of haptic breathing cues at a second frequency between cues during the second period of time.

40. The computer-readable storage medium of claim 39, wherein the first frequency between cues is an increasing frequency, and wherein the second frequency between cues is a constant frequency.

41. The computer-readable storage medium of claim 38, wherein outputting the one or more haptic breathing cues according to the haptic profile comprises:
outputting, at the start of the first period of time, a first number of haptic breathing cues; and
outputting, at the start of the second period of time, a second number of haptic breathing cues, wherein the first number and the second number are different.

42. The computer-readable storage medium of claim 33, wherein the device includes a sensor, the one or more programs further including instructions for:
receiving a first signal from the sensor during the first or the second the breathing sequence;
determining an estimated heart rate based at least in part on the received first signal; and
displaying, on the display, an indication of the estimated heart rate.

43. The computer-readable storage medium of claim 42, wherein the indication of the estimated heart rate is displayed subsequent to completion of the first or the second breathing sequence.

44. The computer-readable storage medium of claim 33, the one or more programs further including instructions for:
suppressing, during the first or the second breathing sequence, output of at least a subset of alerts that the device is configured to output.

45. The computer-readable storage medium of claim 33, the one or more programs further including instructions for:
during the first or the second breathing sequence, receiving a fourth user input;
determining whether the fourth user input meets a breathing sequence interrupt criteria;
in accordance with a determination that the fourth user input meets the breathing sequence interrupt criteria, ending the first or the second breathing sequence; and
subsequent to ending the first or the breathing sequence:
displaying, on the display, an indication of an aggregate amount of completed duration of breathing sequences.

46. The computer-readable storage medium of claim 33, the one or more programs further including instructions for:
receiving a second signal during the respective breathing sequence;
determining an estimated breathing pattern based at least in part on the received second signal; and
synchronizing the initiation of the first or the second breathing sequence and the display of the progress indicator during the first or the second breathing sequence with the estimated breathing pattern.

47. The computer-readable storage medium of claim 46, wherein synchronizing the initiation of the first or the second breathing sequence and the display of the progress indicator during the first or the second breathing sequence with the estimated breathing pattern comprises:
determining a synchronization event that is a transition between an inhale period and an exhale period of the estimated breathing pattern; and
in accordance with a determination that the synchronization event has occurred:
initiating the first or the second breathing sequence; and
displaying, on the display, the first version or the second version of the progress indicator, respectively.

48. The computer-readable storage medium of claim 46, wherein the device includes a sensor, and wherein receiving the second signal comprises:

receiving the second signal from the sensor during the respective breathing sequence.

\* \* \* \* \*